United States Patent [19]

Goldstein et al.

[11] Patent Number: 5,786,191
[45] Date of Patent: Jul. 28, 1998

[54] CLONING AND EXPRESSION OF COMPLEMENTARY DNAS FOR MULTIPLE MEMBERS OF THE HUMAN CYTOCHROME P450 2C SUBFAMILY

[76] Inventors: Joyce A. Goldstein, 10501 New Arden Way, Raleigh, N.C. 27613; Marjorie Romkes-Sparks, 4 Lockwood Rd., Export, Pa. 15632

[21] Appl. No.: 201,118

[22] Filed: Feb. 22, 1994

Related U.S. Application Data

[63] Continuation-in-part of Ser. No. 864,962, Apr. 9, 1992, abandoned.

[51] Int. Cl.$^6$ .............................. C12N 9/02; C12N 1/20; C12P 21/06; C07H 19/00
[52] U.S. Cl. .................... 435/189; 435/7.2; 435/69.1; 435/240.2; 435/252.3; 435/255.1; 435/320.1; 514/2; 514/12; 536/22.1; 536/23.1; 536/23.2; 536/23.5
[58] Field of Search .................... 435/7.2, 69.1, 435/189, 240.2, 252.3, 255, 320.1; 536/22.1, 23.1, 23.2, 23.5; 514/2, 12

[56] References Cited

U.S. PATENT DOCUMENTS

| 4,943,521 | 7/1990 | Blackburn et al. | 435/6 |
|---|---|---|---|
| 4,997,757 | 3/1991 | Schiestl | 435/172.1 |

OTHER PUBLICATIONS

Knodell et al., "Hepatic metabolism of tolbutamide: characterization of the form of cytochrome P-450 involved in methyl hydroxylation and relationship to in vivo disposition," J. Pharmacol. Exper. Ther. 241:1112-1119 (1987).

Romkes et al., "Cloning and expression of complememtary DNAs for multiple members of the human cytochrome P450IIC subfamily," Biochemistry 30:3247-3255 (1991).

Umbenhauer et al., "Cloning and sequence determination of a complementary DNA related to human liver microsomal cytochrome P-450 S-mephenytoin 4-hydroxylase," Biochemistry 26(4):1094-1099 (1987).

Glover, David M., "Gene cloning: The mechanics of DNA manipulation," pp. 1-20; 110-126; 179-213 (Chapman and Hall Ltd., London (1984)).

de Morais et al., "Gene structure and upstream regulatory regions of human CYP2C9 and CYP2C18," Biochemical and Biophysical Research Comm. 194(1):194-200 (1993).

Goldstein et al., "Evidence that CYP2C19 is the major (S)-mephenytoin 4'-hydroxylase in humans," Biochemistry 33:1743-1752 (1994).

Kaminsky et al., "Correlation of human cytochrome P4502C substrate specificities with primary structure: warfarin as a probe," Molecular Pharmacology 43(2):234-239 (1993).

Küpfer et al., "Pharmacogenetics of mephenytoin: a new drug hydroxylation polymorphism in man," Eur. J. Clin. Pharmacol. 26:753-759 (1984).

Nakamura et al., "Interethnic differences in genetic polymorphism of debrisoquin and mephenytoin hydroxylation between Japanese and Caucasian populations," Clin. Pharmacol. Ther. 38(4):402-408 (1985).

Romkes et al., "Cloning and expression of complementary DNAs for multiple members of the human cytochrome P450IIC subfamily," Biochemistry 32:1390 (1993) [Correction to Biochemistry 30:3247-3255 (1991)].

Romkes et al., "Cloning and expression of complementary DNAs for multiple members of the human cytochrome P4502C subfamily," FASEB p. A1163, Abstract 4595 (1991).

Srivastava et al., "Separation of human liver microsomal tolbutamide hydroxylase and (S)-mephenytoin 4'-hydroxylase cytochrome P-450 enzymes," Mol. Pharmacol. 40:69-69 (1991).

Yasumori et al., "Expression of a human P-450IIC gene in yeast cells using galactose-inducible expression system," Mol. Pharmacol. 35:443-449 (1990).

Primary Examiner—Dian C. Jacobson
Assistant Examiner—Hyosuk Kim
Attorney, Agent, or Firm—Townsend & Townsend & Crew

[57] ABSTRACT

The invention provides two novel members of the cytochrome P450 2C subfamily of enzymes, designated 2C18 and 2C19. DNA segments encoding these enzymes are also provided. The 2C19 polypeptide represents the principal human determinant of human S-mephenytoin 4'-hydroxylase activity. The invention also provides methods of identifying drugs metabolized by S-mephenytoin 4'-hydroxylase activity. Drugs shown to be metabolized by this activity should in general not be administered to individuals having, or belong to an ethnic group at risk of, a polymorphic deficiency in S-mephenytoin 4'-hydroxylase activity.

14 Claims, 22 Drawing Sheets anti-IIC9
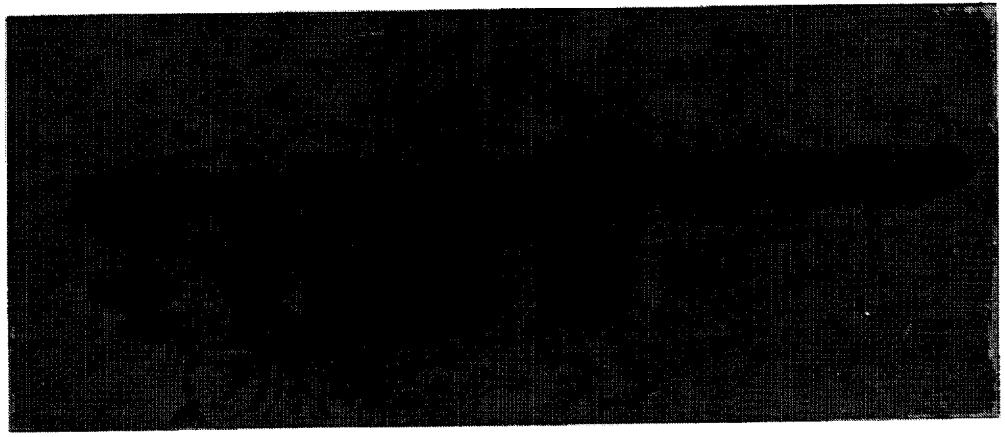
g  S5  S7  S9  S23  S30  S31  S33  860624
anti-IIC8
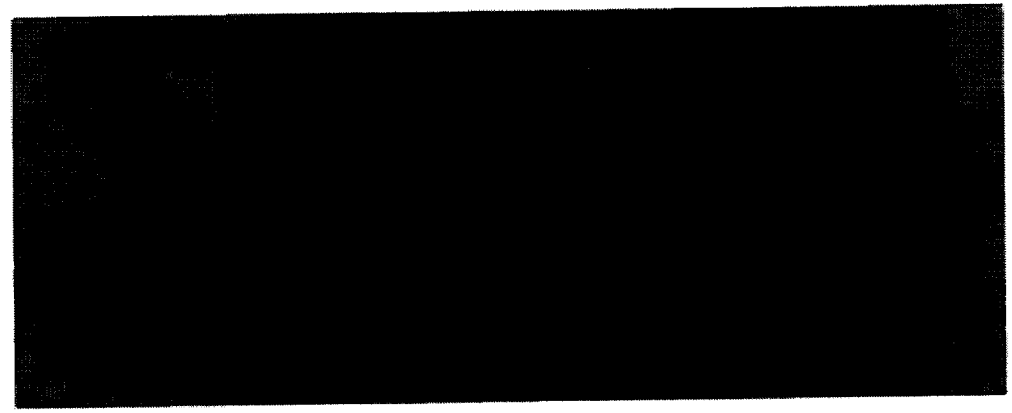
g  S5  S7  S9  S23  S30  S31  S33  860624
FIG. 1

```
       -200                                                           -150
  2c   ..........  ..........  ..........  ..........  ..........
 2c8   ..........  ..........  ..........  ..........  ..........
  25   ..........  ..........  ..........  ..........  ..........
 29c   .GGCACCGGA  AAGAACAAGA  AAAAAGAACA  CCTTATTTTT  ATCTTCTTCA
  6b   ..........  ..........  ..........  ..........  ..........
 11a   ..........  ..........  ..........  ..........  ..........

-151                                                           -100
  2c   ..........  ..........  ..........  ..........  ..........
 2c8   ..........  ..........  ..........  ..........  ..........
  25   ..........  ..........  ..........  ..........  ..........
  65   ..........  ..........  ..........  ..........  ..........
 29c   GTGAGCCAAT  GTTCATTCAA  AAGAGAGATT  AAAGTGCTTT  TTGCTGACTA
  6b   ..........  ..........  ..........  ..........  ..........
 11a   ..........  ..........  ..........  ..........  ..........

-101                                                            -50
  2c   ..........  ..........  ..........  ..........  ..........
 2c8   ..........  ..........  ..........  ..........  ..........
  25   ..........  ..........  ..........  ..........  ..........
  65   ..........  ..........  ..........  ..........  ..........
 29c   GTCACAGTCA  GAGTCAGAAT  CACAGGTGGA  TTAGTAGGGA  GTGTTATAAA
  6b   ..........  ..........  ..........  ..........  ..........
 11a   ..........  ..........  ..........  ..........  ..........

-51                                                             -1
  2c   ........AG  TGAAAGCCCG  CAGTTGTCTT  ACTAAGAAGA  GAAG.CTTCA
 2c8   ..........  ..........  ..........  ..........  .........A
  25   ..........  ..........  ..........  ..........  ......GA GAAGGCTTCA
  65   ..........  ..........  ..........  ..........  GAAGGCTTCA
 29c   AGCCTTGAAG  TGAAAGCCCG  CAGTTGTCTT  ACTAAGAAGA  GAAGCCTTCA
  6b   ........AG  TGAAAGCCCG  CAGTTGTCTT  ACTAAGAAGA  GAAGCCTTCA
 11a   ..........  ..........  ..........  ..........  .....CTTCA 1                                                             50
  2c   ATGGAtcCt.  tTGTGGtcCT  .TGTCTcTGT  CTCTCaTgTt  TGcTTCTCcT
 2c8   ATGGAACCTT  TTGTGGTCCT  GGTGCTGTGT  CTCTCTTTTA  TGCTTCTCTT
  25   ATGGATTCTC  TTGTGGTCCT  TGTGCTCTGT  CTCTCATGTT  TGCTTCTCCT
  65   ATGGATTCTC  TTGTGGTCCT  TGTGCTCTGT  CTCTCATGTT  TGCTTCTCCT
 29c   ATGGATCCAG  CTGTGGCTCT  GGTGCTCTGT  CTCTCCTGTT  TGTTTCTCCT
  6b   ATGGATCCAG  CTGTGGCTCT  GGTGCTCTGT  CTCTCCTGTT  TGTTTCTCCT
 11a   ATGGATCCTT  TTGTGGTCCT  TGTGCTCTGT  CTCTCATGTT  TGCTTCTCCT
```

*FIG. 2-1.*

```
      51                                                               100
 2c  TTCAcTCTGG  AGaCAGAGCT  cTgGgAGAgG  .Aa.CTCCCt  cCTGGCCCCA
 2c8 TTCACTCTGG  AGACAGAGCT  GTAGGAGAAG  GAAGCTCCCT  CCTGGCCCCA
 25  TTCACTCTGG  AGACAGAGCT  CTGGGAGAGG  AAAACTCCCT  CCTGGCCCCA
 65  TTCACTCTGG  AGACAGAGCT  CTGGGAGAGG  AAAACTCCCT  CCTGGCCCCA
 29c TTCACTCTGG  AGGCAGAGCT  CTGGAAGAGG  GAGGCTCCCG  TCTGGCCCCA
 6b  TTCACTCTGG  AGGCAGAGCT  CTGGAAGAGG  GAGGCTCCCG  TCTGGCCCCA
 11a TTCAATCTGG  AGACAGAGCT  CTGGGAGAGG  AAAACTCCCT  CCTGGCCCCA 101                                                              150
 2c  CTCCTCTcCC  a.T.ATTGGA  AATATcCTaC  AGaTAGaT.T  TAAGGAcaTc
 2c8 CTCCTCTTCC  TATTATTGGA  AATATGCTAC  AGATAGATGT  TAAGGACATC
 25  CTCCTCTCCC  AGTGATTGGA  AATATCCTAC  AGATAGGTAT  TAAGGACATC
 65  CTCCTCTCCC  AGTGATTGGA  AATATCCTAC  AGATAGGTAT  TAAGGACATC
 29c CTCCTCTCCC  GATTATTGGA  AATATCCTGC  AGTTAGATGT  TAAGGACATG
 6b  CTCCTCTCCC  GATTATTGGA  AATATCCTGC  AGTTAGATGT  TAAGGACATG
 11a CTCCTCTCCC  AGTGATTGGA  AATATCCTAC  AGATAGATAT  TAAGGATGTC 151                                                              200
 2c  aGCAAATCcT  TaACCAAT.T  CTCAAAagTC  TATGGcCCTG  TGTTCACt.T
 2c8 TGCAAATCTT  TCACCAATTT  CTCAAAAGTC  TATGGTCCTG  TGTTCACCGT
 25  AGCAAATCCT  TAACCAATCT  CTCAAAGGTC  TATGGCCCTG  TGTTCACTCT
 65  AGCAAATCCT  TAACCAATCT  CTCAAAGGTC  TATGGCCCTG  TGTTCACTCT
 29c AGCAAATCCT  TAACCAATTT  CTCAAAAGTC  TATGGCCCTG  TGTTCACTGT
 6b  AGCAAATCCT  TAACCAATTT  CTCAAAAGTC  TATGGCCCTG  TGTTCACTGT
 11a AGCAAATCCT  TAACCAATCT  CTCAAAAATC  TATGGCCCTG  TGTTCACTCT 201                                                              250
 2c  GTATTTTGGC  cTGaAaCcCA  TaGTGGTG.T  gCATGGATAT  GAaGcaGTGA
 2c8 GTATTTTGGC  ATGAATCCCA  TAGTGGTGTT  TCATGGATAT  GAGGCAGTGA
 25  GTATTTTGGC  CTGAAACCCA  TAGTGGTGCT  GCATGGATAT  GAAGCAGTGA
 65  GTATTTTGGC  CTGAAACCCA  TAGTGGTGCT  GCATGGATAT  GAAGCAGTGA
 29c GTATTTTGGC  CTGAAGCCCA  TTGTGGTGTT  GCATGGATAT  GAAGCAGTGA
 6b  GTATTTTGGC  CTGAAGCCCA  TTGTGGTGTT  GCATGGATAT  GAAGCAGTGA
 11a GTATTTTGGC  CTGGAACGCA  TGGTGGTGCT  GCATGGATAT  GAAGTGGTGA 251                                                              300
 2c  AGGAaGCCCT  GATTGATc.T  GGAGAGGAGT  TTTCTGGAAG  AGGca.TTtc
 2c8 AGGAAGCCCT  GATTGATAAT  GGAGAGGAGT  TTTCTGGAAG  AGGCAATTCC
 25  AGGAAGCCCT  GATTGATCTT  GGAGAGGAGT  TTTCTGGAAG  AGGCATTTTC
 65  AGGAAGCCCT  GATTGATCTT  GGAGAGGAGT  TTTCTGGAAG  AGGCATTTTC
 29c AGGAGGCCCT  GATTGATCAT  GGAGAGGAGT  TTTCTGGAAG  AGGAAGTTTT
 6b  AGGAGGCCCT  GATTGATCAT  GGAGAGGAGT  TTTCTGGAAG  AGGAAGTTTT
 11a AGGAAGCCCT  GATTGATCTT  GGAGAGGAGT  TTTCTGGAAG  AGGCCATTTC
```

FIG. 2-2.

```
        301                                                              350
   2c   CCAcTggCTg  AAAgAg.TAa  cA.AGGA>TT  GGAATcgTTT  tCAGCAATGG
  2c8   CCAATATCTC  AAAGAATTAC  TAAAGGACTT  GGAATCATTT  CCAGCAATGG
   25   CCACTGGCTG  AAAGAGCTAA  CAGAGGATTT  GGAATTGTTT  TCAGCAATGG
   65   CCACTGGCTG  AAAGAGCTAA  CAGAGGATTT  GGAATTGTTT  TCAGCAATGG
  29c   CCAGTGGCTG  AAAAAGTTAA  CAAAGGACTT  GGAATCCTTT  TCAGCAATGG
   6b   CCAGTGGCTG  AAAAAGTTAA  CAAAGGACTT  GGAATCCTTT  TCAGCAATGG
  11a   CCACTGGCTG  AAAGAGCTAA  CAGAGGATTT  GGAATCGTTT  TCAGCAATGG 351                                                              400
   2c   AAAGAgATGG  AAGGAGATCC  GGCGTTTCTc  CCTCAtgAcg  cTGCGGAATT
  2c8   AAAGAGATGG  AAGGAGATCC  GGCGTTTCTC  CCTCACAAAC  TTGCGGAATT
   25   AAAGAAATGG  AAGGAGATCC  GGCGTTTCTC  CCTCATGACG  CTGCGGAATT
   65   AAAGAAATGG  AAGGAGATCC  GGCGTTTCTC  CCTCATGACG  CTGCGGAATT
  29a   AAAGAGATGG  AAGGAGATCC  GGCGTTTCTG  CCTCATGACT  CTGCGGAATT
   6b   AAAGAGATGG  AAGGAGATCC  GGCGTTTCTG  CCTCATGACT  CTGCGGAATT
  11a   AAAGAGATGG  AAGGAGATCC  GGCGTTTCTC  CCTCATGACG  CTGCGGAATT 401                                                              450
   2c   TTGGGATGGG  GAAGAGGAGC  ATtGAGGACC  GTGTTCAAGA  GGAAGCcCgC
  2c8   TTGGGATGGG  GAAGAGGAGC  ATTGAGGACC  GTGTTCAAGA  GGAAGCTCAC
   25   TTGGGATGGG  GAAGAGGAGC  ATTGAGGACC  GTGTTCAAGA  GGAAGCCCGC
   65   TTGGGATGGG  GAAGAGGAGC  ATTGAGGACC  GTGTTCAAGA  GGAAGCCCGC
  29c   TTGGGATGGG  GAAGAGGAGC  ATCGAGGACC  GTGTTCAAGA  GGAAGCCCGC
   6b   TTGGGATGGG  GAAGAGGAGC  ATCGAGGACC  GTGTTCAAGA  GGAAGCCCGC
  11a   TTGGGATGGG  GAAGAGGAGC  ATTGAGGACC  GTGTTCAAGA  GGAAGCCCGC 451                                                              500
   2c   TGCCTTGTGG  AGGAGTTGAG  AAAAACCAAg  GCcTCACCCT  GTGATCCCAC
  2c8   TGCCTTGTGG  AGGAGTTGAG  AAAAACCAAG  GCTTCACCCT  GTGATCCCAC
   25   TGCCTTGTGG  AGGAGTTGAG  AAAAACCAAG  GCCTCACCCT  GTGATCCCAC
   65   TGCCTTGTGG  AGGAGTTGAG  AAAAACCAAG  GCCTCACCCT  GTGATCCCAC
  29c   TGCCTTGTGG  AGGAGTTGAG  AAAAACCAAT  GCCTCACCCT  GTGATCCCAC
   6b   TGCCTTGTGG  AGGAGTTGAG  AAAAACCAAT  GCCTCACCCT  GTGATCCCAC
  11a   TGCCTTGTGG  AGGAGTTGAG  AAAAACCAAG  GCTTCACCCT  GTGATCCCAC 501                                                              550
   2c   TTTCATCCTG  GGCTGTGCTC  CCTGCAATGT  GATCTGCTCc  .TTaTTTTCC
  2c8   TTTCATCCTG  GGCTGTGCTC  CCTGCAATGT  GATCTGCTCC  GTTGTTTTCC
   25   TTTCATCCTG  GGCTGTGCTC  CCTGCAATGT  GATCTGCTCC  ATTATTTTCC
   65   TTTCATCCTG  GGCTGTGCTC  CCTGCAATGT  GATCTGCTCC  ATTATTTTCC
  29c   TTTCATCCTG  GGCTGTGCTC  CCTGCAATGT  GATCTGCTCT  GTTATTTTCC
   6b   TTTCATCCTG  GGCTGTGCTC  CCTGCAATGT  GATCTGCTCT  GTTATTTTCC
  11a   TTTCATCCTG  GGCTGTGCTC  CCTGCAATGT  GATCTGCTCC  ATTATTTTCC
```

FIG. 2-3.

```
      551                                                             600
 2c  AtaAaCG.TT  tGATTATAAA  GATCAG.aaT  TTCTtAaCtT  gATGgAAAaa
 2c8 AGAAACGATT  TGATTATAAA  GATCAGAATT  TTCTCACCCT  GATGAAAAGA
 25  ATAAACGTTT  TGATTATAAA  GATCAGCAAT  TTCTTAACTT  AATGGAAAAG
 65  ATAAACGTTT  TGATTATAAA  GATCAGCAAT  TTCTTAACTT  AATGGAAAAG
 29c ATGATCGATT  TGATTATAAA  GATCAGAGGT  TTCTTAACTT  GATGGAAAAA
 6b  ATGATCGATT  TGATTATAAA  GATCAGAGGT  TTCTTAACTT  GATGGAAAAA
 11a AGAAACGTTT  CGATTATAAA  GATCAGCAAT  TTCTTAACTT  GATGGAAAAA 601                                                             650
 2c  TT.AATGAAA  ACaTCAgGAT  TcTgAgC.cc  CC.TGGATCC  AG.TcTGCAA
 2c8 TTCAATGAAA  ACTTCAGGAT  TCTGAACTCC  CCATGGATCC  AGGTCTGCAA
 25  TTGAATGAAA  ACATCAAGAT  TTGAGCAGC   CCCTGGATCC  AGATCTGCAA
 65  TTGAATGAAA  ACATCAAGAT  TTGAGCAGC   CCCTGGATCC  AGATCTGCAA
 29c TTCAATGAAA  ACCTCAGGAT  TCTGAGCTCT  CCATGGATCC  AGGTCTGCAA
 6b  TTCAATGAAA  ACCTCAGGAT  TCTGAGCTCT  CCATGGATCC  AGGTCTGCAA
 11a TTGAATGAAA  ACATCAGGAT  TGTAAGCACC  CCTGGATCC   AGATATGCAA 651                                                             700
 2c  TAAttTT.cCt  cct.TCAttG  ATTattTCCC  .GGAActCA.  AAcAAAtTac
 2c8 TAATTTCCCT  CTACTCATTG  ATTGTTTCCC  AGGAACTCAC  AACAAAGTGC
 25  TAATTTTTCT  CCTATCATTG  ATTACTTCCC  GGGAACTCAC  AACAAATTAC
 65  TAATTTTTCT  CCTATCATTG  ATTACTTCCC  GGGAACTCAC  AACAAATTAC
 29c TAATTTCCCT  GCTCTCATCG  ATTATCTCCC  AGGAAGTCAT  AATAAAATAG
 6b  TAATTTCCCT  GCTCTCATCG  ATTATCTCCC  AGGAAGTCAT  AATAAAATAG
 11a TAATTTTCCC  ACTATCATTG  ATTATTTCCC  GGGAACCCAT  AACAAATTAC 701                                                             750
 2c  tTaAAAA.gT  TGCTtttAtg  aaAAGTtAta  TtttGGAgAa  AgTAAAAGAA
 2c8 TTAAAAATGT  TGCTCTTACA  CGAAGTTACA  TTAGGGAGAA  AGTAAAAGAA
 25  TTAAAAACGT  TGCTTTTATG  AAAAGTTATA  TTTTGGAAAA  AGTAAAAGAA
 65  TTAAAAACGT  TGCTTTTATG  AAAAGTTATA  TTTTGGAAAA  AGTAAAAGAA
 29c CTGAAAATTT  TGCTTACATT  AAAAGTTATG  TATTGGAGAG  AATAAAAGAA
 6b  CTGAAAATTT  TGCTTACATT  AAAAGTTATG  TATTGGAGAG  AATAAAAGAA
 11a TTAAAAACCT  TGCTTTTATG  GAAAGTGATA  TTTTGGAGAA  AGTAAAAGAA 751                                                             800
 2c  CAcCAAGaAT  Ca.TGGAcaT  gAACAa.cCT  CGGGACTTTA  TtGATTGcTT
 2c8 CACCAAGCAT  CACTGGATGT  TAACAATCCT  CGGGACTTTA  TGGATTGCTT
 25  CACCAAGAAT  CAATGGACAT  GAACAACCCT  CAGGACTTTA  TTGATTGCTT
 65  CACCAAGAAT  CAATGGACAT  GAACAACCCT  CAGGACTTTA  TTGATTGCTT
 29c CATCAAGAAT  CCCTGGACAT  GAACAGTGCT  CGGGACTTTA  TTGATTGTTT
 6b  CATCAAGAAT  CCCTGGACAT  GAACAGTGCT  CGGGACTTTA  TTGATTGTTT
 11a CACCAAGAAT  CGATGGACAT  CAACAACCCT  CGGGACTTTA  TTGATTGCTT
```

*FIG. 2-4.*

```
         801                                                          850
    2c  CCTGATcAAA ATGGAg.AGG AAAAGcAcAA cCAAcagTCt GAATTtAcTa
   2c8  CCTGATCAAA ATGGAGCAGG AAAAGGACAA CCAAAAGTCA GAATTCAATA
    25  CCTGATGAAA ATGGAGAAGG AAAAGCACAA CCAACCATCT GAATTTACTA
    65  CCTGATGAAA ATGGAGAAGG AAAAGCACAA CCAACCATCT GAATTTACTA
   29c  CCTGATCAAA ATGGAACAGG AAAAGCACAA TCAACAGTCT GAATTTACTG
    6b  CCTGATCAAA ATGGAACAGG AAAAGCACAA TCAACAGTCT GAATTTACTG
   11a  CCTGATCAAA ATGGAGAAGG AAAAGCAAAA CCAACAGTCT GAATTCACTA 851                                                          900
    2c  TTGAAAgCTT Ggta..CACT G.AgcTGA.t TgtTTGgaGC TGG.ACAGAG
   2c8  TTGAAAACTT GGTTGGCACT GTAGCTGATC TATTTGTTGC TGGAACAGAG
    25  TTGAAAGCTT GGAAAACACT GCAGTTGACT TGTTTGGAGC TGGGACAGAG
    65  TTGAAAGCTT GGAAAACACT GCAGTTGACT TGTTTGGAGC TGGGACAGAG
   29c  TTGAAAGCTT GATAGCCACT GTAACTGATA TGTTTGGGGC TGGAACAGAG
    6b  TTGAAAGCTT GATAGCCACT GTAACTGATA TGTTTGGGGC TGGAACAGAG
   11a  TTGAAAACTT GGTAATCACT GCAGCTGACT TACTTGGAGC TGGGACAGAG 901                                                          950
    2c  ACaACaAGCA C.AC.CTGAG ATATG..CTC CT.CTCCTGC TGAAGcACCC
   2c8  ACAACAAGCA CCACTCTGAG ATATGGACTC CTGCTCCTGC TGAAGCACCC
    25  ACGACAAGCA CAACCCTGAG ATATGCTCTC CTTCTCCTGC TGAAGCACCC
    65  ACGACAAGCA CAACCCTGAG ATATGCTCTC CTTCTCCTGC TGAAGCACCC
   29c  ACAACGAGCA CCACTCTGAG ATATGGACTC CTGCTCCTGC TGAAGTACCC
    6b  ACAACGAGCA CCACTCTGAG ATATGGACTC CTGCTCCTGC TGAAGTACCC
   11a  ACAACAAGCA CAACCCTGAG ATATGCTCTC CTTCTCCTGC TGAAGCACCC 951                                                         1000
    2c  AGAGGTCACA GCTAAAGTCC AGGAAGAGAT TGAacgTGTa aTTGGCAGAa
   2c8  AGAGGTCACA GCTAAAGTCC AGGAAGAGAT TGATCATGTA ATTGGCAGAC
    25  AGAGGTCACA GCTAAAGTCC AGGAAGAGAT TGAACGTGTG ATTGGCAGAA
    65  AGAGGTCACA GCTAAAGTCC AGGAAGAGAT TGAACGTGTG ATTGGCAGAA
   29c  AGAGGTCACA GCTAAAGTCC AGGAAGAGAT TGAATGTGTA GTTGGCAGAA
    6b  AGAGGTCACA GCTAAAGTCC AGGAAGAGAT TGAATGTGTA GTTGGCAGAA
   11a  AGAGGTCACA GCTAAAGTCC AGGAAGAGAT TGAACGTGTC ATTGGCAGAA 1001                                                         1050
    2c  ACcGGAGCCC CTGcATGCAg GAcAGGaGcC ACATGCCcTA CACaGATGCT
   2c8  ACAGGAGCCC CTGCATGCAG GATAGGAGCC ACATGCCTTA CACTGATGCT
    25  ACCGGAGCCC CTGCATGCAA GACAGGAGCC ACATGCCCTA CACAGATGCT
    65  ACCGGAGCCC CTGCATGCAA GACAGGAGCC ACATGCCCTA CACAGATGCT
   29c  ACCGGAGCCC CTGTATGCAG GACAGGAGTC ACATGCCCTA CACAGATGCT
    6b  ACCGGAGCCC CTGTATGCAG GACAGGAGTC ACATGCCCTA CACAGATGCT
   11a  ACCGGAGCCC CTGCATGCAG GACAGGGGCC ACATGCCCTA CACAGATGCT
```

FIG. 2-5.

```
       1051                                                      1100
2c   GTgGTGCACG AG.TCCAGAG ATACattGAC CT.cTCCCCA CCagccTGCC
2c8  GTAGTGCACG AGATCCAGAG ATACAGTGAC CTTGTCCCCA CCGGTGTGCC
25   GTGGTGCACG AGGTCCAGAG ATACCTTGAC CTTCTCCCCA CCAGCCTGCC
65   GTGGTGCACG AGGTCCAGAG ATACATTGAC CTTCTCCCCA CCAGCCTGCC
29c  GTGGTGCACG AGATCCAGAG ATACATTGAC CTCCTCCCCA CCAACCTGCC
6b   GTGGTGCACG AGATCCAGAG ATACATTGAC CTCCTCCCCA CCAACCTGCC
11a  GTGGTGCACG AGGTCCAGAG ATACATCGAC CTCATCCCCA CCAGCCTGCC 1101                                                      1150
2c   CCATGCAGTG ACCtgTGA.. tTAAaTTCAg AAACTAcCTC AT.CCCAAGG
2c8  CCATGCAGTG ACCACTGATA CTAAGTTCAG AAACTACCTC ATCCCCAAGG
25   CCATGCAGTG ACCTGTGACA TTAAATTCAG AAACTATCTC ATTCCCAAGG
65   CCATGCAGTG ACCTGTGACA TTAAATTCAG AAACTATCTC ATTCCCAAGG
29c  CCATGCAGTG ACCTGTGATG TTAAATTCAA AAACTACCTC ATCCCCAAGG
6b   CCATGCAGTG ACCTGTGATG TTAAATTCAA AAACTACCTC ATCCCCAAGG
11a  CCATGCAGTG ACCTGTGACG TTAAATTCAG AAACTACCTC ATTCCCAAGG 1151                                                      1200
2c   GCAcaACCAT A.Taac.Tcc CTgACTTCtG TGCTaCAtgA ..ACAAAGAA
2c8  GCACAACCAT AATGGCATTA CTGACTTCCG TGCTACATGA TGACAAAGAA
25   GCACAACCAT ATTAATTTCC CTGACTTCTG TGCTACATGA CAACAAAGAA
65   GCACAACCAT ATTAATTTCC CTGACTTCTG TGCTACATGA CAACAAAGAA
29c  GCACGACCAT AATAACATCC CTGACTTCTG TGCTGCACAA TGACAAAGAA
6b   GCATGACCAT AATAACATCC CTGACTTCTG TGCTGCACAA TGACAAAGAA
11a  GCACAACCAT ATTAACTTCC CTCACTTCTG TGCTACATGA CAACAAAGAA 1201                                                      1250
2c   TTtCCcAAcC CAgAgATgTT TGACCCT.g. CACTTTCTgG AT.A..gTGG
2c8  TTTCCTAATC CAAATATCTT TGACCCTGGC CACTTTCTAG ATAAGAATGG
25   TTTCCCAACC CAGAGATGTT TGACCCTCAT CACTTTCTGG ATGAAGGTGG
65   TTTCCCAACC CAGAGATGTT TGACCCTCAT CACTTTCTGG ATGAAGGTGG
29c  TTCCCCAACC CAGAGATGTT TGACCCTGGC CACTTTCTGG ATAAGAGTGG
6b   TTCCCCAACC CAGAGATGTT TGACCCTGGC CACTTTCTGG ATAAGAGTGG
11a  TTTCCCAACC CAGAGATGTT TGACCCTCGT CACTTTCTGG ATGAAGGTGG 1251                                                      1300
2c   cAA.TTTAAG AAAAGT.AcT ACTTCATGCC TTTCTCAGCA GGAAAACGgA
2c8  CAACTTTAAG AAAAGTGACT ACTTCATGCC TTTCTCAGCA GGAAAACGAA
25   CAATTTTAAG AAAAGTAAAT ACTTCATGCC TTTCTCAGCA GGAAAACGGA
65   CAATTTTAAG AAAAGTAAAT ACTTCATGCC TTTCTCAGCA GGAAAACGGA
29c  CAACTTTAAG AAAAGTGACT ACTTCATGCC TTTCTCAGCA GGAAAACGGA
6b   CAACTTTAAG AAAAGTGACT ACTTCATGCC TTTCTCAGCA GGAAAACGGA
11a  AAATTTTAAG AAAAGTAACT ACTTCATGCC TTTCTCAGCA GGAAAACGGA
```

FIG. 2-6.

```
         1301                                                           1350
   2c    TtTGTgtgGG AGA.GgcCTg GCCcGCATGG AGCTgTTTTT ATTcCTgACC
  2c8    TTTGTGCAGG AGAAGGACTT GCCCGCATGG AGCTATTTTT ATTTCTAACC
   25    TTTGTGTGGG AGAAGCCCTG GCCGGCATGG AGCTGTTTTT ATTCCTGACC
   65    TTTGTGTGGG AGAAGCCCTG GCCGGCATGG AGCTGTTTTT ATTCCTGACC
  29c    TGTGTATGGG AGAGGGCCTG GCCCGCATGG AGCTGTTTTT ATTCCTGACC
   6b    TGTGTATGGG AGAGGGCCTG GCCCGCATGG AGCTGTTTTT ATTCCTGACC
  11a    TTTGTGTGGG AGAGGGCCTG GCCCGCATGG AGCTGTTTTT ATTCCTGACC 1351                                                           1400
   2c    .ccATTTTaC AGAACTTTAA CCTGAAATCT ctggtTGAcc cAAAG.AccT
  2c8    ACAATTTTAC AGAACTTTAA CCTGAAATCT GTTGATGATT TAAAGAACCT
   25    TCCATTTTAC AGAACTTTAA CCTGAAATCT CTGGTTGACC CAAAGAACCT
   65    TCCATTTTAC AGAACTTTAA CCTGAAATCT CTGGTTGACC CAAAGAACCT
  29c    ACCATTTTGC AGAACTTTAA CCTGAAATCT CAGGTTGACC CAAAGGATAT
   6b    ACCATTTTGC AGAACTTTAA CCTGAAATCT CAGGTTGACC CAAAGGATAT
  11a    TTCATTTTAC AGAACTTTAA CCTGAAATCT CTGATTGACC CAAAGGACCT 1401                                                           1450
   2c    tgAcAccACt cCagTTg.CA AtGgatTTGc ttcTgTgCC. CCCTtcTAcC
  2c8    CAATACTACT GCAGTTACCA AAGGGATTGT TTCTCTGCCA CCCTCATACC
   25    TGACACCACT CCAGTTGTCA ATGGTTTTGC CTCTGTGCCG CCCTTCTACC
   65    TGACACCACT CCAGTTGTCA ATGGATTTGC CTCTGTGCCG CCCTTCTACC
  29c    TGACATCACC CCCATTGCCA ATGCATTTGG TCGTGTGCCA CCCTTGTACC
   6b    TGACATCACC CCCATTGCCA ATGCATTTGG TCGTGTGCCA CCCTTGTACC
  11a    TGACACAACT CCTGTTGTCA ATGGATTTGC TTCTGTCCCG CCCTTCTATC 1451                   ***                                     1500
   2c    AGcT.TGCTT CAttCCTGTC TGAAGAAggg cAGatggtcT GGCTGCT.cT
  2c8    AGATCTGCTT CATCCCTGTC TGAAGAATGC TAGCCCATCT GGCTGCTGAT
   25    AGCTGTGCTT CATTCCTGTC TGAAGAAGAG CAGATGGCCT GGCTGCTGCT
   65    AGCTGTGCTT CATTCCTGTC TGAAGAAGAG CAGATGGCCT GGCTGCTGCT
  29c    AGCTCTGCTT CATTCCTGTC TGAAGAAGGG CAGATAGTTT GGCTGCTCCT
   6b    AGCTCTGCTT CATTCCTGTC TGAAGAAGGG CAGATAGTTT GGCTGCTCCT
  11a    AGCTGTGCTT CATTCCTGTC TGAAGAAGCA CAGATGGTCT GGCTGCTCCT 1501                                                           1550
   2c    gTGCtgTC.C ......t... ttt..tctgg ggcaatttcC .tctt.cat.
  2c8    CTGCTATCAC CTGCAACTCT TTTTTATCA AGGACATTCC CACTATTATG
   25    GTGCAGTCCC TGCAGCTCTC TTTCCTCTGG GGCATTATCC ATCTTTCACT
   65    GTGCAGTCCC TGCAGCTCTC TTTCCTCTGG GGCATTATCC ATCTTTCACT
  29c    GTGCTGTCAC CTGCAATTCT CCCTTATCAG GGCCATTAGC CTCTCCCTTC
   6b    GTGCTGTCAC CTGCAATTCT CCCTTATCAG GGCCATTGGC CTCTCCCTTC
  11a    GTGCTGTCCC TGCAGCTCTC TTTCCTCTGG TCCAAATTTC ACTATCTGTG
```

FIG. 2-7.

```
             1551                                                  1600
       2c  ..t.tt..tg  c..ttt.Tca  tcTg.catct  caca.t.c..  cttccctta.
      2c8  TCTTCTCTGA  CCTCTCATCA  AATCTTCCCA  TTCACTCAAT  ATCCCATAAG
       25  ATCTGTAATG  CCTTTTCTCA  CCTGTCATCT  CACATTTTCC  CTTCCCTGAA
       65  ATCTGTAATG  CCTTTTCTCA  CCTGTCATCT  CACATTTTCC  CTTCCCTGAA
      29a  TCTCTGTGAG  GGATATTTTC  TCTGACTTGT  CAATCCACAT  CTTCCCATTC
       6b  TCTCTATGAG  GGATATTTTC  TCTGACTTGT  CAATCCACAT  CTTCCCATTC
      11a  ATGCTTCTTC  TGACCCGTCA  TCTCACATTT  TCCCTTCCCC  CAAGATCTAG 1601                                                  1650
       2c  catc.Ag..a  ccaTt.a...  .caat.tcca  agag.gtg..  ttt.Tt..ct
      2c8  CATCCAAACT  CCATTAAGGA  GAGTTGTTCA  GGTCACTGCA  CAAATATATC
       25  GATCTAGTGA  ACATTCGACC  TTCATTACGG  AGAGTTTCCT  ATGTTTCACT
       65  GATCTAGTGA  ACATTCGACC  TCCATTACTT  AGAGTTTCCT  ATGTTTCACT
      29c  CCTCAAGATC  CAATGAACAT  CCAACCTCCA  TTAAAGAGAG  TTTCTTGGGT
       6b  CCTCAAGATC  CAATGAACAT  CCAACCTCCA  TTAAAGAGAG  TTTCTTGGGT
      11a  TGAACATTCA  GCCTCCATTA  AAAAGTTTC   ACTGTGCAAA  TATATCTGCT 1651                                                  1700
       2c  .tccaccta.  atctatc..t  ....ct.ct.  t.t.t..aT.  actttgattg
      2c8  TGCAATTATT  CATACTCTGT  AACACTTGTA  TTAATTGCTG  CATATGCTAA
       25  GTGCAAATAT  ATCTGCTATT  CTCCATACTC  TGTAACAGTT  GCATTGACTG
       65  GTGCAAATAT  ATCTGCTATT  CTCCATACTC  TGTAACAGTT  GCATTGACTG
      29c  CACTTCCTAA  ATATATCTGC  TATTCTCCAT  ACTCTGTATC  ACTTGTATTG
       6b  CACTTCCTAA  ATATATCTGC  TATTCTCCAT  ACTCTGTATC  ACTTGTATTG
      11a  ATTCCCCATA  CTCTATAATA  GTTACATTGA  GTGCCACATA  ATGCTGATAC 1701                                                  1750
       2c  tcc.cta.tg  aTg.taatt.  tttaatattg  ..ttattg..  A...t.ttAt
      2c8  TACTTTTCTA  ATGCTGACTT  TTTAATATGT  TATCACTGTA  AAACACAGAA
       25  TCACATAATG  CTCATACTTA  TCTAATGTTG  AGTTATTAAT  ATGTTATTAT
       65  TCACATAATG  CTCATACTTA  TCTAATGTTG  AGTTATTAAT  ATGTTATTAT
      29c  ACCACCACAT  ATGCTAATAC  CTATCTACTG  CTGAGTTGTC  AGTATGTTAT
       6b  ACCACCACAT  ATGCTAATAC  CTATCTACTG  CTGAGTTGTC  AGTATGTTAT
      11a  TTGTCTAATG  TTGAGTTATT  AACATATTAT  TATTAAATAG  A 1751                                                  1800
       2c  .A.t.a.aaA  .aaAtgAtaa  tt.t.t..aa  aT...aagtc  A.tgc..tt.
      2c8  AAGTGATTAA  TGAATGATAA  TTTAGTCCAT  TTCTTTTGTG  AATGTGCTAA
       25  TAAATAGAGA  AATATGATTT  GTGTATTATA  ATTCAAGGC   ATTTCTTTTC
       65  TAAATAGAGA  AATATGATTT  GTGTATTATA  ATTCAAGGC   ATTTCTTTTC
      29c  CACTAGAAAA  CAAAGAAAAA  TGATTAATAA  ATGACAATTC  AGAGCCAAAA
       6b  CACTATAAAA  CAAAGAAAAA  TGATTAATAA  ATGACAATTC  AGAGCCATTT
```

*FIG. 2-8*

```
       1801                                                          1850
 2c  a..at.t.c.  .aaTaaAaag  cattaTtATT  tgctgaaAaa  aaGTCAGTTC
2c8  ATAAAAAGTG  TTATTAATTG  CTGGTTCA
 25  TGCATGTTCT  AAATAAAAAG  CATTATTATT  TGCTGAAAAA  AA
 65  TGCATGTTCT  AAATAAAAAG  CATTATTATT  TGCTGAAAAA  AA
29c  AAAAAAAAAA
 6b  ATTCTCTGCA  TGCTCTAGAT  AAAAATGATT  ATTATTTACT  GGGTCAGTTC 1851                                                          1900
 6b  TTAGATTTCT  TTCTTTTGAG  TAAAATGAAA  GTAAGAAATG  AAAGAAAATA 1901                                                          1950
 6b  GAATGTGAAG  AGGCTGTGCT  GGCCCTCATA  GTGTTAAGCA  CAAAAAGGGA 1951                                                          2000
 6b  GAAAGGTAAG  AGGGTAGGAA  AGCTGTTTTA  GCTAAATGCC  ACCTAGAGTT 2001                                                          2050
 6b  ATTGGAGGTC  TGAATTTGGA  AAAAAAAACT  ATGTCCAGGA  GAACATTAAG 2101                                                          2150
 6b  TGTTTGAATT  CATGCTCTGC  TTTTGTGTTA  CTGTAAACAC  AAGATCAAGA 2151                                                          2200
 6b  TTTGGATAAT  CTTTTTCCTT  TGTGTTTCCA  ACTTAGATCA  TGTCTAAATA 2201        2216
 6b  TATGCTTTCA  TATGGC
```

FIG. 2-9.

```
       1                                                                                              70
     Mdp.VvLVLC  LSclllslw  RQSsgRgkLP  pGPTPLP.IG  NilQid.KDi  sKSlTN.SKv  YGPVFT.YFG
1IC8 MEPFVVLVLC  LSFMLLFSLW  RQSCRRRKLP  PGPTPLPIIG  NMLQIDVKDI  CKSFTNFSKV  YGPVFTVYFG
 65  MDSLVVLVLC  LSCLLLLSLW  RQSSGRGKLP  PGPTPLPVIG  NILQIGIKDI  SKSLTNLSKV  YGPVFTLYFG
 25  MDSLVVLVLC  LSCLLLLSLW  RQSSGRGKLP  PGPTPLPVIG  NILQIGIKDI  SKSLTNLSKV  YGPVFTLYFG
 29c MDPAVALVLC  LSCLFLLSLW  RQSSGRGRLP  SGPTPLPIIG  NILQLDVKDM  SYSLTNFSKU  TGPVGTVYFG
 6b  MDPAVALVLC  LSCLFLLSLQ  RQSSGRGRLP  SGPTPLPIIG  NILQLDVKDM  SKSLTNFSKV  YGPVFTVYFG
 11a MDPFVVLVLC  LSCLLLLSIQ  RQSSGRGKLP  PGPTPLPVIG  NILQIDIKDV  SYSLTNLSKI  YGPVFTLYFG 71                                                                                             140
     lkpiVVlHGY  EaVKEALIDl  GEEFSGRG.f  Plaeran.G.  GIvfSNGKrW  KEIRREsLmt  LRNFGMGKRS
1IC8 MNPIVVFHGY  EAVKEALIDN  GEEFSGRGNS  PISQRITKGL  GIISSNGKRW  KEIRRFSLTN  LTNFGMGKRS
 65  LKPIVVLHGY  EAVKEALIDL  GEEFSGRGIF  PLAERANRGF  GIVFSNGKKW  KEIRRFSLMT  LRNFGMGKRS
 25  LKPIVVLHGY  EAVKEALIDL  GEEFSGRGIF  PLAERANRGF  GIVFSNGKKW  KEIRRFSLMT  LRNFGMGKRS
 29c LKPIVVLHGY  EAVKEALIDL  GEEFSGRGSF  PVAEKVNKGL  GILFSNGKRW  KEIRRFCLMT  LRNFGMGKRS
 6b  LKPIVVLHGY  EAVKEALIDH  GEEFSGRGSF  PVAEKVNKGL  GILFSNGKRW  KEIRRFCLMT  LRNFGMGKRS
 11a LERMVVLHGY  EVVKEALIDL  GEEFSGRGHF  PLAERANRGF  GIVFSNGKRW  KEIRRFSLMT  LRNFGMGKRS 141                                                                                            210
     IEDRVQEEAr  CLVEELRKTk  ASPCDPTFIL  GCAPCNVICS  iiFhkRFDYK  DQqFLnLMek  lNENirIlss
1IC8 IEDRVQEEAH  CLVEELRKTK  ASPCDPTFIL  GCAPCNVICS  VVFQKRFDYK  DQNFLTLMKR  FNENFRILNS
 65  IEDRVQEEAR  CLVEELRKTK  ASPCDPTFIL  GCAPCNVICS  IIFHKRFDYK  DQQFLNLMEK  LNENIKILSS
 25  IEDRVQEEAR  CLVEELRKTK  ASPCDPTFIL  GCAPCNVICS  IIFHKRFDYK  DQQFLNLMEK  LNENIKILSS
 29c IEDRVQEEAR  CLVEELRKTK  ASPCDPTFIL  GCAPCNVICS  VIFHDRFDYK  DQRFLNLMEK  FNENLRILSS
 6b  IEDRVQEEAR  CLVEELRKTN  ASPCDPTFIL  GCAPCNVICS  VIFHDRFDYK  DQRFLNLMEK  FNENLRILSS
 11a IEDRVQEEAR  CLVEELRKTK  ASPCDPTFIL  GCAPCNVICS  IIFQKRFDYK  DQQFLNLMEK  LNENIRIVST
```

```
                                                                                      280
         211
      PWIQiCNNFp .iIDyfPGtH NKllkNvafm kSyilEkvKE HQeSlDmNnp rDFiDCFLiK MEqEkhNQqS
11C8  PWIQVCNNFP LLIDCFPGTH NKVLKNVALT RSYIREKVKE HQASLDVNNP RDFMDCFLIK MEDEKDNQKS
65    PWIQICNNFS PIIDYFPGTH NKLLKNVAFM KSYILEKVKE HQESMDMNNP QDFIDCFLMK MEKEKHNQPS
25    PWIQICNNFS PIIDYFPGTH NKLLKNVAFM KSYILEKVKE HQESMDMNNP QDFIDCFLMK MEKEKHNQPS
29c   PWIQVCNNFP ALIDYLPGSH NKIAENFAYI KSYVLERIKE HQESLDMNSA RDFIDCFLIK MEQEKHNQQS
6b    PWIQVCNNFP ALIDYLPGSH NKIAENFAYI KSYVLERIKE HQESLDMNSA RDFIDCFLIK MEQEKHNQQS
11a   PWIQICNNFP TIIDYFPGTH NKLLKNLAFM ESDILEKVKE HQESMDINNP RDFIDCFLIK MEKEKQNQQN 350
         281
      EFtiEsLiaT vtDlfgAGTE tTSTTLRYaL LLLLKhPEVT AKVQEEIerV iGRnRSPCMQ DRsHMPYTDA
11C8  EFNIENLVGT VADLFVAGTE TTSTTLRYGL LLLLKHPEVT AKVQEEIDHV IGRHRSPCMQ DRSHMPYTDA
65    EFTIESLENT AVDLFGAGTE TTSTTLRYAL LLLLKHPEVT AKVQEEIERV IGRNRSPCMQ DRSHMPYTDA
25    EFTIESLENT AVDLFGAGTE TTSTTLRYAL LLLLKHPEVT AKVQEEIERV IGRNRSPCMQ DRSHMPYTDA
29c   EFTVESLIAT VTDMFGAGTE TTSTTLRYGL LLLLKYPEVT AKVQEEIECV VGRNRSPCMQ DRSHMPYTDA
6b    EFTVESLIAT VTDMFGAGTE TTSTTLRYGL LLLLKYPEVT AKVQEEIECV VGRNRSPCMQ DRSHMPYTDA
11a   EFTIENLVIT AADLLGAGTE STSTTLRYAL LLLLKHPEVT AKVQEEIERV IGRNRSPCMQ DRGHMPYTDA 420
         351
      VVHEvQRYiD LlPTslPHAV TcDvKFrNYL IPKGtTIlts LTSVLHdnKE FPNPemFDPg HFLDegGNEK
11C8  VVHEVQRYSD LVPTGVPHAV TTDTKFRNYL IPKGTTIMAL LTSVLHDDKE FPNPNIFDPG HFLDKNGNFK
65    VVHEVQRYID LLPTSLPHAV TCDIKFRNYL IPKGTTILIS LTSVLHDNKE FPNPEMFDPH HFLDEFFNEK
25    VVHEVQRYID LLPTSLPHAV TCDIKFRNYL IPKGTTILIS LTSVLHDNKE FPNPEMFDPH HFLDEFFNEK
29c   VVHEIQRYID LLPTNLPHAV TCDVKFKNYL IPKGTTIITS LTSVLHDNKE FPNPEMFDPG HFLDKSGNEK
6b    VVHEIQRYID LLPTNLPHAV TCDVKFKNYL IPKGMTIITS LTSVLHNDKE FPNPEMFDPG HELDKSGNEK
11a   VVHEVQRYID LIPTSLPHAV TCDVKFRNYL IPKGTTILTS LTSVLHDNKE FPNPEMFDPR HFLDEGGNFK
```

```
       421                                                                                  491
       KSdYFMPFSA GKRiCvGEgL ArMELFLFLT tILQNFNLKS lvDpKdldtT pvvngfasvP PfYClCFIPV *
  11C8 KSDYFMPFSA GKRICAGEGL ARMELFLFLT TILQNFNLKS VDDLKNLNTT AVTKGIVSLP PSYCICFIPV *
   65  KSKYFMPFSA GKRICVGEGL AGMELFLFLT SILQNFNLKS LVDPKNLDTT PVVNGFASVP PFYCLCFIPV *
   25  KSKYFMPFSA GKRICVGEAL AGMELFLFLT SILONFNLKS LVDPKNLDTT PVVNGFASVP PFYCLCFIPV *
   29c KSDYFMPESA GKRMCMGEGL ARMELFLELT TILONENLKS QVDPKDIDIT PIANAFGRVP PLYCLCFIPV *
   6b  KSDYFMPESA GKRMCMGEGL ARMELFLFLT TILONFNLKS QVDPKDIDIT PIANAFGRVP PLYCLCFIPV *
   11a KSNYFMPFSA GKRICVGEGL ARMELFLFLT FILQNFNLKS LIDPKDLDTT PVVNGFASVP PFYCLCEIPC *
```

FIG. 3-3.

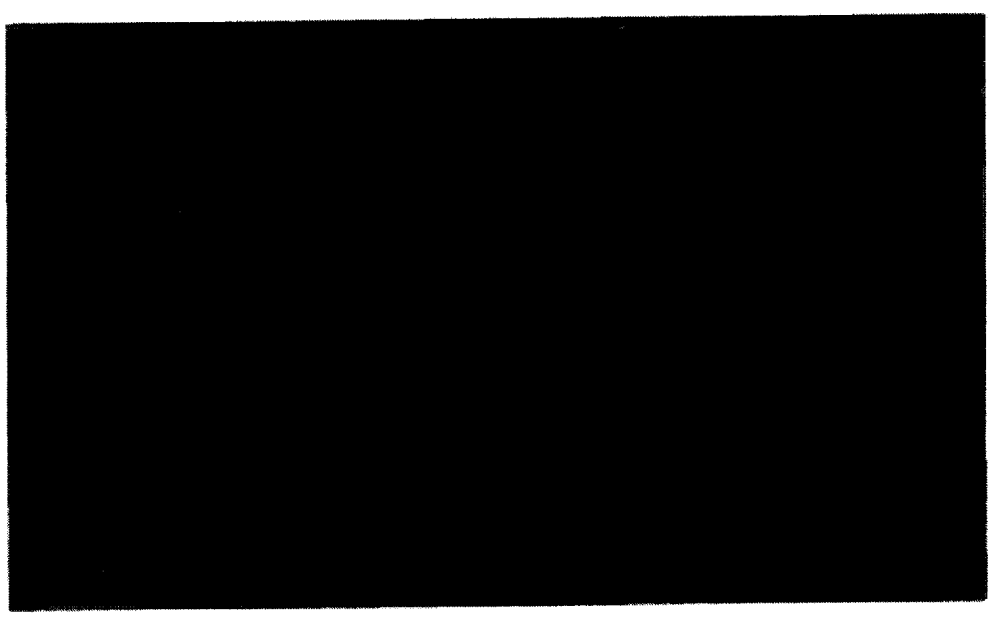
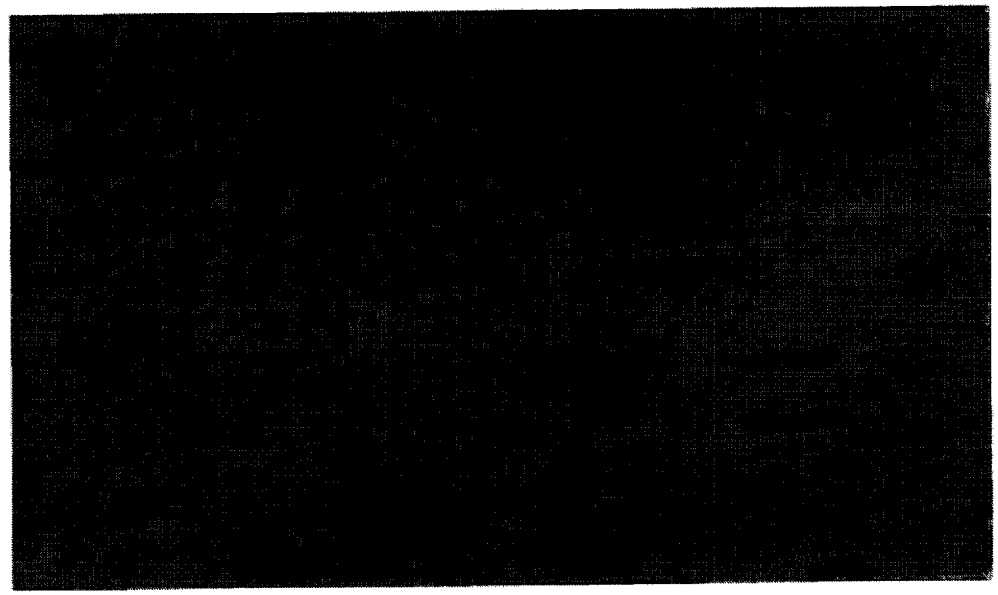
FIG. 4

FIG. 5

FIG. 6
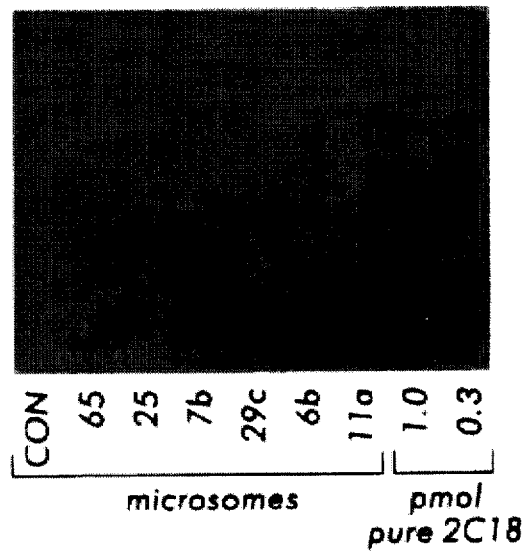
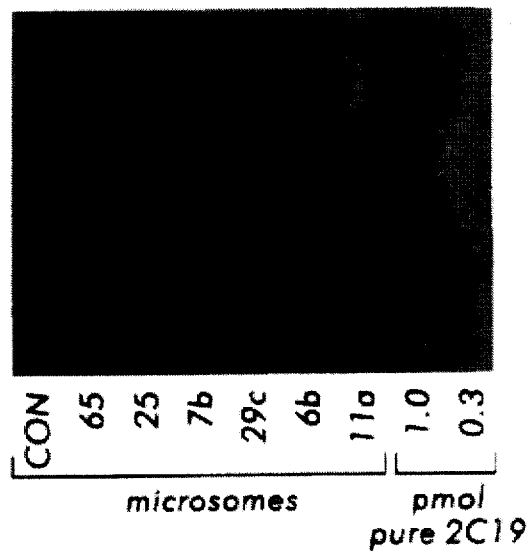
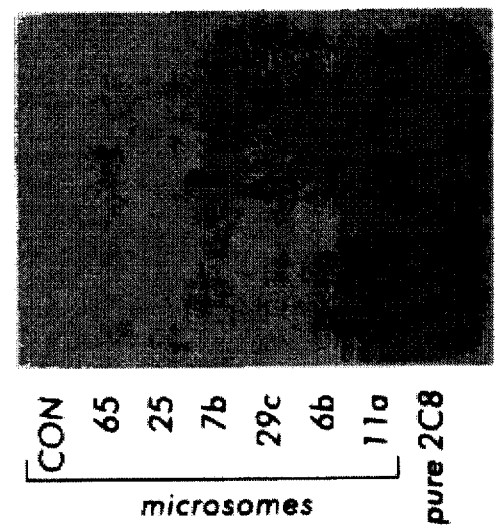
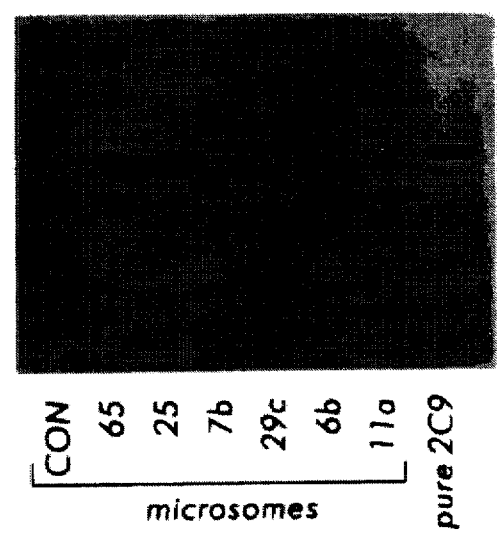

CLONING AND EXPRESSION OF COMPLEMENTARY DNAS FOR MULTIPLE MEMBERS OF THE HUMAN CYTOCHROME P450 2C SUBFAMILY

CROSS-REFERENCE TO RELATED APPLICATION

This application is a continuation-in-part of U.S. Ser. No. 07/864,962, filed Apr. 9, 1992, now abandoned, which is incorporated by reference in its entirety for all purposes.

TECHNICAL FIELD

The present invention relates generally to isolation and exploitation of two novel members of the cytochrome P450 2C subfamily of enzymes designated 2C18 and 2C19.

BACKGROUND OF THE INVENTION

The cytochromes P450 are a large family of hemoprotein enzymes capable of metabolizing xenobiotics such as drugs, carcinogens and environmental pollutants as well as endobiotics such as steroids, fatty acids and prostaglandins. Some members of the cytochrome P450 family are inducible in both animals and cultured cells, while other forms are non-constitutive. This group of enzymes has both harmful and beneficial activities. Metabolic conversion of xenobiotics to toxic, mutagenic and carcinogenic forms is a harmful activity. Detoxification of some drugs and other xenobiotic substances is a beneficial activity (Gelboin, *Physiol. Rev.*, 60:1107-1). A further beneficial activity is the metabolic processing of some drugs to activated forms that have pharmacological activity.

Genetic polymorphisms of P450 enzymes result in phenotypically-distinct subpopulations that differ in their ability to perform particular drug biotransformation reactions. These phenotypic distinctions have importance implications for selection of drugs. For example, a drug that is safe when administered to most human may cause intolerable side-effects in an individual suffering from a defect in a P450 enzyme required for detoxification of the drug. Alternatively, a drug that is effective in most humans may be ineffective in a particular subpopulations because of lack of a P450 enzyme required for conversion of the drug to metabolically active form. Accordingly, it is important for both drug development and clinical use to screen drugs to determine which P450 enzymes are required for activation and/or detoxification of the drug. It is also important to identify individuals who are deficient in a particular P450 enzyme.

A cytochrome P450 polymorphism of particular concern results in reduced levels of S-mephenytoin 4'-hydroxylase activity in certain subpopulations. (Küpfer et al., *Eur. J. Clin. Pharmacol.* 26:753–759 (1984); Wedlund et al., *Clin. Pharmacol. Ther.* 36:773–780 (1984). Two phenotypes, extensive and poor metabolizers, are present in the human population. Poor metabolizers are detected at low frequencies in Caucasians (2–5%) but at higher frequencies in the Japanese population (~20%) (Nakamura et al., *Clin. Pharmacol. Ther.* 38:402–408 (1985); Jurima et al., *Br. J. Clin. Pharmacol.* 19:483–487 (1985) and blacks (~12%). 4'-hydroxylation of S-mephenytoin is 3–10 fold higher than that of the R- enantiomer in extensive metabolizers, but the ratio is approximately 1 or less in poor metabolizers (Yasumori et al., *Mol. Pharmacol.* 35:443–449 (1990). Rates of S-mephenytoin 4'-hydroxylation in liver microsomes are also much higher than those of R-mephenytoin in extensive metabolizers.

There is some evidence that S-mephenytoin 4' hydroxylase activity resides in the cytochrome P450 2C family of enzymes. A number of 2C human variants (designated 2C8, 2C9 and 2C10) have been partially purified, and/or cloned. See Shimada et al., *J. Biol. Chem.* 261:909–921 (1986); Kawano et al., *J. Biochem. (Tokyo)* 102:493–501 (1987); Gut et al., *Biochem. Biophys. Acta* 884:435–447 (1986); Beaune et al., *Biochem Biophys. Acta* 840:364–370 (1985); Ged et al., *Biochemistry* 27:6929–6940 (1988)); Umbenhauer et al., *Biochemistry* 26, 1094–1099 (1987); Kimura et al., *Nucleic Acids Res.* 15:10053–10054 (1987); Shephard et al., *Ann. Humn. Gentc.* 53:23–31 (1989); Yasumori et al., *J. Biochem.* 102:1075–1082 (1987); Relling et al., *J. Pharmacol. Ther.* 252:442–447. A comparison of the P450 2C cDNAs and their predicted amino acid sequences shows that about 70% of the amino acids are absolutely conserved among the human P450 2C subfamily. Some regions of human P450 2C protein sequences have particularly highly conservation, and these regions may participate in common P450 functions. Other regions show greater sequence divergence regions and are likely responsible for different substrate specificities between 2C members.

There has been considerable controversy as to whether any of the known 2C members encodes the principal human determinant of S-mephenytoin 4' hydroxylase activity, in which the polymorphism discussed above presumably resides. The multiplicity and common properties of cytochromes P450 make it difficult to separate their different forms, especially the minor forms. Even in situations where P450 cytochromes have been isolated in purified form by conventional enzyme purification procedures, they have been removed from the natural biological membrane association and therefore require the addition of NADPH-cytochrome P450 reductase and other cell fractions for enzymatic activity.

The known members of the cytochrome P450 2C family exhibit only low-levels of S-mephenytoin 4'-hydroxylase activity, if any. Moreover, such low levels of activity are not specific for the S-enantiomer. For example, when the cDNA isolated by Kimura et al. (1987), supra, was expressed in HepG2 cells, it metabolized racemic and (R)-mephenytoin but had no (S)-mephenytoin hydroxylase activity, suggesting that the polymorphism in the metabolism of (S)-mephenytoin resides in a different member of the 2C family. As a further example, Yasumori et al. (1991), supra, reported that an allelic variant of 2C9 ($Arg^{144}Tyr^{358}Iso^{359}Gly^{417}$) showed a low-level of catalytic activity toward S-mephenytoin in a cDNA-directed yeast expression. However, Srivastava et al., *Mol. Pharmacol.* 40:69—69 (1991) expressed an identical cDNA in yeast and a $Arg^{144}Cys^{358}Iso^{359}Asp^{417}$ variant (2C10 by present nomenclature) but were unable to demonstrate catalytic activity of 2C9 or 2C10 toward S-mephenytoin. Relling et al., *J. Pharmacol. Exper. Ther.* 252:442–447 (1990), were also unable to demonstrate catalytic activity of an allelic variant of $Cys^{144}Tyr^{358}Ile^{359}Gly^{417}$-2C9 toward S-mephenytoin using a retroviral cDNA expression system in HepG2 cells. In contrast, all of these 2C9 variants metabolized tolbutamide in the various expression systems confirming that failure to observe S-mephenytoin 4'-hydroxylase activity was not due to deficiencies in the expression system.

Based on the foregoing, it is apparent that a need exists to identify and isolate the P450 2C family member representing the principal determinant of S-mephenytoin 4'-hydroxylase activity in humans. There is also a need for stable cell lines expressing the S-mephenytoin

3

4'-hydroxylase activity. A need is also apparent for methods of screening drugs for safety and efficacy in individuals deficient in S-mephenytoin 4'-hydroxylase activity. The present invention fulfills these and other needs.

SUMMARY OF THE INVENTION

The invention provides purified cytochrome P450 2C19 polypeptides. The amino acid sequence of an exemplary P450 2C19 polypeptide is designated SEQ. ID. No. 1. Other cytochrome P450 2C19 polypeptides usually comprises an amino acid sequence having at least 97% sequence identity with the exemplified sequence. Many of the 2C19 polypeptides of the invention exhibit stereospecific S-mephenytoin 4'-hydroxylase activity. The activity is typically at least about 1 nmol mephenytoin per nmol of the purified polypeptide per minute.

The invention also provides purified cytochrome P450 2C18 polypeptides. The amino acid sequences of exemplary 2C18 polypeptides are designated SEQ. ID. Nos. 5 and 11.

In another aspect of the invention, purified DNA segments encoding the P450 2C19 polypeptides described above are provided. Some DNA segments encode the exemplary P450 2C19 having the amino acid sequenced designated SEQ. ID. No. 1. One such exemplary DNA segment is designated SEQ. ID. NO. 2. Other DNA segments encode the P450 2C18 polypeptides described above. Exemplary DNA segments are designated SEQ. ID. Nos. 6 and 12.

In a further aspect of the invention stable cell lines are provided. The cell lines comprise an exogenous DNA segment encoding a cytochrome P$%) 2C19 polypeptide having at least 97% sequence identity with the amino acid sequence designated SEQ. ID. No. 1. The DNA segment is capable of being expressed in the cell line. Cell lines preferably produce high levels of the P450 2C19 polypeptide such as 10–200 pmol of the polypeptide per mg of total microsomal protein. Preferred cell lines include yeast and insect cells.

The invention also provides methods of producing a cytochrome P450 2C19 polypeptide. In these methods, a stable cell line, as described above, is cultured under conditions such that the DNA segment contained in the cell line is expressed.

The invention also provides antibodies that specifically bind to a 2C19 polypeptide comprising the amino acid sequence designated SEQ. ID. NO. 1. Preferred antibodies are incapable of binding to nonallelic forms of 2C polypeptides, such as 2C9.

In another aspect, the invention provides methods of screening for a drug that is metabolized by S-mephenytoin 4'-hydroxylase activity. The drug is contacted with a cytochrome P450 2C19 polypeptide. A metabolic product resulting from an interaction between the polypeptide is detected. The presence of the product indicates that the drug is metabolized by the S-mephenytoin 4'-hydroxylase activity. The cytochrome P450 2C19 used in the methods may be substantially pure or may be a component of a lysate of a stable cell line. The cytochrome P450 2C19 polypeptide may also be a component of an intact stable cell line.

The invention also provides methods of identifying a mutagenic, carcinogenic or cytotoxic compound. In some methods, the compound is contacted with a stable cell line capable of expressing a 2C19 polypeptide, such as described above. Mutagenic, carcinogenic or cytotoxic effects of the compound on the cell line are assayed. In other methods, the compound is contacted with a cytochrome P450 2C19 polypeptide in a reaction mixture. A metabolic product is generated resulting from S-mephenytoin 4'-hydroxylase activity on the compound. The metabolic product is assayed for mutagenic, carcinogenic or cytotoxic effects on a test cell line. The effects indicate that the compound is mutagenic, carcinogenic or cytotoxic. In some methods, the test cell line is added to the reaction mixture before, during or after the contacting step. The 2C19 polypeptide used in these methods can be substantially pure or a component of a lysate of a stable cell line. The 2C19 polypeptide can also be a component of an intact stable cell line.

The invention also provides methods for testing the chemopreventive activity of an agent. A stable cell line capable of expressing a 2C19 polypeptide, such as described above, is contacted with an agent suspected of being chemopreventive in the presence of a carcinogen. Effects of the agent on the cell line that are indicative of chemopreventive activity are monitored.

The invention also provides methods for determining the metabolites activated by a carcinogenic or xenobiotic. A stable cell line capable of expressing a 2C19 polypeptide, such as described above, is contacted with the suspected carcinogen or xenobiotic. Metabolites and/or their effects are identified.

The invention also provides methods of detecting a cytochrome 2C19 polypeptide in a tissue sample. The tissue sample is contacted with an antibody that specifically binds to the 2C19 polypeptide preferably without specifically binding to nonallelic variants such as 2C9. Specific binding between the antibody and the polypeptide is detected to indicate the presence of the polypeptide.

BRIEF DESCRIPTION OF THE DRAWINGS

FIG. 3 (Sheets 3-1 to 3-3) depicts a comparison of amino acid sequences of cytochrome P450 2C8 allelic variants.

FIG. 4 depicts a Western blot of recombinant transformed COS-1 cells. Each lane represents microsomal protein (50 µg) from an independent transformation with the indicated P450 2C cDNA, mock-transfected cells (CON), 20 µg of human liver microsomal protein (liver S5), or 2 pmol of pure P450g (2C13).

FIG. 5 shows a Northern blot of human mRNAs. Each lane represents 10 µg of mRNA, and the blot was probed with end-labeled T300R, an oligoprobe specified for 2C8 (SEQ ID NO:8:) (top), stripped, and reprobed with $^{32}$P-actin cDNA (bottom).

FIG. 6: Western blots of yeast microsomes expressing recombinant P450 2C cDNAs. CON=control (yeast microsomes lacking recombinant proteins).

FIG. 10-1 shows Western blots of liver samples from 16 individuals. The lower part of the figure shows the S-mephenytoin 4'-hydroxylation activity and ratios of S/R mephenytoin 4'-hydroxylase activity in each sample.

DEFINITIONS

Figure 7:
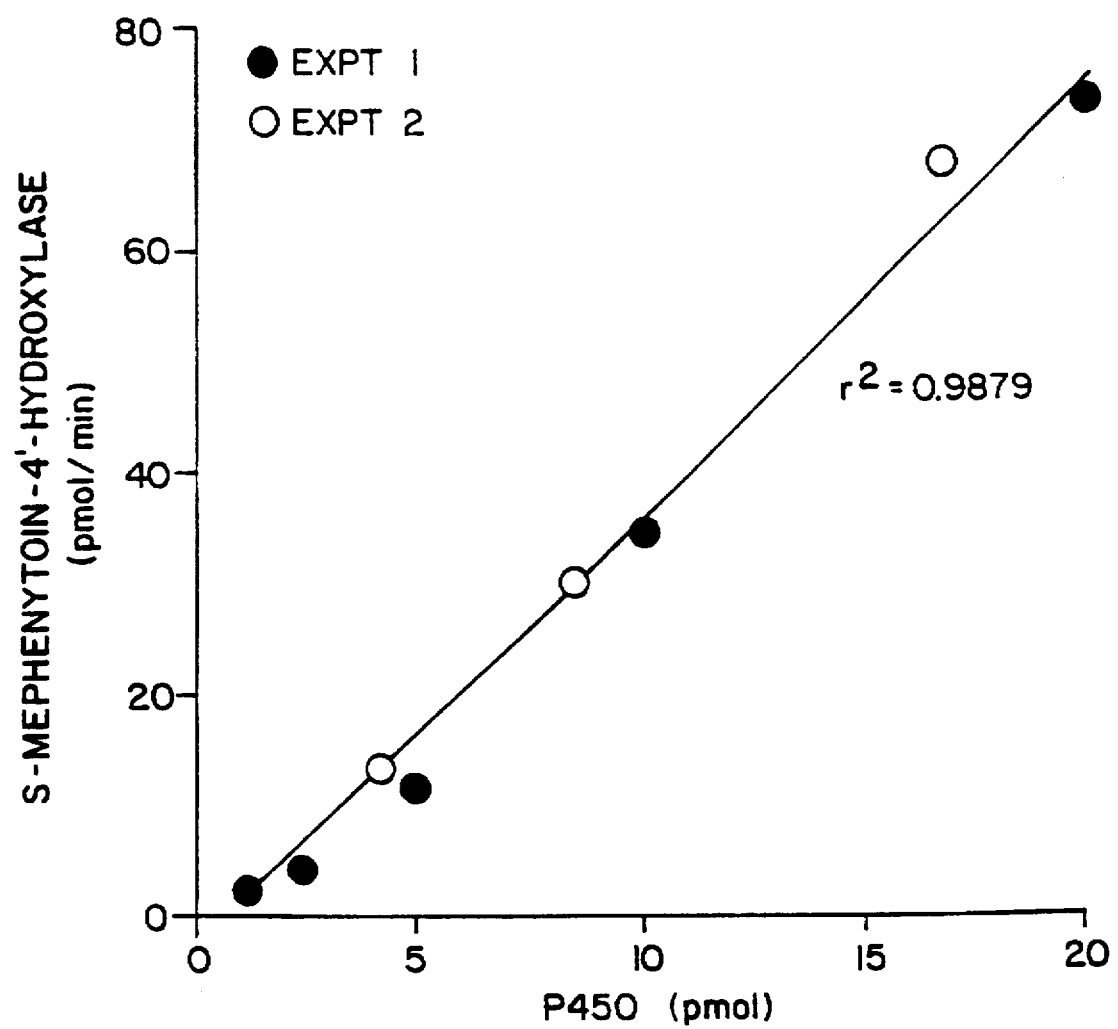
FIG. 7: Linearity of S-mephenytoin 4'-hydroxylase activity and amount of recombinant cytochrome P450 2C19.

Abbreviations for the twenty naturally occurring amino acids follow conventional usage (*Immunology—A Synthesis*, (E. S. Golub & D. R. Gren, eds., Sinauer Associates, Sunderland, Mass., 2nd ed., 1991) (hereby incorporated by reference for all purposes). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N, N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand that are 5' to the 5' end of the RNA transcript are referred to as "upstream sequences"; sequence regions on the DNA strand that are 3' to the 3' end of the RNA transcript are referred to as "downstream sequences".

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence shown in SEQ ID. NO.2 or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci.* (*USA*) 85:2444 (1988), by computerized implementations of these algorithms (FASTDB (Intelligenetics), BLAST (National Center for Biomedical Information) or GAP, BESTFIT, FASTA, and TFASTA (Wisconsin Genetics Software Package Release 7.0, Genetics Computer Group, 575 Science Dr., Madison, Wis.)), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" (also sometimes referred to as "percentage homology") is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 96 percent sequence identity, more usually at least 97, 98 or 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequence of SEQ. ID. Nos. 2, 6 or 12.

As applied to polypeptides, the term "substantial identity" (or "substantial homology") means that two peptide sequences, when optimally aligned, such as by the programs BLAZE (Intelligenetics) GAP or BESTFIT using default gap weights, share at least 85% sequence identity preferably at least 96 percent sequence identity, more preferably at least 97, 98 or 99 percent sequence identity or more (e.g., 99.5 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

Specific binding exists when the dissociation constant for a dimeric complex is $\leq 1$ μM, preferably $\leq 100$ ln and most preferably $\leq 1$ nM.

The term "allelic variants" refers to a gene sequences mapping to the same chromosomal location in different individual in a species but showing a small degree of sequence divergence from each other. Typically, allelic variants encode polypeptides exhibiting at least 96% amino acid sequence identity with each other.

The term "nonallelic variants" refers to gene sequences that show similar structural and/or functional properties but map at different chromosomal locations in an individual. In the 2C family, nonallelic variants typically exhibit 70–96% amino acid sequence identity with each other.

The term "cognate variants" refers to gene sequences that are evolutionarily and functionally related between humans and other species such as primates, porcines, bovines and rodents such as mice and rats. Thus, the cognate primate gene to a human 2C19 gene is the primate gene which encodes an expressed protein which has the greatest degree of sequence identity to the 2C19 protein and which exhibits an expression pattern similar to that of the 2C19 protein.

Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

DESCRIPTION OF THE SPECIFIC EMBODIMENTS

The invention provides novel cytochrome P450 2C polypeptides, DNA fragments encoding these polypeptides and cell lines expressing the polypeptides. The invention also provides methods of using the novel polypeptides for, inter alia, identifying drugs metabolized by S-mephenytoin 4'-hydroxylase activity.

I. Polypeptides

In one embodiment, the invention provides novel cytochrome P450 2C polypeptides, designated 2C18 and 2C19. The 2C18 and 2C19 proteins are nonallelic with each other and with known 2C polypeptides. An exemplary 2C19 polypeptide has the amino acid sequence designated SEQ. ID. No: 1. The invention also provides allelic variants of the exemplified 2C19 polypeptide, and natural and induced mutants of such variants. The invention provides human 2C19 polypeptides and cognate variants thereof. Typically, 2C19 variants exhibit at substantial sequence identity (e.g. at least 96% or 97% amino acid sequence identity) with the exemplified 2C19 polypeptide and cross-react with antibodies specific to this polypeptide. 2C19 variants are usually encoded by nucleic acids that show substantial sequence identity (e.g. at least 96% or 97% sequence identity) with the nucleic acid encoding the exemplified 2C19 variant (SEQ. ID. No:2).

Some 2C19 polypeptides, including the exemplified polypeptide, exhibit high levels of stereospecific S-mephenytoin 4'-hydroxylase activity. See Table IV. Indeed, it is highly probable that 2C19 represents the principal human determinant of this activity. Typically such 2C19 polypeptides exhibit a stereospecific S-mephenytoin 4'-hydroxylase activity of about 0.5–100, 1–10 or about 4–6 nmol S-mephenytoin per nmol 2C19 polypeptide per minute. Frequently, the activity of 2C19 polypeptides is higher than of native human liver microsomes. The activity of such polypeptides for the R-enantiomer of mephenytoin is typically at least 10, 50 or 100-fold lower.

Other 2C19 polypeptides lack substantial stereospecific S-mephenytoin 4'-hydroxylase activity. Such polypeptides represent allelic variants of the exemplified 2C19 polypeptide. These polypeptides sometimes exhibit low levels of mephenytoin 4'-hydroxylase activity (i.e., less than about 0.5 or 0.2 nmol mephenytoin per nmol 2C19 polypeptide per minute). This activity may, or may not be, stereospecific. Although the presence of a 2C19 polypeptide with low enzymic activity could account for the phenotype of a few individuals defective in S-mephenytoin 4'-hydroxylase activity, the phenotype in most such individuals results from a complete or substantial absence of 2C19 polypeptide. See, e.g., FIG. 10.

The invention also provides 2C18 polypeptides. The amino acid sequences of two allelic variants of 2C18 are designated SEQ. ID. Nos: 5 and 11. Also provided are allelic variants of the exemplified 2C18 polypeptides, conjugated variants thereof, and natural and induced mutants of any of these. Typically, 2C18 variants exhibit substantial sequence identity (e.g., at least 96% or 97% amino acid sequence identity) with the exemplified 2C18 polypeptides and cross-react with antibodies specific to these polypeptides. 2C18 variants are usually encoded by nucleic acids that show substantial sequence identity (e.g., at least 96% or 97% sequence identity) with the nucleic acid encoding the exemplified 2C18 variants (SEQ. ID. Nos. 6 and 12).

2C18 polypeptides typically show low levels of mephenytoin 4'-hydroxylase activity (0.01–0.2 nmol mephenytoin per nmol 2C18 polypeptide per min. For some 2C18 polypeptides, the activity shows a small degree of stereoselectivity (up to about five fold). However, by contrast to the 2C19 polypeptides, such stereoselectivity as is shown by 2C18 polypeptides is in favor of the R enantiomer. Some variants of 2C18 show high levels of a distinct enzymic activity, namely, tolbutamide hydroxylase activity (e.g., about 50–200 pmol tolbutamide per nmol 2C18 polypeptide per min). Conceivably, some variants of 2C18 exhibit novel enzymic or regulatory functions not shared by other 2C family members.

Besides substantially full-length polypeptides, the present invention provides fragments of full-length 2C18 and 2C19 polypeptides. Some such fragments share the enzymic activity of a full-length fragment. A segment of a full-length 2C18 or 2C19 polypeptide will ordinarily comprise at least 50 contiguous amino acids and more usually, 100, 200 or 400 contiguous amino acids from one of the exemplified polypeptide sequences, designated SEQ. ID. Nos. 1, 5 and 11. Fragments of full-length 2C18 and 2C19 polypeptides are often terminated at one or both of their ends near (i.e., within about 5, 10 or 20 aa of) the boundaries of functional or structural domains. Fragments are useful for, inter alia, generating antibodies specific to a 2C19 or 2C18 polypeptide. Fragments consisting essentially of the hypervariable regions of these polypeptides are preferred immunoglobulins for generating antibodies specific to a particular allelic variant.

II. Nucleic Acid Fragments

In another aspect of the invention, nucleic acids fragments are provided. An exemplified cDNA sequence of a 2C19 polypeptide is designated SEQ. ID. No. 2. Exemplified cDNA sequences encoding two variant 2C18 polypeptides are designated SEQ. ID. Nos. 6 and 12. The exemplified sequences include both translated regions and 3' and 5' flanking regions. The exemplified sequence data can be used to design probes with which to other DNA fragments encoding 2C18 or 2C19 polypeptides (or fragments thereof). These DNA fragments include human genomic clones, cDNAs and genomic clones from other species, allelic variants, and natural and induced mutants of any of these.

Specifically, all nucleic acid fragments encoding all 2C18 and 2C19 polypeptides disclosed in this application are provided. Genomic libraries of many species are commercially available (e.g., Clontech, Palo Alto, Calif.), or can be isolated de novo by conventional procedures. cDNA libraries are best prepared from liver extracts.

The probes used for isolating clones typically comprise a sequence of about at least 15, 20 or 25 contiguous nucleotides (or their complement) of an exemplified DNA sequence (i.e., SEQ. ID. No. 2, 6 or 12). Preferably probes are selected from regions of the exemplified sequences that show a high degree of variation between different 2C nonallelic variants. Hypervariable regions are the nucleic acids encoding amino acids 181–210, 220–248, 283–269 and 461–479. Probes from these regions are likely to hybridize to allelic variants but not to nonallelic variants of the exemplified sequences under stringent conditions. Allelic variants can be isolated can be isolated by hybridization screening of screening plaque lifts (Benton & Davis, *Science* 196:180 (1978). Alternatively, cDNAs can be prepared from liver mRNA by polymerase chain reaction (PCR) methods. 5'- and 3'- specific primers for 2C19 are designed based on the nucleotide sequence designated SEQ. ID. No. 2. See generally *PCR Technology: Principles and Applications for DNA Amplification* (ed. H. A. Erlich, Freeman Press, N.Y., N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert et al., *PCR Methods and Applications* 1:17 (1991); *PCR* (eds. McPherson et al., IRL Press, Oxford); and U.S. Pat. No. 4,683,202 (each of which is incorporated by reference for all purposes).

Nucleotide substitutions, deletions, and additions can be incorporated into the polynucleotides of the invention. Nucleotide sequence variation may result from degeneracy of the genetic code, from sequence polymorphisms of 2C18 and 2C19 alleles, minor sequencing errors, or may be introduced by random mutagenesis of the encoding nucleic acids using irradiation or exposure to EMS, or by changes engineered by site-specific mutagenesis or other techniques. See Sambrook et al., *Molecular Cloning: A Laboratory Manual* (C.S.H.P. Press, NY 2d ed., 1989) (incorporated by reference for all purposes).

III. Cell Lines

In another embodiment of the invention, cell lines capable of expressing the nucleic acid segments described above are provided. Stable cell lines are preferred to cell lines conferring transient expression. Stable cell lines can be passaged at least fifty times without reduction in the level of 2C polypeptides expressed by the cell lines. Preferably, cell lines are capable of being cultured so as to express 2C polypeptides at high levels, usually at least 0.2, 1, 10, 20, 50, 100, 200 or 500 pmol of 2C polypeptide per mg of microsomal protein. For example, the 2C19 expression level of many cell lines of the invention is typically about 0.2–10, 000, 1–200, 7–100, 10–50 or 10–20 pmol 2C19 polypeptide per mg microsomal protein. An expression level of 10 pmol 2C19 per mg microsomal protein means that 2C19 represents about 0.06% of total cellular protein. For *E. coli* and insect cell lines, the recombinant P450 protein can comprise 5–10% of total cellular protein. Often, the stable cell lines of the invention express more than one P450 polypeptide. These cell lines express 2C18 and/or 2C19 together with other members of the 2C family, or other P450 cytochromes such as 1A1, 1A2, 2A6, 3A3, 3A4, 2B6, 2B7, 2C9, 2D6, and/or 2E1.

*E. coli* is one prokaryotic host useful for cloning the polynucleotides of the present invention. Other microbial hosts suitable for use include bacilli, such as *Bacillus subtilus*, and other enterobacteriaceae, such as Salmonella, Serratia, and various Pseudomonas species. Expression vectors typically contain expression control sequences compatible with the host cell, e.g., an origin of replication, any of a variety of well-known promoters, such as the lactose promoter system, a tryptophan (trp) promoter system, a beta-lactamase promoter system, or a promoter system from phage lambda. Vectors often also contain an operator sequence and/or a ribosome binding site. The control sequences are operably linked to a P450 DNA segment so as to ensure its expression and control the expression thereof.

Other microbes, such as fungi, particularly, yeast, are particularly useful for expression. Saccharomyces is a preferred host, with suitable vectors having expression control sequences, such as promoters, including 3-phosphoglycerate kinase or other glycolytic enzymes, and an origin of replication, termination sequences and the like as desired. For example, the plasmid pAAH5 can be used. The 5'-noncoding sequence of the P450 2C cDNAs can be eliminated and six adenosines added by polymerase chain reaction (PCR) amplification to optimize expression in yeast cells. The 5'- and 3'-primers recommended for amplification of 2C18 are 5'-GCAAGCTTAAAAAATGGATCCAGCTG TGGCTCT-3' (SEQ ID NO:15:) and 5'-GCAAGCTTGCC AAACTATCTGCCCTTCT-3' (SEQ ID NO:16:). This includes addition of a Hind III restriction site at both ends to allow insertion into the pAAH5 vector and six 6 adenosines at the 5'-end to optimize translation. The final 20 bases of each sequence is specific for 20 bases at the 5'-end of 2C18 starting with the ATG for methionine and 20 bases of the 3'-noncoding region. The primers for 2C19 can be constructed similarly. The yeast strain used, *Saccharomyces cerevisiae* 334, can be propagated non-selectively in YPD medium (1% yeast extract, 2% peptone, 2% dextrose (Hovland et al. (1989) *Gene* 83, 57–64) and Leu+ transformants selected on synthetic minimal medium containing 0.67% nitrogen base (without amino acids), 0.5% ammonium sulfate, 2% dextrose and 20 µg/ml L histidine (SD+ His). Plates are made by the addition of 2% agar. Yeast can be transformed by the lithium acetate method of Ito et al. (1983) *J. Bacteriol.* 153, 163 and selected on SD+His for selection of transformants. Cells are then grown to mid-logarithmic phase (Oeda et al., *DNA* 4:203–210 (1985)) and microsomes containing recombinant protein can be prepared.

Insect cells (e.g., SF9) with appropriate vectors, usually derived from baculovirus, are also suitable for expressing 2C polypeptides. See Luckow, et al. *Bio/Technology* 6:47–55 (1988) (incorporated by reference for all purposes).

Mammalian tissue cell culture can also be used to express and produce the polypeptides of the present invention (see Winnacker, *From Genes to Clones* (VCH Publishers, N.Y., N.Y., 1987). Suitable host cell lines include CHO cell lines (e.g., V79) (Dogram et al. (1990) *Mol. Pharmacol.* 37, 607–613), various COS cell lines, HeLa cells, myeloma cell lines and Jurkat cells, hepatoma cell lines (Hep G2), and a lymphoblastoid cell line AHH-1 TK+/−. Crespi et al. (1991) *Carcinogenesis* 12, 355–359. Expression vectors for these cells (e.g., pEBVHistK or pSV2) can include expression control sequences, such as an origin of replication, a promoter (e.g., a HSV tk promoter or pgk (phosphoglycerate kinase promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Preferred expression control sequences are promoters derived from immunoglobulin genes, SV40, adenovirus, bovine papillomavirus, and the like. Expression control sequences are operably linked to a DNA segment encoding a P450 polypeptide so as to ensure the polypeptide is expressed.

The vectors containing the polynucleotide sequences of interest can be transferred into the host cell by wellknown methods, which vary depending on the type of cellular host. For example, calcium chloride transfection is commonly utilized for prokaryotic cells, whereas calcium phosphate treatment or electroporation may be used for other cellular hosts. (See generally Sambrook et al., *Molecular Cloning: A Laboratory Manual* (Cold Spring Harbor Press, 2nd ed., 1989) (incorporated by reference in its entirety for all purposes).

Once expressed, the polypeptides of the invention and their fragments can, if desired, be purified according to standard procedures of the art, including ammonium sulfate precipitation, affinity columns, column chromatography, gel electrophoresis and the like (see generally Scopes, *Protein Purification* (Springer-Verlag, N.Y., 1982).

IV. Antibodies

The invention also provides antibodies that specifically bind to epitopes on the 2C18 and 2C19 polypeptides of the invention. Some antibodies specifically bind to one member of the 2C family (e.g., 2C19) without binding to nonallelic forms. Some antibodies specifically bind to a single allelic form of a 2C member such as the 2C19 polypeptide having the amino acid sequence designated SEQ. ID. No: 1. Antibodies that specifically bind to a 2C19 polypeptide without binding to a 2C9 polypeptide are particularly useful in view of the relatively high degree of sequence identity between these nonallelic variants. See Table II. The production of non-human monoclonal antibodies, e.g., murine, lagomorpha, equine is well known and can be accomplished by, for example, immunizing an animal with a preparation containing a 2C19 polypeptide or an immunogenic fragment thereof. Human antibodies can be prepared using phage-display technology. See, e.g., Dower et al., WO 91/17271 and McCafferty et al., WO 92/01047 (each of which is incorporated by reference in its entirety for all purposes). Humanized antibodies are prepared as described by Queen et al., WO 90/07861.

V. Methods of Use (1) Identification of Drugs Unsuitable for Administration to Poor Metabolizers of S-Mephenytoin The identification of a 2C19 polypeptide as the principal determinant of human S-mephenytoin 4'-hydroxylase activity facilitates methods of screening drugs that are metabolized by this enzyme. Such drugs likely lack efficacy and/or show intolerable side effects in individuals having a defect in S-mephenytoin 4'-hydroxylase activity (low producers). The substantial absence of this activity in low producers often results in an inability to detoxify such drugs, preventing their elimination from the body. Substantial absence of S-mephenytoin 4'-hydroxylase activity can also prevent metabolic processing of certain drugs to activated forms. Drugs suspected of being metabolized by S-mephenytoin 4'-hydroxylase activity include, in addition to mephenytoin itself, omeprazole, proguanil, diazepam and certain barbiturates.

Drugs are screened for metabolic processing by S-mephenytoin 4'-hydroxylase activity in a variety of assays. See Example 5. In brief, the drug under test is usually labelled with a radioisotope or otherwise. The drug is then contacted with a 2C19 polypeptide exhibiting S-mephenytoin 4'-hydroxylase activity (e.g., the polypeptide designated SEQ. ID. NO: 1). The 2C19 polypeptide can be in purified form or can be a component of a lysate of one of the cell lines discussed in Section III. Often, the 2C19 polypeptide is part of a microsomal fraction of a cell lysate. The 2C19 polypeptide can also be a component of an intact cell as many drugs are taken up by such cells. Often, the reaction mixture is supplemented with one or more of the following reagents: dilauroylphosphatidylcholine, cytochrome P450 reductase, human cytochrome b5, and NADPH. (See Example 5, for concentrations of these reagents and a suitable buffer). After an incubation period (e.g., 30 min), the reaction is terminated, and centrifuged. The supernatant is analyzed for metabolic activity, e.g., by a spectrographic or chromatographic method. The assay is usually performed in parallel on a control reaction mixture without a 2C19 polypeptide. Metabolic activity is shown by a comparative analysis of supernatants from the test and control reaction mixtures. For example, a shift in retention time of radiolabelled peaks between test and control under HPLC analysis indicates that the drug under test is metabolized by S-mephenytoin 4'-hydroxylase activity. Often, the test is repeated using an extract from human liver in place of the 2C19 polypeptide. The appearance of a labelled metabolic peak from the reaction using 2C19 recombinant organisms or 2C19 recombinant cell fractions having the same HPLC retention time, and a specific activity at least as high, as that observed for human liver microsomes provides strong evidence that S-mephenytoin 4-hydroxylase activity plays a major role in processing the drug. The test can also be repeated using other 2C members, such as 2C18, as controls, in place of 2C19.

Drugs can also be screened for metabolic dependence on S-mephenytoin 4'-hydroxylase activity in transgenic nonhuman animals. Some such animals have genomes comprising a 2C19 transgene (e.g., SEQ. ID. No: 2) operably linked to control sequences so as to render the transgene capable of being expressed in the animals. Other transgenic animals have a genome containing homozygous null mutations of endogenous 2C19 genes. Mice and other rodents are particular suitable for production of transgenic animals. Drugs are administered to transgenic animals in comparison with normal control animals and the effects from administration are monitored. Drugs eliciting different responses in the transgenic animals than the control animals likely require S-mephenytoin 4'-hydroxylase activity for detoxification and/or activation.

Drugs identified by the above screening methods as being metabolized by S-mephenytoin 4'-hydroxylase activity should generally not be administered to individuals known to be deficient in this enzyme, or should be administered at different dosages. Indeed, in the absence of data on an individual patient's S-mephenytoin 4-hydroxylase phenotype, it is often undesirable to administer such drugs to any member of an ethnic group known to be at high risk for S-mephenytoin 4-hydroxylase deficiency (e.g., Japanese and blacks). If it is essential to administer drugs identified by the above screening procedures to individuals known to be at risk of enzymic deficiency (e.g., no alternative drug is available), a treating physician is at least apprised of a need for vigilant monitoring of the patient's response to the drug. In general, the identification of a new drug as a substrate for 2C19 would mitigate against further development of the drug.

(2) Screening Compounds for Mutagenic, Cytotoxic or Carcinogenic Activity

The invention provides methods of measuring the mutagenic, cytotoxic or carcinogenic potential of a compound. In some methods, mutagenic, cytotoxic or carcinogenic effects are assayed directly on a cell line harboring one or more recombinant cytochrome P450 enzymes. In these methods, a compound under test is added to the growth medium of a cell line expressing 2C19, and/or 2C18 and/or other cytochrome P450s. Often, one or more of the reagents discussed in Section V(I), supra, is also added. After a suitable incubation, mutagenic, cytotoxic or carcinogenic effects are assayed. Mutagenic effects are assayed, e.g., by detection of the appearance of drug-resistant mutant cell colonies (Thompson, *Methods Enzymol.*, 58:308, 1979). For example, mutagenicity can be evaluated at the hgprt locus (Penman et al., (1987) *Environ. Mol. Mutagenesis* 10, 35–60). Cytotoxicity can be assayed from viability of the cell line harboring the P450 enzyme(s). Carcinogenicity can be assessed by determining whether the cell line harboring the P450 enzymes has acquired anchorage-independent growth or the capacity to induce tumors in athymic nude mice.

In other methods, a suspected compound is assayed in a selected test cell line rather than a cell line harboring P450 enzymes. In these methods, the compound under test is contacted with P450 2C19 and/or 2C18 and/or other P450 enzymes. The P450 enzyme(s) can be provided in purified form, or as components of lysates or microsomal fractions of cells harboring the recombinant enzyme(s). The P450 enzyme(s) can also be provided as components of intact cells. Usually, one or more of the reagents discussed in Section V(1), supra is also added. Optionally, the appearance of metabolic products from the suspected compound can be monitored by techniques such as thin layer chromatography or high performance liquid chromatography and the like.

The metabolic products resulting from treatment of the suspected compound with P450 enzyme(s) are assayed for mutagenic, cytotoxic or carcinogenic activity in a test cell line. The test cell line can be present during the metabolic activation of the mutagen or can be added after activation has occurred. Suitable test cell lines include a mutant strain of *Salmonella typhimurium* bacteria having auxotrophic histidine mutations (Ames et al., *Mut. Res.* 31:347–364 (1975). Other standard test cell lines include chinese hamster ovary cells (Galloway et al., *Environ. Mutagen.* 7:1 (1985); Gulati et al., (*Environ. Mol. Mutagenesis* 13:133–193 (1989)) for analysis of chromosome aberration and sister chromatic exchange induction, and mouse lymphoma cell (Myhr et al., *Prog. Mut. Res.* 5:555–568, (1985)).

The use of defined P450 enzymes for activation of compounds in the present methods offers significant advantages over previous methods in which rat or human S9-supernatant liver fractions (containing an assortment of P450 enzymes) were used. The present methods are more reproducible and also provide information on the mechanisms by which mutagenesis, cytotoxicity and carcinogenicity are effected.

(3) Identification of Potential Chemopreventive Drugs

The invention also provides methods for identifying drugs having chemopreventive activity. These methods employ similar procedures to those discussed in paragraph (2) above except that the methods are performed using a known mutagenic, cytotoxic or carcinogenic agent, together with a suspected chemopreventive agent. Mutagenic, cytotoxic or carcinogenic effects in the presence of the chemopreventive agents are compared with those in control experiments in which the chemopreventive agent is omitted.

(4) Screening for Potential Chemotherapeutic Drugs

The invention provides analogous methods to those described in paragraph (2), supra, for screening chemotherapeutic agents. In some methods, chemotherapeutic activity is determined directly on a tumorigenic cell line expressing 2C19 and/or 2C18 and or other cytochrome P450 enzymes. In other methods, chemotherapeutic activity is determined on a tumorigenic test cell line. Chemotherapeutic activity is evidenced by reversion of the transformed phenotype of cells resulting in reduced 50 bb agar growth or reduced tumor formation in nude mice.

(5) Programmed Cell Death.

The invention provides analogous methods to those described in paragraph (2), supra, for identifying agents that induce programmed cell death or apoptosis. Apoptosis may have an important impact on prevention of malignant transformation. Programmed cell death is assayed by DNA fragmentation or cell-surface antigen analysis.

(6) Monitoring 2C18 and 2C19 Polypeptides

The invention provides methods of quantitating the amount of the specific protein in mammalian tissues by measuring the complex formed between the antibody and proteins in the tissue. For example, a biological sample is contacted with an antibody under conditions such that the antibody binds to specific proteins forming an antibody:protein complex which can be quantitatively detected.

VI. Diagnosing 2C19 and 2C18 Polymorphisms

The present invention also relates to diagnostic assays for use in human and veterinary medicine. Identification of the presence or absence of a gene or its mRNA can allow the diagnosis of the P450 2C protein phenotype of an individual and thereby predict her ability to metabolize drugs or mutagens. Sequence information about 2C18 and 2C19 can be used to select specific primers for the specific 2C18 and 2C19 mRNAs and DNAs. Specifically, when defects in 2C19 that result in the poor metabolizing phenotype are known, specific 2C19 primers can be selected to identify such defects. Some of these primers can be obtained from the cDNA sequence. The primers can be used to detect the presence of mRNA or genomic DNA by Southern blotting or PCR. (See Murphy et al., *Biochemistry* 29:10351–10356 (1990); Kogan et al., *New Engl. J. Med.* 314:985–990 (1987)).

The following examples are provided to illustrate but not to limit the invention.

EXAMPLES

Materials. Human liver samples were obtained from organ donors through the National Disease Research Interchange in Philadelphia, Pa., and from the Human Liver Research Facility, Stanford Research Institute, Life Sciences Division, Menlo Park, Calif. Restriction endonucleases were purchased form Pharmacia LKB Biotechnology, Inc. (Piscataway, N.J.). [α-$^{33}$] dCTP (3000 Ci/mmol) and [τ-$^{32}$P] ATP (500 Ci/mmol) and [α-$^{32}$S] dATP (650 Ci/mmol) were from Amersham Corp. (Arlington Heights, Ill.). All other reagents were of the highest quality available.

Conditions. Hybridization and washing conditions for screening libraries with random-labeled cDNAs for 2C13(g) or 254c used the same solutions as described for actin, but were performed at nonstringent temperatures (42° C.). Conditions for hybridization of clones with T300R were identical with those described above. Hybridization of cDNA clones with M300R (recognizes 2C9, 2C10, and 2C19) (5'-ACTTTTCAATGTAAGCAAAT-3') (SEQ ID NO:17:) was identical except that for each oligomer the hybridization temperature and the high-stringency wash were 5° C. below the calculated melting temperatures.

Example 1

Construction and Screening of Human Liver cDNA Libraries

Two cDNA libraries were constructed from human livers 860624 and S33, which differed phenotypically in the hepatic content of P450 HLx (2C8) (SEQ ID NO:8:). Several partial cDNA clones were found but no full-length clones.

A second cDNA library (from a liver phenotypically high in HLx) was then screened. Eighty-three essentially full-length (>1.8 kb) clones belonging to the 2C subfamily were isolated from this library. These include full-length clones for two additional new members of the 2C subfamily.

The majority of the cDNAs characterized in the high-HLx library (60%) were one of two allelic variants of 2C9, while 35%represented 2C8 (SEQ ID NO:8:). Two new genes were identified (two allelic variants of 2C18 and 2C19).

The two cDNA libraries from individuals phenotypically high and low in HLx were examined to determine whether a variant mRNA for 2C8 (SEQ ID NO:8:). was responsible for the polymorphic expression of HLx and to identify additional members of the 2C subfamily. No clones for C8 (SEQ ID NO:8:) were isolated from the individual phenotypically high individual. Two allelic variants for 2C9 were isolated. In addition, full-length cDNAs for two additional new members (2C18 and 2C19) were isolated. These new members of the 2C subfamily were expressed in COS-1 cells and shown to be immunochemically distinct from HLx and 2C9, and 2C18 metabolized racemic mephenytoin.

Total human liver RNA was prepared by the guanidine hydrochloride method (Cox; *Methods Enzymol.* 12:120–129 (1968)) from two human livers either low (860624) or high (S33) in HLx as identified by immunoblot analysis. Poly (A+)RNA was then isolated by two passages over an oligo (dT)-cellulose column (Aviv et al., *Proc. Natl. Acad. Sci. U.S.A.* 69:1408–1412 (1972)). The low-HLx cDNA library was prepared by Stratagene Cloning systems (La Jolla, Calif.), and the double-stranded cDNA was treated with S1 nuclease. Following the addition of EcoRI linkers, the double-stranded cDNA was size-fractionated on a CL-4B Sepharose column. the largest fraction was ligated into λZAPII and then transfected into XL1-Blue. The high-HLx cDNA library was constructed following the methods of Watson et al., in *DNA Cloning* (Glover, D. M., Ed.) 1:79–88, IRL Press, Washington, D.C. (1985)). Double-stranded cDNA was ligated to EcoRI linkers, size-fractionated on an agarose gel (1.8–2.4 kb), and then ligated into λZAPII (Stratagene) and transfected into XL1-Blue.

The low-HLx library was screened under conditions of low stringency with a $^{32}$P-labeled rat P450 2C13 cDNA probe and with oligonucleotides for human 2C8 (SEQ ID NO:8:) (T300R) (5'-TTAGTAATTCTTTGAGATAT-3') (SEQ ID NO:18) and 2C9 (M300R) (5'-CTGTTAGCTCTTTCAGCCAG-3')(SEQ ID NO:19:). the high-HLx library was screened under conditions of low stringency using a $^{32}$P-labeled 254C cDNA probe derived from the first library and M300R (2C9). Positive clones were isolated, transfected into XL1-Blue, and excised into the plasmid Bluescript, according to Stratagene's excision protocol.

Screening the cDNA library constructed from a low-HLx individual with a cDNA for rat 2C13 under nonstringent conditions and with oligonucleotide probes specific for 2C8 (SEQ ID NO:8:) and 2C9 yielded several clones for 2C9 and a partial DNA, clone 254c, which now appears to be an incompletely characterized splice variant of the P450 21C subfamily. None of the clones identified in this library were full-length. Clone 186 was identical with but 25 base pairs longer than MP-4, a 2C9 clone previously described by Ged et al. (1988).

Approximately 40000 plaques were then screened from the library from liver S33)with the cDNA for 254c under non-stringent conditions and with an oligonucleotide probe specific for 2C9. Eighty-three essentially full-length 2C clones (>1.8 kb) were isolated, purified, and partially or completely sequenced (Table I). Of these, 29 clones were found to encode cytochrome P450 2C8 (SEQ ID NO:8:). One clone (7b) of 2C8 (SEQ ID NO:8:) was isolated which was similar to Hpl-1 and Hpl-2 reported by Okino et al. (1987), but different by having a tyrosine at position 130 instead of an asparagine and an isoleucine at 264 instead of a methionine.

TABLE I

Distribution of P450 2C cDNA Clones from Human Liver S33*

|  | No. of Clones | % Distribution |
|---|---|---|
| 2C8 (SEQ ID NO:8:) | 29 | 35 |
| 2C9 |  |  |
| 65 (SEQ ID NO:10:) | 39 | 47 |
| 25 (SEQ ID NO:4:) | 11 | 13 |
| 2C10 | 0 | 0 |
| 2C18 |  |  |
| 29c (SEQ ID NO:6:) | 1 | 1.2 |
| 6b (SEQ ID NO:12:) | 2 | 2.5 |
| 2C19 (11A)(SEQ ID NO:2:) | 1 | 1.2 |
| Total | 83 | 100 |

*Clones were classified by hybridization with specific oligonucleotide probes and partial sequencing.

There are a number of polymorphisms in the human CYP2C subfamily. These include variations in the hepatic levels of HLx (Wrighton et al., Arch. Biochem. Biophys. 306:240–245 (1987)) and metabolic variations in the hepatic metabolism of (S)-mephenytoin. The molecular basis for these polymorphisms has not been characterized. 2C8 (SEQ ID NO:8:) appears to encode the protein for HLx on the basis of its N-terminal amino acid sequence (Okino et al., J. Biol. Chem. 262:16072–16079 (1987); Wrighton et al., supra; Lasker et al., Biochem. Biophys. Res. Commun. 148:232–238 (1987)).

Example 2

Sequence Analysis

The Bluescript plasmids containing the positive cDNA inserts from the low-HLx library were purified by CsCl gradients, while the plasmids containing cDNA inserts from the high-HLx library were purified by using Qiagen plasmid purification kits (Qiagen, Inc., Studio city, Calif.). The double-stranded cDNA inserts were sequenced by the dideoxy chain termination method reported in Sanger et al., J. Mol. Biol. 162:729–773 (1982), using Sequenase kits (U.S. Biochemical Corp., cleveland, Ohio). The full-length clones 65 (SEQ ID NO:10:), 25 (SEQ ID NO:4:), 7b, 11a (SEQ ID NO:2:), 29c (SEQ ID NO:6:) and 6b (SEQ ID NO:12:) were sequenced completely in both directions with primers spaced approximately 20 bases apart. The remaining positive clones from the high-HLx cDNA library were sequenced in both directions through both the 5' and 3' ends and through all the regions which would identify any of the known allelic variants.

The majority of the clones (50) isolated from the library from liver S33)coded for 2C9. Interestingly, all of the 50 clones appeared to be 1 of 2 2C9 allelic variants, typified by the full-length clones 65 (SEQ ID NO:10:) and 25 (SEQ ID NO:4:). All of these clones were sequenced through the 5' and 3' ends and through regions which would identify known allelic variants. Thirty-nine of the 2C9 clones were identical with clone 65 (SEQ ID NO:10:) and 25 (SEQ ID NO:4:), all of these clones were sequenced through the 5' and 3' ends and through regions which would identify known allelic variants. Thirty-nine of the 2C9 clones were identical with clone 65 (SEQ ID NO:10:), and 11 were identical with clone 25 (SEQ ID NO:10:), and 11 were identical with clone 25 (SEQ ID NO:4:). The nucleotide sequence for clone 65 (SEQ ID NO:10:) and clone 25 (SEQ ID NO:4:) is shown in FIG. 2. Clones 25 (SEQ ID NO:4:) and 65 (SEQ ID NO:10:) were identical in the 5'- and 3'-noncoding regions but contained two single-base changes at positions 1075 and 1425. One of these base changes was conservative, but the second would result in one amino acid difference at position 359 (isoleucine versus leucine). clone 65 (SEQ ID NO:9:) is identical in amino acid sequence with human form 2, although it differs by two silent changes in the coding region and four differences in the noncoding region (Yasumori et al., 1987). Clone 65 (SEQ ID NO:9:) contained a leucine instead of a isoleucine at position 4, a valine instead of a serine at position 6, and an arginine instead of a cysteine at position 144 compared to the 2C9 sequenced by Kimura et al. (1987). The 2C9 reported by Meehan et al. has substitutions at positions 144, 175, and 238 compared to the clones obtained in this invention (Meehan et al., Am J Hum Genet, 42:26–37 (1988)).

The remaining clones characterized from the human liver S33)cDNA library encode several novel P450 2C cDNAs. Their DNA sequences are shown in FIG. 2 and their percent homology with other known 11c members shown in Table II. Two of these clones, 29c (SEQ ID NO:6:) and 6b (SEQ ID NO:12:), differ by one nucleotide in the coding region (position 1154), which would result in a single amino acid change (threonine vs methionine at position 385). Clone 29c (SEQ ID NO:6:) had a very long (198 bp) 5'-noncoding sequence and a polyadenylation signal 21 bases from the poly (A) tail. Clone 6b (SEQ ID NO:12:) had an unusually long 3'-noncoding region containing three possible polyadenylation signals with no poly(A) tail. The differences in the 3'-noncoding region could represent alternate splicing, allelic variants, or possibly separate genes. However, these clones are designated as allelic variants of (2C18) because they differ by only one base in the coding region. they are most similar to 2C9 (82% amino acid homology) and 2C19 (SEQ ID NO:2:) (81% amino acid homology) (Table II).

A third unique P450 2C cDNA, clone 11a (SEQ ID NO:2:) (designated 2C19), was also identified. 2C19 is 92% homologous in its amino acid sequence to 2C9, 81% homologous to 2C18, and 79% homologous to 2C8 (SEQ ID NO:8:). Clone 11a (SEQ ID NO:2:) had a short 5'-leader sequence and contained the stop codon, but did not have a polyadenylation signal or poly(A) tail. Interestingly, no clones for 2C10 (MP-8) were isolated from either library, despite the sequencing of the 3' region of all 50 putative 2C9 clones.

TABLE II

Percent Homology for Nucleotide and Amino Acid Sequences of P450 2C cDNAs*

| Clone | 2C8 (SEQ ID NO:8:) | 2C9 | 29c (SEQ ID NO:6:) (2C18) | 11a (SEQ ID NO:2:) (2C19) |
|---|---|---|---|---|
| 29c (2C18) | 81 | 85 | 100 | 82 |

TABLE II-continued

Percent Homology for Nucleotide and Amino Acid Sequences of P450 2C cDNAs*

| Clone | 2C8 (SEQ ID NO:8:) | 2C9 | 29c (SEQ ID NO:6:) (2C18) | 11a (SEQ ID NO:2:) (2C19) |
|---|---|---|---|---|
| (SEQ ID NO:6:) | 77 | 82 | 100 | 81 |
| 11a (2C19) | 81 | 90 | 82 | 100 |
| SEQ ID NO:2:) | 79 | 92 | 81 | 100 |

*For each comparison, the upper value represents percent nucleotide homology, and the lower value represents percent amino acid homology. the nucleic acid comparisons include both the coding and non-coding regions. the 2C9 sequence used in this comparison was the cDNA sequence for human form 2 (Yasumori et al., J. Biochem. 102:1075–1082 1987).

FIG. 4 shows the alignment comparisons for the deduced amino acid sequences of all known members of the human CYP2C family, including the three new P450s of the present invention. the 7 proteins, along with the consensus sequence, can be aligned with no gaps, and each is predicted to be 490 amino acids long. the amino acid sequences show marked similarities with many regions of absolute conservation. Regions of marked conservation are noted form 131 to 180, and from 302 to 460. These human P450 2C protein sequences also demonstrate hypervariable regions which may be important for interactions between the enzyme and substrate. these include the region from 181–120 and 220–248 as well as 283–296 and a short region near the carboxyl terminus at 461–479. Notably, it has been reported that a putative recognition site for phosphorylation of P450 by cAMP-dependent kinase for P450 2B1 (Arg-Arg-Phe-Ser) at positions 124–127 was conserved in 2C8 (SEQ ID NO:8:), 2C9, and 11 (2C19), suggesting that these cytochromes might be regulated by phosphorylation (Muller et al., *FEBS Lett.* 187:21–24 (1985).

However, 2C18 did not contain a serine at this site. the overall percent homology for both nucleic acid and protein sequences is summarized in Table II.

Two additional full-length allelic variants of 2C9 have been isolated. One of these clones is identical with MP-4, but is full-length. It varies from the almost full-length human form 2 isolated by Yasumori et al., supra, by only two silent base changes in the coding region and by four changes in the noncoding region. The number of differences in the nucleic acid sequences of the presumed allelic variants isolated by different laboratories range from 4 to 17 and the amino acid changes vary from 0 to 4, as illustrated in FIG. 3. Two of the amino acid differences occur within the first six N-terminal residues, the others occurring singly throughout the sequence. The effect of these changes on catalytic activity has not been systematically studied. In Relling et al., *J. Pharmacol. Exp. Ther.* 252:442–447 (1990), it was reported that when the cDNAs for 2C8 (SEQ ID NO:8:) and 2C9 4-hydroxylated racemic mephenytoin but did not metabolize (S)-mephenytoin. However, the form of isolated 2C9 (human form 2) which is described in Yasumori et al. (1990), metabolized (S)-mephenytoin preferentially when expressed in yeast. These forms differed by only three amino acids. In contrast, Brian et al., *Biochemistry* 28:4993–4999 (1989) found that when a full-length MP-8 (constructed with the first 15 nucleotides predicted from the known amino acid sequence of P450$_{mp-1}$) was expressed in yeast, it did not metabolize (S)-mephenytoin. This form would differ from human form 2 by only two amino acids. thus, the role of 2C9 in (S)-mephenytoin metabolism remains controversial.

Example 3

Human RNA Blot Analysis and Hybridization Conditions

Poly(A+) RNA (10 μg) was electrophoresed in a 1% agarose gel under denaturing conditions and transferred to a Nytran filter (Micron Separation, Inc., Westboro, Mass.), and filters were then baked for 2 h at 80° C. The filters were prehybridized for 2 h, then hybridized overnight with a $^{32}$P-labeled specific oligonucleotide probe for 2C8 (SEQ ID NO:8:) (T300R) at 42° C., washed 3×5 min at room temperature and 1×5 min at 42° C. with 2×SSC/0.1% SDS, and radioautographed. Filters were then stripped with 5 mM Tris (pH 8.0), 0.2 mM EDTA, 0.05% sodium pyrophosphate, and 0.1×Denhardt's for 2 h at 65° C. and rehybridized with a random-primed actin cDNA (Oncor, Gaithersburg, Md.) at 50° C. using 6×SSC, 4×Denhardts, and 0.5% SDS. These filters were washed 1×5 min at room temperature, 1×10 min at 48° C., and 4×15 min at 48° C. and radioautographed as before. The 2C8 mRNA band was quantitated by scanning with an LKB Ultrascan laser densitometer, and the values of the integrated peaks were divided by those of the actin peaks.

Hybridization with T300R was negligible in mRNA from 860624 compared to S33)and a number of other liver samples (FIG. 5). When corrected for hybridization with the actin probe, the amounts 2C8 (SEQ ID NO:8:) mRNA were consistent with the relative amounts of HLx observed in Western blot analysis. Laser scans of the autoradiographs indicated that 2C8 (SEQ ID NO:8:) mRNA levels in sample 860624 were at least 70-fold lower than S33 and 3 to 15-fold lower than any of the remaining samples.

Example 4

Cell Expression Studies cDNA inserts were ligated into the cloning region of the expression plasmids PSVL (Pharmacia LKB biotechnology, Inc., Piscataway, N.J.) or pcD (Okayama et al., *Mol. Cell. Biol.* 3:280–289 (1983)) and used to transform COS-1 cells. COS-1 cells were placed at (1–2)×10$^6$ cells per 1-cm dish and grown for 24 h in Dulbecco's-modified Eagle's medium with 10% fetal bovine serum (DMEM). The cells were then washed with Dulbecco's phosphate-buffered saline (PBS) and transfected with recombinant plasmid (3 μg per dish) in DEAE-dextran (500 μg/mL) for 30 min-1 h at 37° C. the transfected cells were then treated with chloroquine (52 μg/mL) in DMEM for 5 h (Luthman et al., *Nucleic Acids Res.* 11:1295–1308 (1983)), washed with PBS, refed with DMEM, and incubated for 72 h prior to harvest. Typically, 15–20 dishes were transfected with each recombinant plasmid. For Western blot analysis of the recombinant transformed COS-1 cells, cells were scraped from the dishes into buffer (50 mM Tris-HCl, pH 7.5, 150 mM KCl, and 1 mM EDTA) and lysed with 3×5 s bursts with a polytron. A portion of each lysate was centrifuged at 9000 g and then 10000 g for the preparation of a microsomal fraction. Western blots were then performed as described above. Total RNA was isolated from transfected COS-1 cells, and Northern blots were performed as described for human samples. The filters were hybridized with a $^{32}$P-labeled oligonucleotide probe which hybridizes with all 2C clones isolated (2C500R) (5'-GGAGCACAGCCCAGGATGAA-3') (SEQ ID NO:20:) at 55° C., and radioautographed.

The two variant cDNAs for 2C9, the two variant cDNAs for 2C18, and the cDNA for 2C19 were inserted into expression vectors and transfected into COS-1 cells. Cell lysates were prepared and immunoblotted by using antibody to HLx and P450 2C9. The results are shown in FIG. 4. Transfection of COS-1 cells with the two variants of 2C9 (25 (SEQ ID NO:4:) and 65 (SEQ ID NO:10:)) resulted in the expression of a protein (SEQ ID NO:3:) with a molecular weight equal to that of pure 2C9. In contrast, neither 2C18 (either variant) nor 2C19 was detected by antibody to HLx or 2C9. However, Northern blot analysis indicated that all three cDNAs had been successfully transfected into these cells, the sizes of the transcripts were those expected for the constructs. The somewhat lesser hybridization of the 2C oligoprobe with RNA from cells transfected with IIa (SEQ ID NO:2:) reflects a lower amount of RNA in this sample as shown by the hybridization with the actin probe.

Example 5

Expression of Cytochrome P450 2C19 and 2C18 Polypeptides in a Stable Cell Line

1. Materials (a) Liver Samples and Chemicals

Human liver samples were obtained from Dr. Fred Guengerich, University of Vanderbilt, Nashville, Tenn. Restriction endonucleases were purchased from Stratagene Cloning Systems (La Jolla, Calif.). [$\alpha$-$^{32}$P]dCTP (3000 Ci/mmol), [$\tau^{32}$P]ATP (5000 Ci/mmol) and [$\alpha$-$^{35}$S]dATP (650 Ci/mmol) were from Amersham Corp. (Arlington Heights, Ill.). Nirvanol was obtained from Adrian Kupfer, University of Berne, Switzerland and separated into its R- and S- enantiomers as described by Sobotka et al., *J. Amer. Chem. Soc.* 54:4697–4702 (1932). Radiolabelled S- and R-mephenytoin (N-methyl-$^{14}$C) were synthesized by E. I. Dupont de Nemours & Co., Inc. (Wilmington, Del.) by methylation of R- and S-nirvanol. The radiochemical purity of both isomers was greater than 90% as assessed by HPLC. A single impurity which accounted for less than 2% of the parent compound was not characterized, since it eluted after the metabolites and parent compound. Moreover, the percentage of the impurity remained the same (less than 2%) before and after incubations. All sequencing was done by the dideoxymethod using Sequenase Kits (U.S. Biochemical Corp., Cleveland, Ohio). The specific activities of the S- and R-enantiomers were 20.7 and 20.9 mCi/mmol respectively. All other reagents used are listed below or were of the highest quality available.

(b) Additional Sequences of 2C cDNAs Used in the Expression Studies

Two full-length clones of 2C8 (7b and 7c) described in Romkes et al., *Biochemistry* 30:3247–3255 (1991), were sequenced through the coding region in the present study. The sequences were similar to that of the 2C8(HP1-1) reported by Okino et al., supra; however, both clones had coding changes at position 390 (A→C) (Asn$^{130}$→Thr) and G→C at position 792 (Met$^{264}$→Ile) and a change in the noncoding region at 1497(T→C). These changes presumably represent a second allelic variant of 2C8. The Thr$^{130}$ and Ile$^{264}$ amino acids found in our 2C8 clones are conserved in the remainder of the human P450 2C subfamily (2C9, 2C18, and 2C19) and are therefore consistent with the amino acid substitutions in other members of this subfamily.

(c) Yeast Strains and Media

*Saccharomyces cerevisiae* 334 (MAT α, pep 403, prb1-1122, ura 3-52, leu 2-3, 112, reg1-501,gal1), a protease deficient strain kindly provided by Dr. Ed Perkins (NIEHS), was used as the recipient strain in these studies and propa-gated non-selectively in YPD medium (1% yeast extract, 2% peptone, 2% dextrose) (Hovland et al., *Gene* 83:57–64 (1989)). For the selection of Leu$^+$ transformants, the cells were grown in synthetic complete medium minus leucine (Rose et al., *Methods in Yeast Genetics* (Rose et al., eds.) pp. 180–187, C.S.H.P., NY 1990). Plates were made by the addition of 2% agar.

2. Methods (a) Amplification of 2C18 and 2C9 RNA for Direct Sequencing

Total RNA from selected human liver samples was isolated by the single-step method (Chomozynski et al., *Anal. Biochem.* 163:156–159 (1987), using TRIREAGENT™ (Mol. Res. Center, Inc., OH). RNA (10 μg) was reverse transcribed using 2.6 μM random hexamers as the 3'-primer by incubating for 1 hour at 42° C. using 2.5 U/μl of M-MLV reverse transcriptase (BRL, Grand Island, N.Y.) in 10 mM Tris-HCl, pH 8.3, 5 mM KCl, 5 mM MgCl$_2$, 1 U/μl RNase inhibitor (Promega, Madison, Wis.) and 1 mM each of dATP, dCTP, dGTP, and dTTP (Perkin Elmer Cetus, Norwalk, Conn.). The samples were then heated for 5 minutes at 99° C. to terminate the reverse transcription.

The cDNA was then amplified for a region containing the allelic differences in 2C18 and 2C9 using a nested PCR method. The DNA was amplified in 1×PCR buffer (50 mM KCl, 10 mM Tris-HCl, pH 8.3) containing 1 mM MgCl$_2$, 0.2 mM each of dATP, dCTP, dGTP, dTTP and 20 pmol of each of the 5' and 3' primers in a final reaction volume of 100 μl. The reaction mixture was heated at 94° C. for 5 minutes before addition of 2.5 U of AmpliTaq DNA polymerase (Perkin Elmer Cetus). For PCR of 2C18, the 3'-primer was 5'-TGGCCCTGATAAGGGAGAAT-3' (SEQ. ID NO:23) and the 5'-primers were 5'-ATCCAGAGATACATTGACC TC-3' (SEQ ID NO:24) (outer) and 5'-CCATGAAGTGAC CTGTGATG-3' (SEQ ID NO:26) (inner). For 2C9, the 3'-primer was 5'-AAAGATGGATAATGCCCCAG-3' (SEQ. ID NO:26) and the 5'-primers were 5'-GAAGGAGATCCGGCGTTTCT-3' (SEQ. ID NO:27) (outer) and 5'-GGCGTTTCTCCCTCATGACG-3' (SEQ. ID NO:28) (inner). The outer amplification was performed for 20 cycles consisting of denaturation at 94° C. for 1 minute, annealing at the appropriate temperature for 30 seconds, and extension at 72° C. for 1 min. After a 50-fold dilution, PCR was carried out similarly with the inner primers for 35 additional cycles.

The PCR products were purified using a Centricon-30, dried, suspended in 40 μl of sterile water, and sequenced using Sequenase Kits and a P$^{33}$-end labeled sequencing primer. For 2C18, the primer used was 2C18.1184R 5'-TTGTCATTGTGCAG-3'(SEQ. ID NO:29). Sequencing primers for 2C9 were 2C9.1030F 5'-CACATGCCCTACACA-3'(SEQ. ID NO:30), 2C9.385F 5'-TGACGCTGCGGAATT-3'(SEQ ID NO:31), and 2C9.783F 5'-GGACTTTATTGATTG-3 (SEQ. ID NO:32).

Full length 2C9 cDNA was also amplified by PCR from a human liver with high S-mephenytoin 4'-hydroxylase activity using the primers 5'-ATGATTCTCTTGTGGTC CT-3' (SEQ. ID NO:33) and 5'-AAAGATGGATAATGCC CCCAG-3'(SEQ. ID NO:34). The PCR reaction was similar to above, except that the primer concentrations were increased 10-fold (0.25 μM). The PCR products were then cloned into the pCR1000 vector using the TA Cloning System (In Vitrogen, San Diego, Calif.) and sequenced to identify the allelic variant present.

b. Plasmid Construction and Methods for Amplifying Full-length 2C18 and 2C19 cDNAs by PCR The strategy for cloning the P450 2C cDNAs into the yeast vector pAAH5 is described below. The 5'-noncoding sequence of the P450 2C cDNAs was eliminated by PCR amplification to optimize expression in yeast cells. The 5'-primer introduced a Hind III cloning site and a six A-residue consensus sequence upstream of the ATG codon to promote efficient translation in yeast (Hamilton et al., Nucl. Acids Res. 15:3581–3593 (1987), Cullin et al., Gene 65:203–217 (1988)). The 3'- primer was positioned between the stop codon and polyadenylation site and introduced a second Hind III site. cDNA inserts in the pBluescript vector (0.1 µg) (Romkes et al., (1991), supra) were amplified by PCR as described before except that the reaction contained 3.5 mM $MgCl_2$, 0.25 µM each of the 5'- and 3'- primers, and 1 µl PerfectMatch (Stratagene, La Jolla, Calif.). Amplification was performed in sequential cycles, with the first cycle including denaturation for 1 min. at 94° C., annealing at the appropriate temperature for 1 min., and polymerization at 72° C. for 3 min. The remaining 24 cycles consisted of a denaturation step at 94° C. for 1 min. and a combined annealing/extension step at 72° C. for 3 min. After the last cycle, all samples were incubated an additional 10 min. at 72° C. The primers used were: 2C8: 5'-GCAAGCTTAAAAAAATGGAACCTTTTGTGGTC CT-3' (SEQ. ID NO:35) and 5'-GCAAGCTTGCCAGATG GGCTAGCATTCT-3'; (SEQ. ID NO:36), 2C9: 5'-GCAAGCTTAAAAAAATGGATTCTCTTGTGGTC CT-3' (SEQ. ID NO:37) and 5'-GCAAGCTTGCCAGGC CATCTGCTCTTCT-3'; (SEQ. ID NO:38), 2C19: 5'-GCAAGCTTAAAAAAATGGATTCTCTTGTGGTC CT-3' (SEQ. ID NO:39) and 5'-GCAAGCTTGCCAGAC CATCTGTGCTTCT-3'. (SEQ. ID NO:40)

The PCR products were cloned into the pCR1000 vector (InVitrogen, San Diego, Calif.). Recombinant plasmids were isolated from E. coli (INVαF') cells using Qiagen plasmid purification kits, and the PCR products were completely sequenced as described above to verify the fidelity of the PCR reaction. A mutation of $ASP^2 \rightarrow Val$ was initially introduced inadvertently in 29c via the primers utilized due to an error in the original sequencing at this position. Therefore, the correct 2C18-$Asp^2$ cDNAs were cloned into the pAAH5 vector by an alternate strategy. The 3'-end was cut with NdeI, blunted, and ligated to a SmaI/HindIII adapter. The clone was then partially digested with BamHI which cuts after the initiation ATG as well as internally, and the intact 1700 fragment get purified. A BamHI/HindIII linker was prepared from the oligos 5'-AGCTTAAAAAAATG-3' (SEQ. ID NO:41) (upper) and 5'-GATCCATTTTTTTA-3' (SEQ. ID NO:42) (lower), annealed, and ligated to the cDNA fragment to introduce a HindIII cloning site and regenerate the ATG codon.

The PCR amplified cDNAs were isolated by Hind III digestion, ligated into the pAAH5 yeast expression vector, and the proper orientation confirmed by restriction analysis and sequencing. The expression vector pAAH5, which contains the yeast ADH1 promoter and terminator regions and the Leu2 selectable marker, was kindly provided by Dr. M. Negishi (NIEHS). The recombinant plasmids were isolated from E. coli Dh5α cells using Qiagen plasmid purifications kits and transformed into yeast as described previously (Faletto et al., J. Biol. Chem. 267:2032–2037 (1992), using the lithium acetate method of Ito et al., J. Bacteriol. 153:163–168 (1983).

c. Immunoblots and Cytochrome P450 Determinations

Yeast microsomes or whole cell lysates were prepared from transformed cells isolated at mid-logarithmic phase as described previously (Oeda et al., supra) with slight modifications (Faletto et al., supra) and stored at −80° C. in 0.1M phosphate (pH 7.4) containing 20% glycerol and 0.1 mM EDTA. Protein concentrations were determined by the method of Bradford et al., Anal. Biochem. 72:248–254 (1976). SDS-polyacrylamide gel electrophoresis and Western blots were performed on yeast microsomes or whole cell lysates (Faletto et al., supra) and immunoblots probed with antibody to the appropriate P450 as described (Yeowell et al., Arch. Biochem. Biophys. 243:408–419 (1985). Cytochromes P450 2C8, P450 2C9 and NADPH:P450 reductase were purified from human liver microsomes (Raucy et al., Methods in Enzymol. 208:577–587 (1991) and antibodies to 2C8 and 2C9 prepared in rabbits as previously described (Leo et al., Arch. Biochem. Biohys. 269:305–312 (1988)). Specific peptides $NH_2$-CIDYLPGSHNKIAENFA-COOH (amino acids 231–249) for P450 2C18 and $NH_2$-CLAFMESDILEKVK-COOH (SEQ. ID NO:43) (amino acids 236–249) for 2C19 were selected from amino regions where these P450s vary from other known 2C subfamily members (Romkes et al., (1991), supra). These peptides were synthesized, conjugated to bovine serum albumin via m-maleimidobenzoyl-N-hydroxysuccinimide ester, and antibodies to the conjugates raised in rabbits by BIOSYNTHESIS INC. (Denton, Tex.). E. coli lysate (4 mg/ml) was added to the primary peptide antibody in first step of the immunoblot procedure to block non-specific reactions of these rabbit antibodies to yeast cell wall proteins. Cytochrome P450 concentrations of microsomes were determined by dithionite-reduced carbon monoxide difference spectra by the method of Omura et al., J. Biol. Chem. 239:2370–2378 (1964) using an extinction coefficient of 91 $mM-1\ cm^{-1}$.

Microsomes of human livers were prepared as described by Raucy et al., supra. SDS-polyacrylamide gel electrophoresis and immunoblot analysis was performed as above except that immunoblots were developed using the ECL (enhanced chemiluminescence) Western blotting kit from Amersham (UK). Immunoblots were scanned with a laser densitometer (LKB Instruments).

d. Purification of Cytochromes from Recombinant Yeast Microsomes

Recombinant yeast microsomes were prepared from a 10–12 l culture, and recombinant P450s were purified by aminooctylsepharose chromatography as described by Iwasaki et al., J. Biol. Chem. 226:3380–3382 (1991). The Emulgen was then removed from protein by adsorption of the protein to a 4 g hydroxylapatite column (Hypatite C, Clarkson Chemical Company, Williamsport, Pa.) equilibrated with 10 mM potassium phosphate buffer (pH 7.2), 20% glycerol, 0.1 mM EDTA, and 0.1 mM DTT and washing the column with the same buffer until the absorbance at 280 nm returned to zero. The P450 was then eluted with 4090 mM DTT, and dialyzed overnight against 100 mM potassium phosphate buffer (pH 7.4, 20% glycerol and 0.1 mM EDTA. Absolute and CO difference spectra of purified P450s were determined in the same buffer but containing 0.2% Emulgen and 0.5% cholate.

d. Tolbutamide Hydroxylase Assays

Tolbutamide hydroxylase activity was measured according to Knodell et al., J. Pharmacol. Exper. Ther. 241:1112–1119 (1987), with several modifications. Yeast microsomes (1 mg protein) were preincubated with 300 pmol hamster P450 reductase in 0.2 ml of the incubation buffer (below) for 3 min at 37° C. The reaction was then placed on ice and incubated in 0.2 ml of 50 mM HEPES buffer (pH 7.4) containing 1.5 mM $MgCl_2$, 0.1 mM EDTA in a final volume of 1 ml and 1 mM sodium tolbutamide. The reaction was initiated with 0.5 mM NADPH. Human liver microsomes (0.22 mg protein) were incubated without reductase. Incubations with reconstituted recombinant P450s contained 50 pmol purified P450 enzyme, 150 pmol P450 reductase, and 15 µg dilauroylphosphatidylcholine, and were performed in 100 mM potassium phosphate buffer (pH 7.4). Reactions were terminated after 60 min at 37° C. by the addition of 50 µl of 4N HCl, followed by extraction with 3 ml of water-saturated ethyl acetate. The ethyl acetate extracts were dried under nitrogen at 40° C., the residue resolubilized in 200 µl methanol, and 4-hydroxytolbutamide then assayed using HPLC by injecting 50 µl of the solubilized extract onto a µBONDAPAK $C_{18}$ column (4.6×300 mm) using 0.05% phosphoric acid, pH 2.6: acetonitrile (6:4, v/v) as the mobile phase with a flow rate of 1 ml/min. The column eluate was monitored at 230 nm and rates of product formation were determined from standard curves prepared by adding varying amounts of 4-hydroxytolbutamide to incubations conducted without NADPH. Preliminary experiments confirmed that 4-hydroxytolbutamide formation by human liver microsomes (30–120 pmol P450) was linear for up to 90 min. Samples were analyzed in triplicate.

e. Mephenytoin 4'-Hydroxylase Assay

Mephenytoin 4'-hydroxylase activity was measured by a modification of the radiometric HPLC assay described by Shimada et al., *J. Biol. Chem.* 261:909–921 (1986), as described below. Purified or recombinant yeast microsomes (10–50 pmol) were preincubated with dilauroylphosphatidylcholine (15 µg per 50 pmol P450), P450 reductase (500 U per 50 mol P450), and human cytochrome $b_5$ (2:1 molar ratio when added). The reconstituted mixture was preincubated for 5 min at 37° C., and then placed on ice. A final concentration of 0.4 mM radiolabelled S- or R-mephenytoin (20.7 mCi/mM and 20.9 mCi/mMol) was added to 50 mM HEPES buffer (pH 7.4) containing 0.1 mM EDTA and 1.5 mM $MgCl_2$ for recombinant 2C proteins. The mixture was then incubated at 37° with shaking for 3 min, and the reaction started with the addition of 2 mM NADPH and terminated after 30 min with an equal volume of methanol. Cytochrome $b_5$ was not included in all CYP2C18 reactions, since it had no effect or produced a slight inhibition on the activity of this CYP protein. Reaction volumes were generally 0.25 ml except when the volume of recombinant purified cytochrome or yeast microsomes was greater than 50 µl. In these cases, the volume was increased to 0.5 ml to limit the volume of glycerol from the purified preparation to <4% of the final volume. Incubations with human microsomes did not contain exogenous P450 reductase or cytochrome $b_5$, and they were carried out in 0.1 M phosphate buffer (pH 7.4) instead of HEPES buffer. Initial experiments shows that S-mephenytoin hydroxylase activity of human liver microsomes was linear for at least 60 minutes and from 0.05 through 0.2 mg microsomal protein, and that of the R-enantiomer was linear through 1 mg microsomal protein.

At the end of the incubation period, the reactions were terminated with an equal volume of methanol. The incubation mixture was centrifuged at 10,000 g for 10 min and an aliquot assayed directly using HPLC without extraction. Samples with particularly low activity were concentrated by lyophilization and redissolved in a small volume of methanol:water (1:1) before assay. The HPLC system consisted of a reverse phase C18 (10 µm) Versapak, 300 mm×4.1 mm column (Altech Associates, Deerfield, Ill.) using an isocratic solvent consisting of methanol:water (45:55) with a flow rate was kept of 1 ml/min for 25 min. Detection of radioactive peaks was accomplished using an on-line Flow-One radiochemical detector (Radiomatic Instruments Co., Tampa, Fla. Detection of the unlabeled 4'-hydroxymephenytoin authentic standard was performed using an on-line multiwavelength UV detector at both 211 and 230 nm.

(f) Statistical Analyses

Tolbutamide hydroxylase and mephenytoin hydroxylase activities of microsomes prepared from different recombinant yeasts were compared by analysis of variance and by Fisher's least significant difference test (Carmer et al., *Am. Stat. Ass.* 68:66–74 (1973)).

3. Results (a) Expression of P450 2C cDNAs in Yeast

Western blot analysis confirmed the expression of the recombinant human CYP2C proteins in the recombinant yeast (FIG. 6). Antibodies to 2C8 and 2C9 recognized polypeptide bands of approximately 50,000 daltons (2C8) and 55,000 daltons (2C9) which corresponded in mobility to those of the recombinant proteins purified from yeast microsomes. These mobilities corresponded to those of the corresponding 2C8 and 2C9 proteins purified from human liver. 2C19 was recognized by antibodies to both the 2C9 and the 2C19 peptides. This protein corresponded in mobility (<50,000 daltons) to the lowest of three bands in Western blots of human liver microsomes probed with antibody to human 2C9. The mobility of 2C18 was intermediate between that of 2C8 and 2C19. Antibodies to 2C18 and 2C19 peptides were specific for their antigen; however, antibody to 2C9 cross-reacted strongly with 2C19 and weakly with 2C8 and 2C18.

CO difference spectral analysis indicated that the recombinant P450 2C proteins were expressed at levels as high as 160–250 pmol/mg protein in some yeast microsomal preparations. 2C18, 65 (2C9), and 25 (2C9) were expressed at levels of 20 to 60 pmol/mg microsomal protein. Initially, 11a (2C19) was expressed extremely poorly, and the CO difference spectrum of the recombinant 2C19 yeast was indistinguishable from that of control yeast (<7 pmol/mg protein). However, after repeated transfections and selection, expression of 2C19 at _17 pmol/mg protein was achieved. All of the CYP2C proteins were low spin hemoproteins. CYP2C18 appeared to be somewhat unstable in yeast microsomes with a large proportion (~⅓ to ½) of the P450 being converted to P420 in the presence of dithionite and carbon monoxide. None of the other recombinant CYP2C proteins showed this lack of stability.

(b) Optimization of Tolbutamide and S-Mephenytoin Hydroxylase Assays

Figure 8:
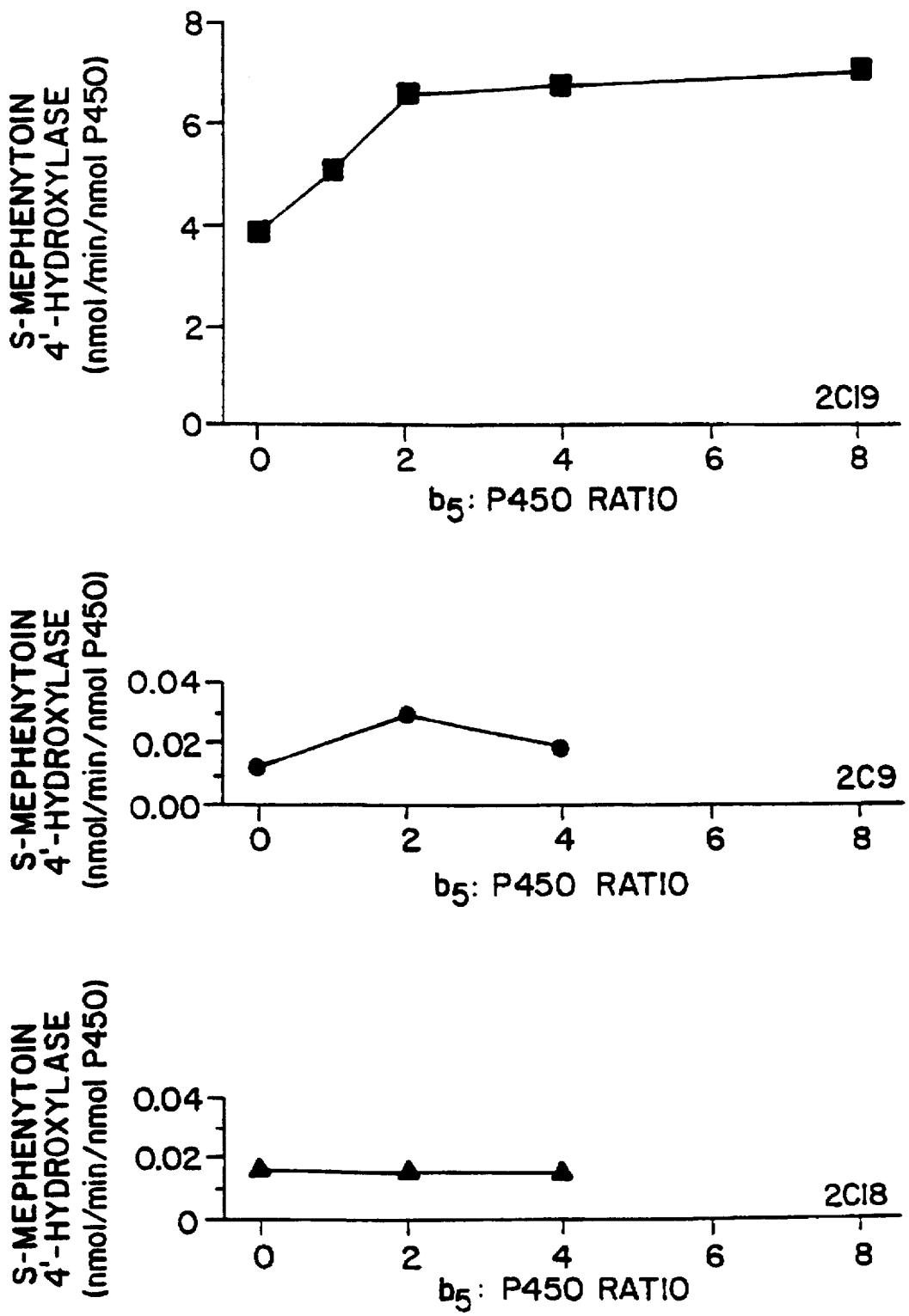
FIG. 8: S-mephenytoin 4'-hydroxylase activity as a function of the molar ratio of cytochrome $b_5$ to recombinant cytochrome P450.

Preliminary studies indicated that exogenous P450 reductase (500 U/50 pmol P450) stimulated metabolism of tolbutamide by recombinant 2C9 in yeast microsomes >10-fold and stimulated S-mephenytoin hydroxylase activity approximately 2-fold. Activity of the recombinant 2C proteins was linear with amount of P450 for 30 minutes through at least 20 pmol P450 for 2C19 (FIG. 7) and 50 pmol for the other CYP2C forms. Cytochrome $b_5$ stimulated S-mephenytoin hydroxylase activity of both 2C9 and 2C19 in yeast microsomes and the optimal ratio of $b_5$ to P450 was approximately 2:1, but it generally had no effect or produced a slight inhibition of mephenytoin hydroxylase activity of 2C18 (FIG. 8). This difference is consistent with the fact that all of the CYP2C proteins except 2C18 contain a Ser at position 128 which is a recognition site for cAMP protein kinase ($^{125}$Arg-Arg-Phe-Ser$^{128}$) (Muller et al., *FEBS Lett.* 187:21–24 (1985), and this sequence is also thought to be part of a $b_5$ binding site (Jansson et al., *Arch. Biochem. Biophys.* 259:441–448 (1987); 2C18 contains Cys at position 125.

Mephenytoin 4'-hydroxylase activity of recombinant yeast microsomes was consistently higher in HEPES than phosphate buffer, while activity of human liver microsomes was ~2-fold higher in phosphate buffer (pH 7.4). Therefore, recombinant proteins were subsequently assayed in HEPES buffer with exogenous reductase and cytochrome $b_5$ except for 2C18 which was tested both with and without cytochrome $b_5$. Human liver microsomal activities were assayed in phosphate buffer.

(c) Mephenytoin Hydroxylase Activity of Recombinant Human 2C Proteins

Figure 9:
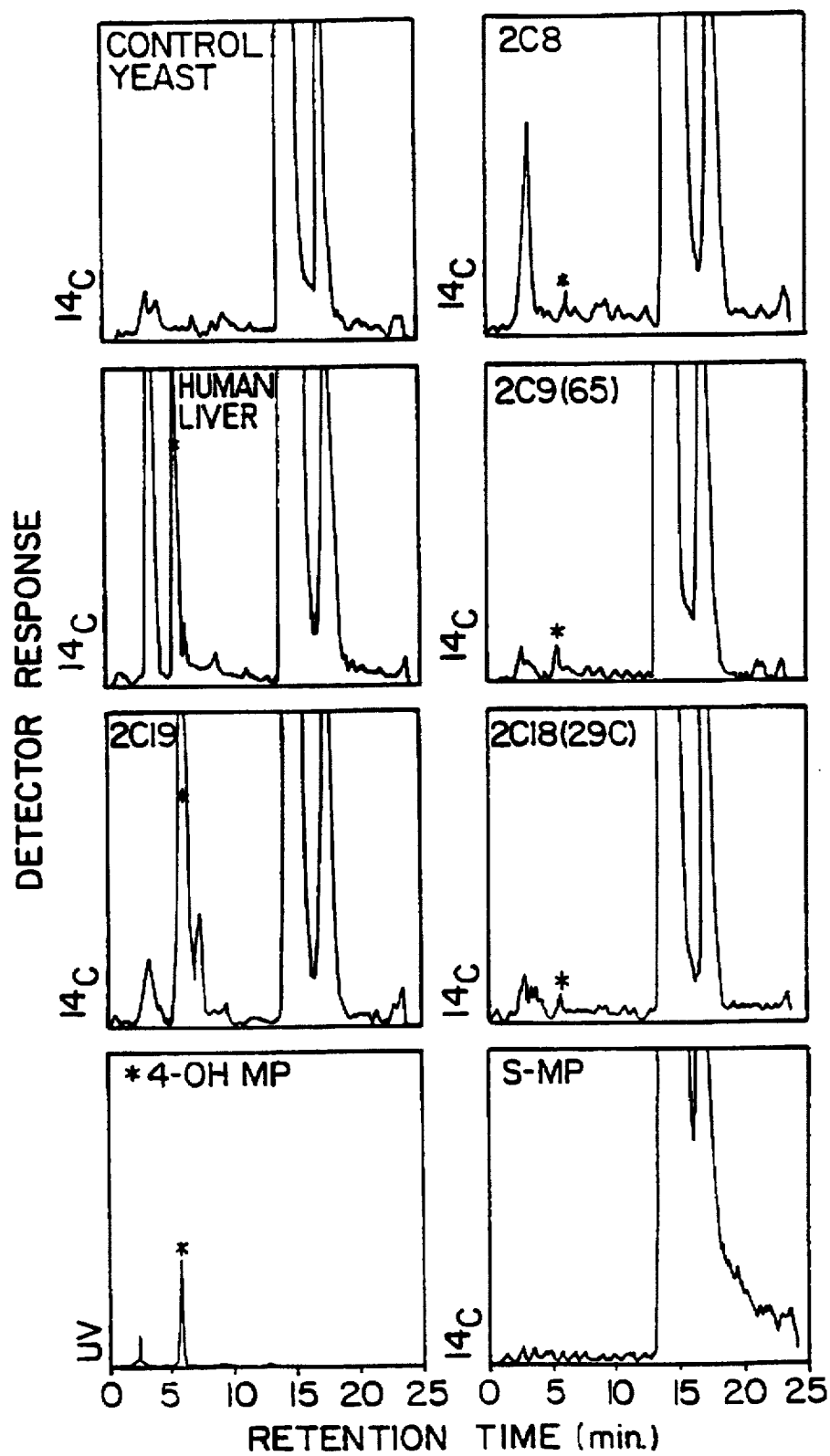
FIG. 9: HPLC radiochromatograms of metabolites formed after incubation of labelled mephenytoin with P450 2C enzymes, human liver microsomes and yeast control.

S-mephenytoin 4'-hydroxylase activities of yeast microsomes containing recombinant human CYP2C proteins were compared under optimized conditions described above. HPCL profiles of the metabolites of S-mephenytoin produced by human liver microsomes and recombinant human CYP2C proteins are shown in FIG. 9 and the results summarized in Table III. Recombinant 2C19 4'-hydroxylated S-mephenytoin at a rate of ~5 nmol/min/nmol P450 which was an order of one magnitude higher than the rate of 4'-hydroxylation in human liver microsomes (Table III and FIG. 9). The retention time (5–6 min) of the 4'-hydroxymephenytoin metabolite was identical to that of the authentic unlabeled standard. 2C19 also produced small quantities of two unknown metabolites eluted at 3–4 and 7–8 min. These unknown metabolites were also produced by liver microsomes, and the metabolite with the shorter retention time was the principal metabolite produced by 2C8. Parent S-mephenytoin eluted at 14–15 min. followed by the unknown impurity which eluted at 16–17 min. Similar retention times were observed for R-mephenytoin and its metabolites.

The rate of 4'-hydroxymephenytoin formation by 2C19 was at least 100-fold higher than that of 2C9 (both alleles), 2C18 (both alleles) and 2C8 (Table III). The rate of 4'-hydroxylation of S-mephenytoin by 2C8 appeared to be lower than that of 2C9 (0.02 nmol/min/nmol). The 4'-hydroxylation of mephenytoin by 2C19 was stereospecific; the rate of S-hydroxylation was at least 30-fold higher than that of R-hydroxylation (Table III). In contrast, the 4'-hydroxylation of mephenytoin by the other human CYP2C proteins did not appear to be stereospecific.

TABLE III

S-Mephenytoin 4'-Hydroxylase Activities in Recombinant Human CYP2C Yeast Microsomes

| Microsomes | Mephenytoin 4'-Hydroxylase Activity nmol/min/nmol P450 | | R/S Ratio |
|---|---|---|---|
| | S | R | |
| Controls | 0.028 ± 0.001 | 0.024 ± 0.003 | 0.9 |
| 2C9-Ile$^{359}$ (65) | 0.043 ± 0.000 | 0.041 ± 0.005 | 0.9 |
| 2C9-Leu$^{359}$ (25) | 0.031 ± 0.009 | 0.040 ± 0.01 | 1.3 |
| 2C8 | 0.037 ± 0.001 | 0.016 ± 0.001 | 0.4 |
| 2C18-Thr$^{385}$ (29c) + b5 | 0.042 ± 0.004 | 0.054 ± 0.003$^a$ | 1.3 |
| 2C18-Thr$^{385}$ (29c), no b5 | 0.034 ± 0.008 | — | |
| 2C18-Met$^{385}$ (6b) | 0.023 ± 0.004 | 0.019 ± 0.005 | 0.9 |
| 2C19 (11a) | 4.6 ± 0.3$^{a,b,d}$ | 0.014 ± 0.02$^a$ | 0.03 |
| Human liver microsomes HB1 6 | 0.283 ± 0.037$^{a,c,d}$ | 0.117 ± 0.017$^{a,c}$ | 0.4 |

S-Mephenytoin hydroxylase assayed as described in Methods. Reaction mixtures contained 10 pmol of recombinant CYP2C19 or 50 pmol of other recombinant CYP2C yeast microsomes, 500 U of purified P450 reductase and 15 μg phospholipid per 50 pmol of P450, and 0.4 mM radioactive substrate in 0.1M HEPES buffer (pH 7.4). Unless otherwise stated recombinant yeast microsomes were also reconstituted with a 2:1 molar ratio of cytochrome $b_5$. Reactions were incubated at 37° C. for 30 min with 1 mM NADPH. Control reactions contained the same reaction mixture and were incubated similarly with an equivalent amount of control yeast microsomal protein (1 mg). Specific content of P450 of the recombinant yeast microsomes ranged from 35–48 pmol/mg except for 2C8 (191 pmol/mg) and 2C19 (17 pmol/mg). Control liver reactions contained 0.1 mg microsomal protein but were not fortified with reductase, cytochrome $b_5$, or phospholipid and were incubated with 0.1M phosphate buffer (pH 7.4). Values represent the means ± SE.
$^a$Activity significantly higher than that of control yeast microsomes, P < 0.05. Analysis of variance and Fisher's Least Significant difference test.
$^b$2C19 activity significantly higher than activities of all other recombinant CYP2C proteins or human liver microsomes, P < 0.05.
$^c$Human liver microsomes significantly higher than recombinant microsomes except 2C19, P < 0.05.
$^d$Significant difference between S- and R-Mephenytoin hydroxylase activities, P < 0.05.

TABLE IV

Mephenytoin 4'-Hydroxylase and Tolbutamide Hydroxylase Activities of Purified Recombinant Human P450s from the 2C subfamily

| P450 2C (clone) | Mephenytoin 4'-Hydroxylase Activity (nmol/min/nmol P450) | | R/S Ratio | Tolbutamide Hydroxylase Activity (pmol/min/nmol P450) |
|---|---|---|---|---|
| | S | R | | |
| 2C19 | 6.17 ± 0.24$^{a,b,c}$ | 0.19 ± 0.04$^a$ | 0.03 | ND |
| 2C9-Ile$^{359}$ (65) | 0.081 ± 0.006$^a$ | 0.063 ± 0.003$^a$ | 0.77 | 122 + 29$^{a,d}$ |
| 2C9-Leu$^{359}$ (25) | ND | ND | | 10 + 2 |
| 2C18-Asp$^2$Thr$^{385}$ (29c-1a) | 0.116 ± 0.010$^a$ | 0.147 ± 0.025$^a$ | 1.3 | ND |
| 2C18-Val$^2$Thr$^{385}$ (29c) | 0.019 ± 0.001 | 0.073 ± 0.009$^{a,c}$ | 2.7 | 102 ± 2$^{a,d}$ |
| 2C18-Asp$^2$Met$^{385}$ (6b) | 0.103 ± 0.016$^a$ | 0.107 ± 0.005$^c$ | 1.0 | ND |
| 2C8 | 0.057 ± 0.009$^{a,c}$ | 0.023 ± 0.004 | 0.4 | 12 ± 4 |
| 2C8 Purified from Human Liver | 0.032 ± 0.003 | 0.051 ± 0.030 | 1.6 | ND |
| 2C9 Purified from Human Liver | 0.033 ± 0.001 | 0.051 ± 0.007$^{a,c}$ | 1.6 | 109 ± 16 (390, 2,840)$^{a,d,c}$ |
| Human Liver Microsomes HB16 | 0.46 ± 0.02$^a$ | 0.28 ± 0.01 | 0.6 | ND |
| Human Liver Microsomes UC8936 | — | — | | 408 ± 21 |

TABLE IV-continued

Mephenytoin 4'-Hydroxylase and Tolbutamide Hydroxylase Activities of Purified Recombinant Human P450s from the 2C subfamily

| | Mephenytoin 4'-Hydroxylase Activity (nmol/min/nmol P450) | | Tolbutamide Hydroxylase Activity |
|---|---|---|---|
| P450 2C (clone) | S | R | R/S Ratio (pmol/min/nmol P450) |

Recombinant P450s were purified from yeast microsomes and assays performed as described in Methods. 2C9 were purified from human liver (Raucy and Lasker, 1991). Assays were performed in triplicate and values represent means ± SE. Blank reactions (containing all components except the P450) were subtracted (22 ± 5) from tolbutamide hydroxylase values. Blank reactions for the S-mephenytoin assay were not subtracted since no distinct peaks with the exact retention times of 4'-hydroxymephenytoin were observed; however, background radioactivity was in the range of $^{-}0.025 \pm 0.01$ nmol/min/nmol. ND = Not determined.
[a]Increased over blank values, $P < 0.05$
[b]S-Mephenytoin hydroxylase activity of 2C19 significantly greater than all other values, $P < 0.05$
[c]S-Mephenytoin hydroxylase activity of significantly different from R-mephenytoin values, $P < 0.05$.
[d]Tolbutamide hydroxylase activity of 65 and 29c were significantly greater than 25, or 2C8 ($P < 0.0001$).
[e]Tolbutamide hydroxylase activity of two other 2C9 preparations derived from different human livers in parentheses.

Recombinant CYP2C proteins were purified from yeast microsomes and their ability to 4'-hydroxylate the S- and R-enantiomers of mephenytoin were also examined in a reconstituted system (Table IV). 2C19 had similar turnover numbers for S-mephenytoin 4'-hydroxylation in the reconstituted system and in recombinant yeast microsomes fortified with reductase. This turnover number was at least 10-times higher than that of human liver microsomes, and it was 50–100 times higher than that of recombinant 2C9, 2C18 or 2C8. The turnover number of recombinant 2C9 was ~100 times higher than the activity of a preparation of 2C9 purified from human liver. 4'-hydroxylation of mephenytoin by 2C19 was stereospecific for the S-enantiomer, while metabolism by 2C9 was not stereospecific. Surprisingly, 2C18 appeared to be stereoselective for the R-enantiomer of mephenytoin. The turnover number of 2C19 for S-mephenytoin 4'-hydroxylase was also ~30 times higher than the turnover numbers reported for a preparation P450$_{MP}$ purified from human liver by Srivastava et al., Mol. Pharmacol. 40:69–79 (1991) (0.21 nmol/min/nmol P450).

Although 2C9 exhibits poor catalytic activity toward S-mephenytoin, this cytochrome appears to be the principal tolbutamide hydroxylase (Table IV and V). The turnover numbers for hydroxylation of tolbutamide by the purified recombinant 2C9 were somewhat lower than those of 2C9 purified form human liver in the absence of exogenous reductase. The Ile$^{359}$ allele of 2C9 had a 3-fold higher turnover number for tolbutamide than the Leu$^{359}$ allele when activity of the recombinant microsomes were adjusted for P450 content (Table V). 2C19 also appeared to metabolize tolbutamide at a rate comparable to that of 2C9, although this rate was difficult to estimate due to the low specific content of P450 in the recombinant 2C19 yeast clone available at the time of these assays. The two alleles of 2C18 exhibited lower tolbutamide hydroxylase activity than 2C9 in recombinant yeast microsomes.

TABLE V

Tolbutamide Hydroxylase Activities of Recombinant Human CYP2C Yeast Microsomes

| Microsomes | P450 Content (pmol/mg) | Tolbutamide Hydroxylase Activity | |
|---|---|---|---|
| | | (nmol/min/ mg protein) | (nmol/min/ nmol P450) |
| Control Yeast | <5 | 0.3 ± 0.01 | — |
| 2C9-Ile$^{359}$ (65) | 55 | 169.8 ± 7.4[a,b] | 3.4 ± 0.15 |
| 2C9-Leu$^{359}$ (25) | 20 | 14.8 ± 0.3[a,c] | 0.99 ± 0.02 |
| 2C8 | 80 | 8.5 ± 0.2[a] | 0.11 ± 0.003 |
| 2C18-Asp²Thr$^{385}$ (29c-1a) | 53 | 9.3 ± 0.7[a] | 0.19 ± 0.02 |
| 2C18-Asp²Met$^{385}$ (6b-9) | 34 | 11.1 ± 1.2[a] | 0.37 ± 0.04 |
| 2C19 (11a-3) | <7 | 18.4 ± 2.4[a,d] | ND |
| UC8936 Human Liver Microsomes | 227 | 116 ± 0.8[a] | 2.3 ± 0.02 |

Tolbutamide hydroxylase activities measured as described in methods. Reaction mixtures contained 1 mg yeast microsomal protein or 0.2 mg UC8936 human liver microsomal protein (50 pmol P450). Purified P450 reductase (1,000 units) was included in reactions with yeast microsomes but not human microsomes. Values were the means ± SE. ND = Not calculated due to low specific content of 2C19 in yeast in this experiment.
[a]Significantly higher than control yeast microsomes, $P < 0.05$. Pairwise comparisons using Fisher's Least significant Difference test.
[b]Clone 65 significantly higher than all other clones ($P < 0.0001$).
[c]Clone 25 significantly greater than 2C8 ($P < 0.0005$).
[d]Clone 11a significantly higher than 2C8 ($P < 0.0001$).

The data show that CYP2C19 stereospecifically hydroxylates S-mephenytoin at the 4'- position at a rate which is at least 10 times higher than the rate in human liver microsomes. This is the first example of a human CYP protein which metabolizes S-mephenytoin with a turnover number appreciably higher than that of human liver microsomes. Other 2C proteins showed a 100-fold reduced activity relative to 2C19. One of the 2C9 variants tested (Ile$^{359}$) is identical to that reported by Yasumori et al., supra to show a low level of S-mephenytoin 4'-hydroxylase activity. The low rate of 4'-hydroxylation of S-mephenytoin by 2C9 detected in the present study with high specific activity $^{14}$C-labeled S-mephenytoin undoubtedly explains the conflicting reports from various laboratories concerning the ability of this cytochrome to metabolize mephenytoin (Yasumori et al., supra; Srivastava et al., supra; Relling et al., supra).

(d) Comparisons of Immunoblot Analysis of CYP2C Proteins in Human Livers with Liver Microsomal S-Mephenytoin 4'-Hydroxylase Activities Microsomes from 16 human liver donor samples previously assayed for S- and R-mephenytoin 4'-hydroxylase activities were analyzed for CYP2C proteins by Western blot analysis (FIG. 10) using an antibody to 2C8 and a polyclonal antibody to 2C9 and 2C19. Both 2C18 and 2C19 have mobilities similar to that of the low molecular weight band recognized in human microsomes by most antibodies to 2C9. However, an antibody to a 2C19 peptide was specific for 2C19. 2C18 could not be detected in human liver samples using a peptide antibody to 2C18 (~5 pmol detection limit), indicating that this polypeptide is expressed poorly in human liver human liver (<50 pmol/mg).

Figures 1, 10:
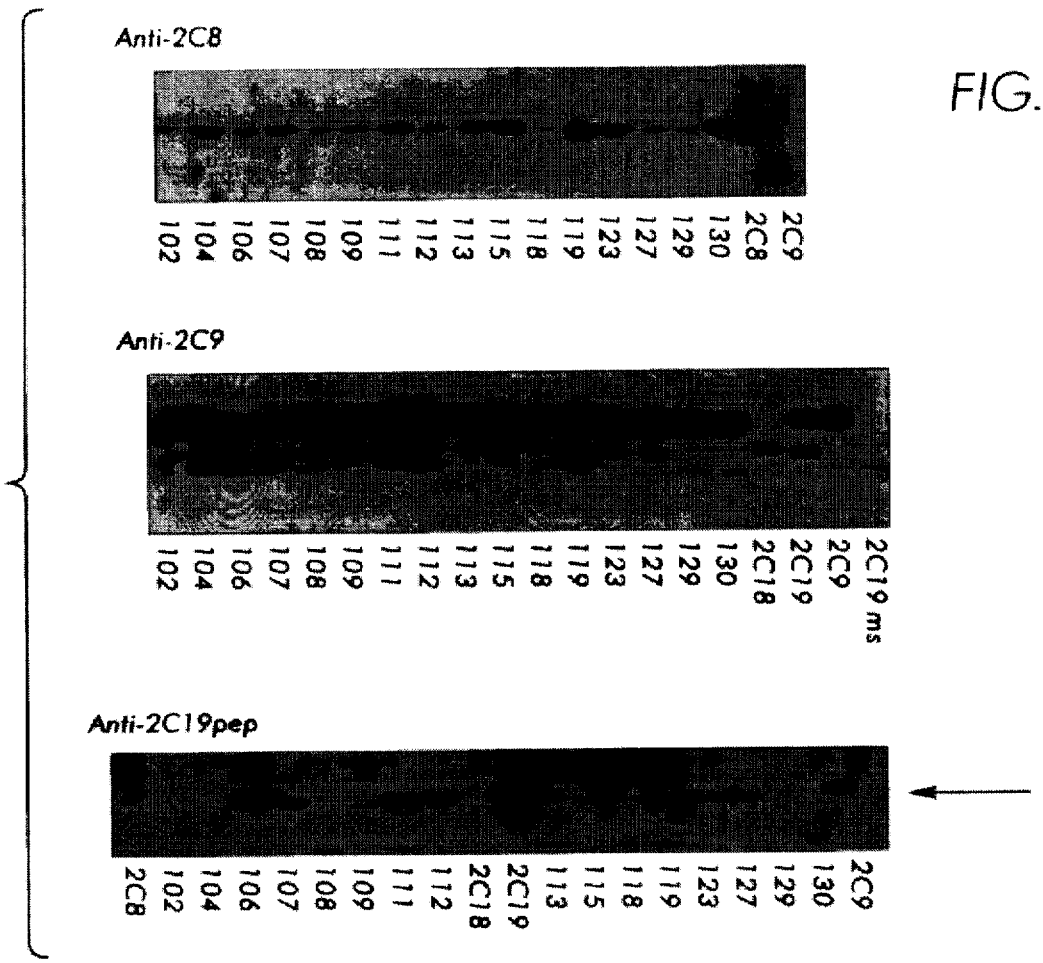
FIG. 1 shows Western blots of human liver microsomal proteins. Microsomal proteins were separated by SDS-polyacrylamide gel electrophoresis. Blot A was performed using polyclonal antibody to 2C9 and blot B with anti-2C8 (HLx). Each lane represents 20 µg of microsomal protein from an individual liver. The 2C8 antibody also recognized purified rat P450 2C13 (g). cDNA libraries were constructed from livers 860624 (low HLx) and S33 (high HLx).
FIG. 10: Comparison of liver content of cytochrome P450 2C enzymes with S-mephenytoin 4'-hydroxylase activity.
Figures 2, 10:
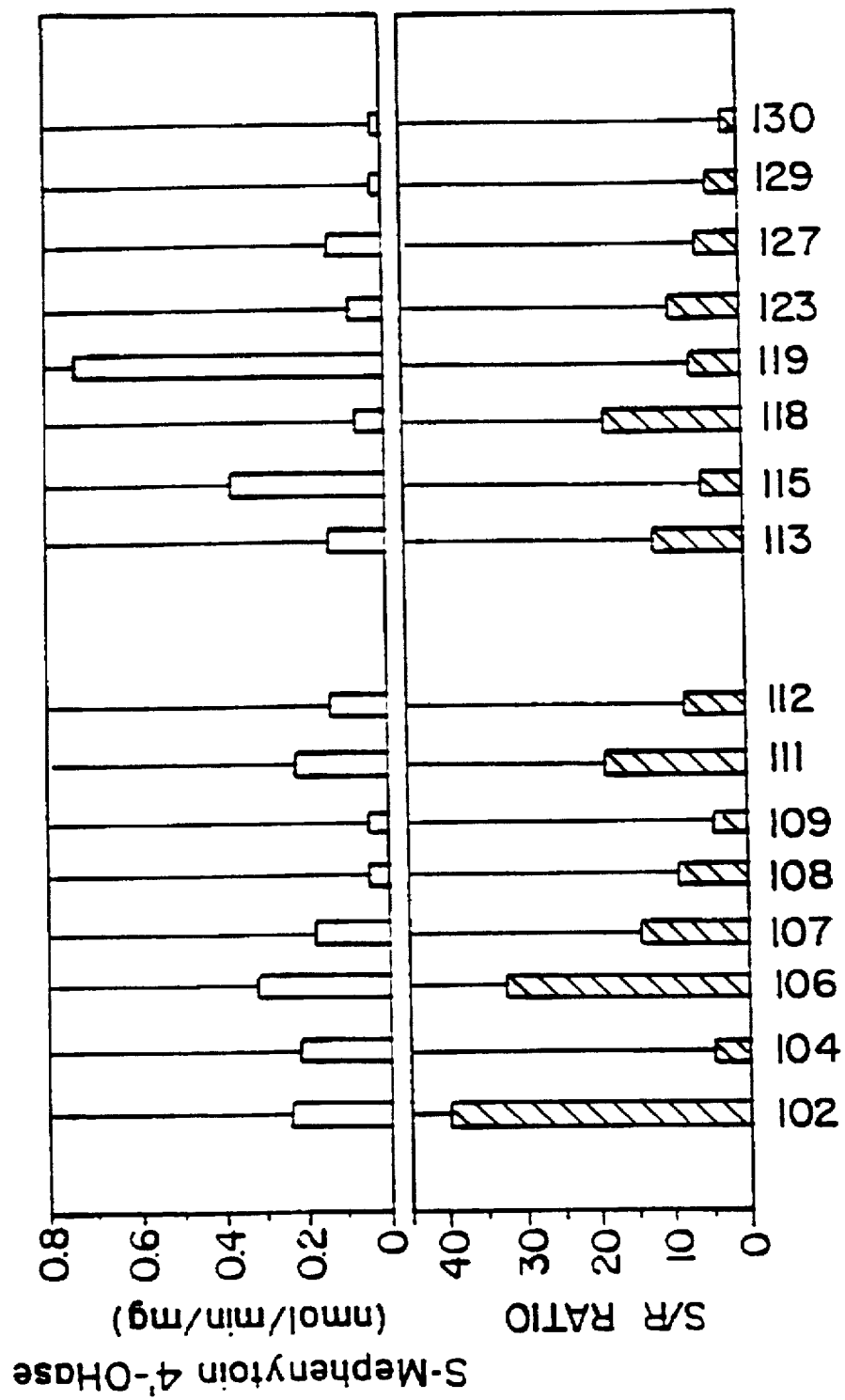
FIG. 2 (Sheets 2-1 to 2-9) contains nucleotide sequences of human P450 2C cDNAs. 2c (SEQ ID NO:14:) is indicated in the top line and represents the consensus sequence where information from more than one sequence is available. Sequences were determined by the dideoxy chain termination method. The differences observed for clones 25 (SEQ ID NO:4:) and 65 (SEQ ID NO:10:) are underlined. The termination codons are starred. The heme binding region and polyadenylation signals are underlined. The one-base difference between 29c (SEQ ID NO:6:) and 6b (SEQ ID NO:12:) are also underlined. The termination codon is starred. The new allelic variant proteins of 2C18, referred to as 29c (SEQ ID NO:5:) and 6b (SEQ ID NO:11), and the new protein of 2C19, referred to as 11a (SEQ ID NO:1:), are compared with the protein of 2C8, referred to as 2C8 (SEQ ID NO:7:), and the allelic variant proteins of 2C9, referred to as 65 (SEQ ID NO:9:) and 25 (SEQ ID NO:3:).
Figure 11:
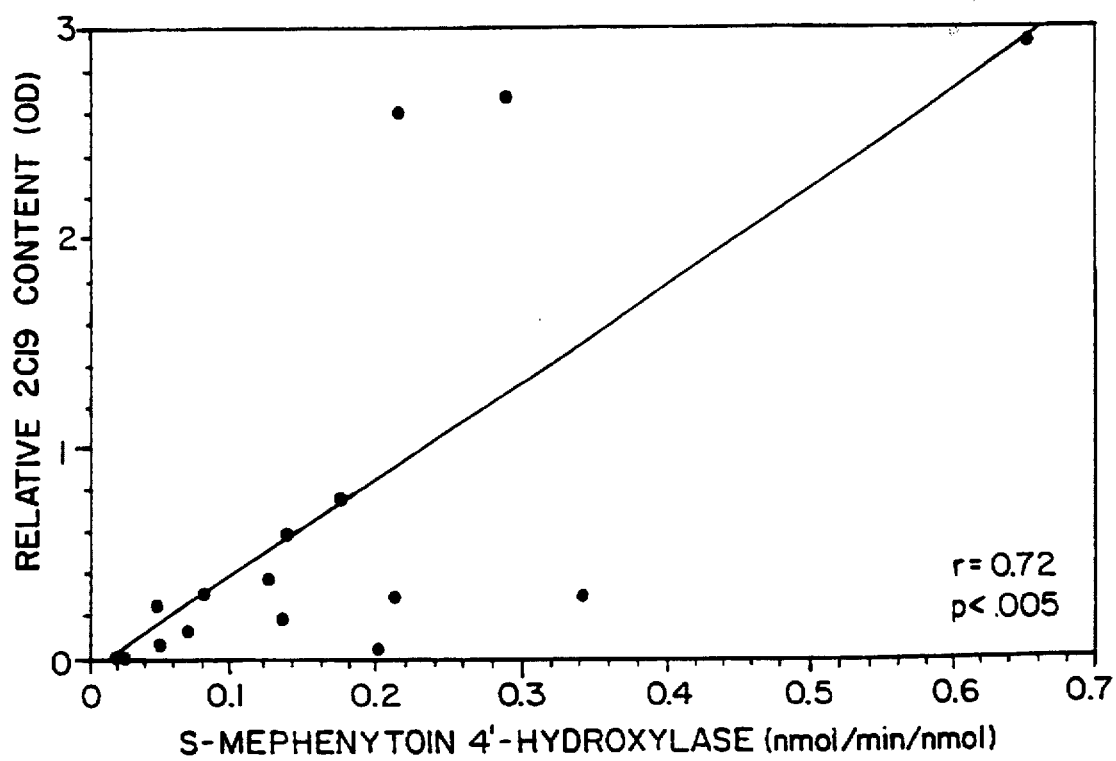
FIG. 11: Correlation between hepatic 2C19 content and S-mephenytoin hydroxylase activity based on the data shown in FIG. 10.

The 2C19 content of liver microsomes was consistent with their S-mephenytoin 4'-hydroxylase activities (FIG. 10). In particular, samples 129 and 130 had extremely low S-mephenytoin 4'-hydroxylase values, low S/R ratios, and 2C19 appeared to be essentially absent in these microsomal samples. Densitometric analysis of immunoblots revealed that 2C19 content of the 16 human liver microsomes correlated significantly with S-mephenytoin 4'-hydroxylase activity (r=0.718, P<0.005) (FIG. 11), but that the content of 2C9 did not correlate with this catalytic activity (r=0.49, P>0.05). There was also a significant correlation between 2C8 content and S-mephenytoin 4'-hydroxylase activity (r=0.82, P<0.0001). However, this correlation was probably fortuitous, because 2C8 shows very low S-mephenytoin 4'-hydroxylase activity either in recombinant form or when purified from human liver. Alternatively, the correlation may indicate an indirect regulatory role for 2C8 in controlling S-mephenytoin 4'-hydroxylase activity.

(e) Sequences of 2C9 and 2C18 mRNAs in Livers with High or Low S-mephenytoin 4'-Hydroxylase Activities 2C18 and 2C9 mRNAs from six of the above livers were amplified by PCR and directly sequenced through areas of known allelic variation to determine whether there was a relationship between S-mephenytoin 4'-hydroxylase activity and the presence of a particular allelic variant (Table VI). When the total 2C18 PCR products were sequenced, the two individuals with the highest S-mephenytoin hydroxylase activity were homozygous for $Thr^{385}$(ACG). Of the two individuals with the lowest activity, one was homozygous for $Met^{385}$, and one was heterozygous for $Thr/Met^{385}$(AC/TG). Two individuals with intermediate activity were also homozygous for $Thr^{385}$. Similarly, when 2C9 mRNA from these same individuals was amplified and sequenced through known allelic variations, sample 108 (low S-mephenytoin 4'-hydroxylase activity) was heterozygous at $C/T^{430}$ (coding for $Cys/Arg^{144}$), while the other five individuals were homozygous for $C^{430}$ ($Arg^{144}$). Sequencing samples through bases 1072–1077, all samples except for 106 (high activity) read $^{1072}TACATT^{1077}$, coding for $Tyr^{358}Ile^{359}$. Sample 106 read TACA/CTT indicating that it was heterozygous for $Ile/Leu^{359}$. These data indicate that there is no relationship between S-mephenytoin 4'-hydroxylase activity of human liver microsomes and the identity of the allelic variants of 2C18 ($Thr/Met^{385}$) or 2C9 ($Arg/Cys^{144}$, $Tyr/Cys^{358}$, $Ile/Leu^{359}$) in these tissues.

TABLE VI

Alleles in Human Livers with Varying S-Mephenytoin 4'-Hydroxylase Phenotypes

| Phenotype | S-MPOHase nmol/ min/mg | Liver 2C18 donor allele | 2C9 allele | | | |
|---|---|---|---|---|---|---|
| High | 0.286 | 106 $Thr^{385}$ | $Arg^{144}$ | $His^{276}$ | $Tyr^{358}$ | $Ile/Leu^{359}$ |
| High | 0.351 | 115 $Thr^{385}$ | $Arg^{144}$ | $His^{276}$ | $Tyr^{358}$ | $Ile^{359}$ |
| Intermediate | 0.070 | 118 $Thr^{385}$ | $Arg^{144}$ | $His^{276}$ | $Tyr^{358}$ | $Leu^{359}$ |
| Intermediate | 0.081 | 123 $Thr^{385}$ | $Arg^{144}$ | $His^{276}$ | $Tyr^{358}$ | $Ile^{359}$ |
| Low | 0.051 | 108 $Thr/Met^{385}$ | $Arg/Cys^{144}$ | $His^{276}$ | $Tyr^{358}$ | $Ile^{359}$ |
| Low | 0.025 | 129 $Met/Met^{385}$ | $Arg^{144}$ | $His^{276}$ | $Tyr^{358}$ | $Ile^{359}$ |

3. Conclusion

These results show that 2C19 has a turnover number for the 4'-hydroxylation of S-mephenytoin about 100-fold higher than that of 2C9, 2C18, or 2C8. 2C19 hydroxylation was stereospecific for the S- enantiomer. The hepatic content of 2C19 in 16 liver microsomal samples correlated with their S-mephenytoin 4'-hydroxylase activities. 2C9 appeared to be the primary tolbutamide hydroxylase, although 2C19 may also contribute to this catalytic activity. The identity of the allelic variant of 2C9 or 2C18 did not influence S-mephenytoin 4'-hydroxylase activity. These data strongly indicate that 2C19 is the key determinant of S-mephenytoin 4'-hydroxylase activity in human liver.

While the foregoing invention has been described in some detail for purposes of clarity and understanding, it will be clear to one skilled in the art from a reading of this disclosure that various changes in form and detail can be made without departing from the true scope of the invention. all publications and patent documents cited in this application are incorporated by reference in their entirety for all purposes to the same extent as if each individual publication or patent document were so individually denoted.

What is claimed is:

1. A method of screening for a drug that is metabolized by a cytochrome P450 having S-mephenytoin 4' hydroxylase activity, the method comprising the steps of:
    contacting the drug with a cytochrome P450 2C19 polypeptide; and
    detecting a metabolic product resulting from an interaction between the drug and the polypeptide, the presence of the product indicating the drug is metabolized by the S-mephenytoin 4'-hydroxylase activity.

2. The method of claim 1 wherein the cytochrome P450 2C19 polypeptide is substantially pure.

3. The method of claim 1, wherein the cytochrome P450 2C19 polypeptide is a component of a lysate of a stable cell line expressing the cytochrome P450 2C19 polypeptide.

4. The method of claim 1, wherein the cytochrome P450 2C19 is a component of a stable cell line.

5. The method of claim 1, further comprising the steps of:
   contacting the drug with a liver extract comprising a mixture of cytochrome P450 polypeptides; and
   detecting a metabolic product resulting from an interaction between the drug and the mixture of cytochrome P450 polypeptides.

6. A method of identifying a mutagenic, carcinogenic or cytotoxic compound, the method comprising the steps of:
   (a) contacting the compound with a stable cell line comprising an exogenous DNA segment encoding a cytochrome P450 2C19 polypeptide having at least 97% sequence identity with the amino acid sequence designated SEQ. ID. No. 1, the DNA segment capable of being expressed in the cell line; and
   (b) assaying for mutagenic, carcinogenic or cytotoxic effects of the compound on the stable cell.

7. A method of identifying a mutagenic, carcinogenic or cytotoxic compound, the method comprising the steps of:
   (a) contacting the compound with a cytochrome P450 2C19 polypeptide in a reaction mixture to generate a metabolic product resulting from S-mephenytoin 4'-hydroxylase activity on the compound;
   (b) assaying the metabolic product for mutagenic, carcinogenic or cytotoxic effects on a test cell line, the effects indicating that the compound is mutagenic, carcinogenic or cytotoxic.

8. The method of claim 7, further comprising the step of adding the test cell line to the reaction mixture.

9. The method of claim 8, wherein the contacting and adding steps are performed simultaneously.

10. The method of claim 9, wherein the cytochrome P450 2C19 polypeptide is a component of a lysate of a stable cell line.

11. The method of claim 10 wherein the test cell line is a *Salmonella typhimurium* cell line having an auxotrophic histidine mutation.

12. A method for identifying or testing the chemopreventive activity of an agent comprising the steps of:
   (a) contacting a stable cell line with an agent suspected of being a chemopreventive in the presence of a carcinogen, wherein the stable cell line comprises an exogenous DNA segment encoding a cytochrome P450 2C19 polypeptide having at least 97% sequence identity with the amino acid sequence designated SEQ. ID. No. 1, the DNA segment capable of being expressed in the cell line; and
   (b) monitoring effects on a test cell line that are indicative of chemopreventive activity.

13. The method of claim 12 wherein the agent is contacted with the cell line prior to the addition of the carcinogen.

14. A method for determining the metabolites activated by a carcinogen or xenobiotic, the method comprising the steps of:
   (a) contacting a stable cell line with the suspected carcinogen or xenobiotic, wherein the stable cell line comprises an exogenous DNA segment encoding a cytochrome P450 2C19 polypeptide having at least 97% sequence identity with the amino acid sequence designated SEQ. ID. No. 1, the DNA segment capable of being expressed in the cell line; and
   (b) identifying the metabolites and/or their effects.

* * * * *

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 490 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
Met Asp Pro Phe Val Val Leu Val Leu Cys Leu Ser Cys Leu Leu Leu
 1               5                  10                  15

Leu Ser Ile Trp Arg Gln Ser Ser Gly Arg Gly Lys Leu Pro Pro Gly
            20                  25                  30

Pro Thr Pro Leu Pro Val Ile Gly Asn Ile Leu Gln Ile Asp Ile Lys
        35                  40                  45

Asp Val Ser Lys Ser Leu Thr Asn Leu Ser Lys Ile Tyr Gly Pro Val
    50                  55                  60

Phe Thr Leu Tyr Phe Gly Leu Glu Arg Met Val Val Leu His Gly Tyr
65                  70                  75                  80

Glu Val Val Lys Glu Ala Leu Ile Asp Leu Gly Glu Glu Phe Ser Gly
                85                  90                  95

Arg Gly His Phe Pro Leu Ala Glu Arg Ala Asn Arg Gly Phe Gly Ile
                100                 105                 110

Val Phe Ser Asn Gly Lys Arg Trp Lys Glu Ile Arg Arg Phe Ser Leu
                115                 120                 125

Met Thr Leu Arg Asn Phe Gly Met Gly Lys Arg Ser Ile Glu Asp Arg
            130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe Gln Lys Arg Phe Asp Tyr Lys Asp Gln
                180                 185                 190

Gln Phe Leu Asn Leu Met Glu Lys Leu Asn Glu Asn Ile Arg Ile Val
            195                 200                 205

Ser Thr Pro Trp Ile Gln Ile Cys Asn Asn Phe Pro Thr Ile Ile Asp
    210                 215                 220

Tyr Phe Pro Gly Thr His Asn Lys Leu Leu Lys Asn Leu Ala Phe Met
225                 230                 235                 240

Glu Ser Asp Ile Leu Glu Lys Val Lys Glu His Gln Glu Ser Met Asp
                245                 250                 255

Ile Asn Asn Pro Arg Asp Phe Ile Asp Cys Phe Leu Ile Lys Met Glu
                260                 265                 270

Lys Glu Lys Gln Asn Gln Gln Ser Glu Phe Thr Ile Glu Asn Leu Val
            275                 280                 285

Ile Thr Ala Ala Asp Leu Leu Gly Ala Gly Thr Glu Thr Thr Ser Thr
        290                 295                 300

Thr Leu Arg Tyr Ala Leu Leu Leu Leu Leu Lys His Pro Glu Val Thr
305                 310                 315                 320

Ala Lys Val Gln Glu Glu Ile Glu Arg Val Ile Gly Arg Asn Arg Ser
```

|   |   |   |   |   | 325 |   |   |   |   | 330 |   |   |   |   | 335 |   |   |
|---|---|---|---|---|---|---|---|---|---|---|---|---|---|---|---|---|---|

```
            Pro  Cys  Met  Gln  Asp  Arg  Gly  His  Met  Pro  Tyr  Thr  Asp  Ala  Val  Val
                           340                     345                     350

His  Glu  Val  Gln  Arg  Tyr  Ile  Asp  Leu  Ile  Pro  Thr  Ser  Leu  Pro  His
                           355                     360                     365

Ala  Val  Thr  Cys  Asp  Val  Lys  Phe  Arg  Asn  Tyr  Leu  Ile  Pro  Lys  Gly
                           370                     375                     380

Thr  Thr  Ile  Leu  Thr  Ser  Leu  Thr  Ser  Val  Leu  His  Asp  Asn  Lys  Glu
            385                     390                     395                     400

Phe  Pro  Asn  Pro  Glu  Met  Phe  Asp  Pro  Arg  His  Phe  Leu  Asp  Glu  Gly
                           405                     410                     415

Gly  Asn  Phe  Lys  Lys  Ser  Asn  Tyr  Phe  Met  Pro  Phe  Ser  Ala  Gly  Lys
                           420                     425                     430

Arg  Ile  Cys  Val  Gly  Glu  Gly  Leu  Ala  Arg  Met  Glu  Leu  Phe  Leu  Phe
                           435                     440                     445

Leu  Thr  Phe  Ile  Leu  Gln  Asn  Phe  Asn  Leu  Lys  Ser  Leu  Ile  Asp  Pro
            450                     455                     460

Lys  Asp  Leu  Asp  Thr  Thr  Pro  Val  Val  Asn  Gly  Phe  Ala  Ser  Val  Pro
            465                     470                     475                     480

Pro  Phe  Tyr  Gln  Leu  Cys  Phe  Ile  Pro  Val
                           485                     490
```

( 2 ) INFORMATION FOR SEQ ID NO:2:

( i ) SEQUENCE CHARACTERISTICS:
        ( A ) LENGTH: 1746 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
CTTCAATGGA  TCCTTTTGTG  GTCCTTGTGC  TCTGTCTCTC  ATGTTTGCTT  CTCCTTTCAA      60
TCTGGAGACA  GAGCTCTGGG  AGAGGAAAAC  TCCCTCCTGG  CCCCACTCCT  CTCCCAGTGA     120
TTGGAAATAT  CCTACAGATA  GATATTAAGG  ATGTCAGCAA  ATCCTTAACC  AATCTCTCAA     180
AAATCTATGG  CCCTGTGTTC  ACTCTGTATT  TTGGCCTGGA  ACGCATGGTG  GTGCTGCATG     240
GATATGAAGT  GGTGAAGGAA  GCCCTGATTG  ATCTTGGAGA  GGAGTTTTCT  GGAAGAGGCC     300
ATTTCCCACT  GGCTGAAAGA  GCTAACAGAG  GATTTGGAAT  CGTTTTCAGC  AATGGAAAGA     360
GATGGAAGGA  GATCCGGCGT  TTCTCCCTCA  TGACGCTGCG  GAATTTTGGG  ATGGGAAGA     420
GGAGCATTGA  GGACCGTGTT  CAAGAGGAAG  CCCGCTGCCT  TGTGGAGGAG  TTGAGAAAAA     480
CCAAGGCTTC  ACCCTGTGAT  CCCACTTTCA  TCCTGGGCTG  TGCTCCCTGC  AATGTGATCT     540
GCTCCATTAT  TTTCCAGAAA  CGTTTCGATT  ATAAAGATCA  GCAATTTCTT  AACTTGATGG     600
AAAAATTGAA  TGAAAACATC  AGGATTGTAA  GCACCCCCTG  GATCCAGATA  TGCAATAATT     660
TTCCCACTAT  CATTGATTAT  TTCCCGGGAA  CCCATAACAA  ATTACTTAAA  AACCTTGCTT     720
TTATGGAAAG  TGATATTTTG  GAGAAAGTAA  AGAACACCA  AGAATCGATG  GACATCAACA     780
ACCCTCGGGA  CTTTATTGAT  TGCTTCCTGA  TCAAAATGGA  GAAGGAAAAG  CAAAACCAAC     840
AGTCTGAATT  CACTATTGAA  AACTTGGTAA  TCACTGCAGC  TGACTTACTT  GGAGCTGGGA     900
CAGAGACAAC  AAGCACAACC  CTGAGATATG  CTCTCCTTCT  CCTGCTGAAG  CACCCAGAGG     960
TCACAGCTAA  AGTCCAGGAA  GAGATTGAAC  GTGTCATTGG  CAGAAACCGG  AGCCCCTGCA    1020
TGCAGGACAG  GGGCCACATG  CCCTACACAG  ATGCTGTGGT  GCACGAGGTC  CAGAGATACA    1080
```

-continued

```
TCGACCTCAT CCCCACCAGC CTGCCCCATG CAGTGACCTG TGACGTTAAA TTCAGAAACT      1140
ACCTCATTCC CAAGGGCACA ACCATATTAA CTTCCCTCAC TTCTGTGCTA CATGACAACA      1200
AAGAATTTCC CAACCCAGAG ATGTTTGACC CTCGTCACTT TCTGGATGAA GGTGGAAATT      1260
TTAAGAAAAG TAACTACTTC ATGCCTTTCT CAGCAGGAAA ACGGATTTGT GTGGGAGAGG      1320
GCCTGGCCCG CATGGAGCTG TTTTTATTCC TGACCTTCAT TTTACAGAAC TTTAACCTGA      1380
AATCTCTGAT TGACCCAAAG GACCTTGACA CAACTCCTGT TGTCAATGGA TTTGCTTCTG      1440
TCCCGCCCTT CTATCAGCTG TGCTTCATTC CTGTCTGAAG AAGCACAGAT GGTCTGGCTG      1500
CTCCTGTGCT GTCCCTGCAG CTCTCTTTCC TCTGGTCCAA ATTTCACTAT CTGTGATGCT      1560
TCTTCTGACC CGTCATCTCA CATTTTCCCT TCCCCAAGA TCTAGTGAAC ATTCAGCCTC       1620
CATTAAAAAA GTTTCACTGT GCAAATATAT CTGCTATTCC CCATACTCTA TAATAGTTAC      1680
ATTGAGTGCC ACATAATGCT GATACTTGTC TAATGTTGAG TTATTAACAT ATTATTATTA      1740
AATAGA                                                                  1746
```

( 2 ) INFORMATION FOR SEQ ID NO:3:

( i ) SEQUENCE CHARACTERISTICS:
        ( A ) LENGTH: 490 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Asp Ser Leu Val Val Leu Val Leu Cys Leu Ser Cys Leu Leu Leu
 1               5                  10                  15

Leu Ser Leu Trp Arg Gln Ser Ser Gly Arg Gly Lys Leu Pro Pro Gly
            20                  25                  30

Pro Thr Pro Leu Pro Val Ile Gly Asn Ile Leu Gln Ile Gly Ile Lys
        35                  40                  45

Asp Ile Ser Lys Ser Leu Thr Asn Leu Ser Lys Val Tyr Gly Pro Val
50                  55                  60

Phe Thr Leu Tyr Phe Gly Leu Lys Pro Ile Val Val Leu His Gly Tyr
65                  70                  75                  80

Glu Ala Val Lys Glu Ala Leu Ile Asp Leu Gly Glu Glu Phe Ser Gly
                85                  90                  95

Arg Gly Ile Phe Pro Leu Ala Glu Arg Ala Asn Arg Gly Phe Gly Ile
            100                 105                 110

Val Phe Ser Asn Gly Lys Lys Trp Lys Glu Ile Arg Arg Phe Ser Leu
        115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
    210                 215                 220
```

-continued

| | | | | | | | | | | | | | | | |
|---|---|---|---|---|---|---|---|---|---|---|---|---|---|---|---|
| Tyr | Phe | Pro | Gly | Thr | His | Asn | Lys | Leu | Leu | Lys | Asn | Val | Ala | Phe | Met |
| 225 | | | | 230 | | | | | 235 | | | | | | 240 |
| Lys | Ser | Tyr | Ile | Leu | Glu | Lys | Val | Lys | Glu | His | Gln | Glu | Ser | Met | Asp |
| | | | | 245 | | | | | 250 | | | | | 255 | |
| Met | Asn | Asn | Pro | Gln | Asp | Phe | Ile | Asp | Cys | Phe | Leu | Met | Lys | Met | Glu |
| | | | 260 | | | | | 265 | | | | | 270 | | |
| Lys | Glu | Lys | His | Asn | Gln | Pro | Ser | Glu | Phe | Thr | Ile | Glu | Ser | Leu | Glu |
| | | 275 | | | | | 280 | | | | | 285 | | | |
| Asn | Thr | Ala | Val | Asp | Leu | Phe | Gly | Ala | Gly | Thr | Glu | Thr | Thr | Ser | Thr |
| | 290 | | | | | 295 | | | | | 300 | | | | |
| Thr | Leu | Arg | Tyr | Ala | Leu | Leu | Leu | Leu | Leu | Lys | His | Pro | Glu | Val | Thr |
| 305 | | | | | 310 | | | | | 315 | | | | | 320 |
| Ala | Lys | Val | Gln | Glu | Glu | Ile | Glu | Arg | Val | Ile | Gly | Arg | Asn | Arg | Ser |
| | | | | 325 | | | | | 330 | | | | | 335 | |
| Pro | Cys | Met | Gln | Asp | Arg | Ser | His | Met | Pro | Tyr | Thr | Asp | Ala | Val | Val |
| | | | 340 | | | | | 345 | | | | | 350 | | |
| His | Glu | Val | Gln | Arg | Tyr | Leu | Asp | Leu | Leu | Pro | Thr | Ser | Leu | Pro | His |
| | | 355 | | | | | 360 | | | | | 365 | | | |
| Ala | Val | Thr | Cys | Asp | Ile | Lys | Phe | Arg | Asn | Tyr | Leu | Ile | Pro | Lys | Gly |
| | 370 | | | | | 375 | | | | | 380 | | | | |
| Thr | Thr | Ile | Leu | Ile | Ser | Leu | Thr | Ser | Val | Leu | His | Asp | Asn | Lys | Glu |
| 385 | | | | | 390 | | | | | 395 | | | | | 400 |
| Phe | Pro | Asn | Pro | Glu | Met | Phe | Asp | Pro | His | His | Phe | Leu | Asp | Glu | Gly |
| | | | | 405 | | | | | 410 | | | | | 415 | |
| Gly | Asn | Phe | Lys | Lys | Ser | Lys | Tyr | Phe | Met | Pro | Phe | Ser | Ala | Gly | Lys |
| | | | 420 | | | | | 425 | | | | | 430 | | |
| Arg | Ile | Cys | Val | Gly | Glu | Ala | Leu | Ala | Gly | Met | Glu | Leu | Phe | Leu | Phe |
| | | 435 | | | | | 440 | | | | | 445 | | | |
| Leu | Thr | Ser | Ile | Leu | Gln | Asn | Phe | Asn | Leu | Lys | Ser | Leu | Val | Asp | Pro |
| | 450 | | | | | 455 | | | | | 460 | | | | |
| Lys | Asn | Leu | Asp | Thr | Thr | Pro | Val | Val | Asn | Gly | Phe | Ala | Ser | Val | Pro |
| 465 | | | | | 470 | | | | | 475 | | | | | 480 |
| Pro | Phe | Tyr | Gln | Leu | Cys | Phe | Ile | Pro | Val | | | | | | |
| | | | | 485 | | | | | 490 | | | | | | |

( 2 ) INFORMATION FOR SEQ ID NO:4:

( i ) SEQUENCE CHARACTERISTICS:
        ( A ) LENGTH: 1854 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
GAGAAGGCTT CAATGGATTC TCTTGTGGTC CTTGTGCTCT GTCTCTCATG TTTGCTTCTC      60

CTTTCACTCT GGAGACAGAG CTCTGGGAGA GGAAAACTCC CTCCTGGCCC CACTCCTCTC     120

CCAGTGATTG AAATATCCT ACAGATAGGT ATTAAGGACA TCAGCAAATC CTTAACCAAT      180

CTCTCAAAGG TCTATGGCCC TGTGTTCACT CTGTATTTTG GCCTGAAACC CATAGTGGTG     240

CTGCATGGAT ATGAAGCAGT GAAGGAAGCC CTGATTGATC TTGGAGAGGA GTTTCTGGA      300

AGAGGCATTT TCCCACTGGC TGAAAGAGCT AACAGAGGAT TGGAATTGT TTCAGCAAT       360

GGAAAGAAAT GGAAGGAGAT CCGGCGTTTC TCCCTCATGA CGCTGCGGAA TTTTGGGATG     420

GGGAAGAGGA GCATTGAGGA CCGTGTTCAA GAGGAAGCCC GCTGCCTTGT GGAGGAGTTG     480
```

| | | | | |
|---|---|---|---|---|
| AGAAAAACCA | AGGCCTCACC | CTGTGATCCC | ACTTTCATCC | TGGGCTGTGC | TCCCTGCAAT | 540 |
| GTGATCTGCT | CCATTATTTT | CCATAAACGT | TTTGATTATA | AAGATCAGCA | ATTTCTTAAC | 600 |
| TTAATGGAAA | AGTTGAATGA | AAACATCAAG | ATTTGAGCA | GCCCTGGAT | CCAGATCTGC | 660 |
| AATAATTTTT | CTCCTATCAT | TGATTACTTC | CCGGGAACTC | ACAACAAATT | ACTTAAAAAC | 720 |
| GTTGCTTTTA | TGAAAAGTTA | TATTTTGGAA | AAAGTAAAAG | AACACCAAGA | ATCAATGGAC | 780 |
| ATGAACAACC | CTCAGGACTT | TATTGATTGC | TTCCTGATGA | AAATGGAGAA | GGAAAAGCAC | 840 |
| AACCAACCAT | CTGAATTTAC | TATTGAAAGC | TTGGAAAACA | CTGCAGTTGA | CTTGTTTGGA | 900 |
| GCTGGGACAG | AGACGACAAG | CACAACCCTG | AGATATGCTC | TCCTTCTCCT | GCTGAAGCAC | 960 |
| CCAGAGGTCA | CAGCTAAAGT | CCAGGAAGAG | ATTGAACGTG | TGATTGGCAG | AAACCGGAGC | 1020 |
| CCCTGCATGC | AAGACAGGAG | CCACATGCCC | TACACAGATG | CTGTGGTGCA | CGAGGTCCAG | 1080 |
| AGATACCTTG | ACCTTCTCCC | CACCAGCCTG | CCCCATGCAG | TGACCTGTGA | CATTAAATTC | 1140 |
| AGAAACTATC | TCATTCCCAA | GGGCACAACC | ATATTAATTT | CCCTGACTTC | TGTGCTACAT | 1200 |
| GACAACAAAG | AATTTCCCAA | CCCAGAGATG | TTTGACCCTC | ATCACTTTCT | GGATGAAGGT | 1260 |
| GGCAATTTTA | AGAAAAGTAA | ATACTTCATG | CCTTTCTCAG | CAGGAAAACG | GATTTGTGTG | 1320 |
| GGAGAAGCCC | TGGCCGGCAT | GGAGCTGTTT | TTATTCCTGA | CCTCCATTTT | ACAGAACTTT | 1380 |
| AACCTGAAAT | CTCTGGTTGA | CCCAAAGAAC | CTTGACACCA | CTCCAGTTGT | CAATGGTTTT | 1440 |
| GCCTCTGTGC | CGCCCTTCTA | CCAGCTGTGC | TTCATTCCTG | TCTGAAGAAG | AGCAGATGGC | 1500 |
| CTGGCTGCTG | CTGTGCAGTC | CCTGCAGCTC | TCTTTCCTCT | GGGGCATTAT | CCATCTTTCA | 1560 |
| CTATCTGTAA | TGCCTTTTCT | CACCTGTCAT | CTCACATTTT | CCCTTCCCTG | AAGATCTAGT | 1620 |
| GAACATTCGA | CCTTCATTAC | GGAGAGTTTC | CTATGTTTCA | CTGTGCAAAT | ATATCTGCTA | 1680 |
| TTCTCCATAC | TCTGTAACAG | TTGCATTGAC | TGTCACATAA | TGCTCATACT | TATCTAATGT | 1740 |
| TGAGTTATTA | ATATGTTATT | ATTAAATAGA | GAAATATGAT | TTGTGTATTA | TAATTCAAAG | 1800 |
| GCATTTCTTT | TCTGCATGTT | CTAAATAAAA | AGCATTATTA | TTTGCTGAAA | AAAA | 1854 |

( 2 ) INFORMATION FOR SEQ ID NO:5:

( i ) SEQUENCE CHARACTERISTICS:
( A ) LENGTH: 490 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

```
Met Asp Pro Ala Val Ala Leu Val Leu Cys Leu Ser Cys Leu Phe Leu
 1               5                  10                  15

Leu Ser Leu Trp Arg Gln Ser Ser Gly Arg Gly Arg Leu Pro Ser Gly
            20                  25                  30

Pro Thr Pro Leu Pro Ile Ile Gly Asn Ile Leu Gln Leu Asp Val Lys
        35                  40                  45

Asp Met Ser Lys Ser Leu Thr Asn Phe Ser Lys Val Tyr Gly Pro Val
    50                  55                  60

Phe Thr Val Tyr Phe Gly Leu Lys Pro Ile Val Leu His Gly Tyr
65                  70                  75                  80

Glu Ala Val Lys Glu Ala Leu Ile Asp His Gly Glu Glu Phe Ser Gly
                85                  90                  95

Arg Gly Ser Phe Pro Val Ala Glu Lys Val Asn Lys Gly Leu Gly Ile
                100                 105                 110
```

| | | | | | | | | | | | | | |
|---|---|---|---|---|---|---|---|---|---|---|---|---|---|
| Leu | Phe | Ser 115 | Asn | Gly | Lys | Arg | Trp 120 | Lys | Glu | Ile | Arg 125 | Phe | Cys | Leu |
| Met | Thr 130 | Leu | Arg | Asn | Phe 135 | Met | Gly | Lys | Arg 140 | Ser | Ile | Glu | Asp | Arg |
| Val 145 | Gln | Glu | Glu | Ala | Arg 150 | Cys | Leu | Val | Glu 155 | Leu | Arg | Lys | Thr | Asn 160 |
| Ala | Ser | Pro | Cys | Asp 165 | Pro | Thr | Phe | Ile | Leu 170 | Gly | Cys | Ala | Pro | Cys 175 | Asn |
| Val | Ile | Cys | Ser 180 | Val | Ile | Phe | His | Asp 185 | Arg | Phe | Asp | Tyr | Lys 190 | Asp | Gln |
| Arg | Phe | Leu 195 | Asn | Leu | Met | Glu | Lys 200 | Phe | Asn | Glu | Asn | Leu 205 | Arg | Ile | Leu |
| Ser | Ser 210 | Pro | Trp | Ile | Gln | Val 215 | Cys | Asn | Asn | Phe | Pro 220 | Ala | Leu | Ile | Asp |
| Tyr 225 | Leu | Pro | Gly | Ser | His 230 | Asn | Lys | Ile | Ala | Glu 235 | Asn | Phe | Ala | Tyr | Ile 240 |
| Lys | Ser | Tyr | Val | Leu 245 | Glu | Arg | Ile | Lys | Glu 250 | His | Gln | Glu | Ser | Leu 255 | Asp |
| Met | Asn | Ser | Ala 260 | Arg | Asp | Phe | Ile | Asp 265 | Cys | Phe | Leu | Ile | Lys 270 | Met | Glu |
| Gln | Glu | Lys 275 | His | Asn | Gln | Gln | Ser 280 | Glu | Phe | Thr | Val | Glu 285 | Ser | Leu | Ile |
| Ala | Thr 290 | Val | Thr | Asp | Met | Phe 295 | Gly | Ala | Gly | Thr | Glu 300 | Thr | Thr | Ser | Thr |
| Thr 305 | Leu | Arg | Tyr | Gly | Leu 310 | Leu | Leu | Leu | Leu | Lys 315 | Tyr | Pro | Glu | Val | Thr 320 |
| Ala | Lys | Val | Gln | Glu 325 | Glu | Ile | Glu | Cys | Val 330 | Val | Gly | Arg | Asn | Arg 335 | Ser |
| Pro | Cys | Met | Gln 340 | Asp | Arg | Ser | His | Met 345 | Pro | Tyr | Thr | Asp | Ala 350 | Val | Val |
| His | Glu | Ile 355 | Gln | Arg | Tyr | Ile | Asp 360 | Leu | Leu | Pro | Thr | Asn 365 | Leu | Pro | His |
| Ala | Val 370 | Thr | Cys | Asp | Val | Lys 375 | Phe | Lys | Asn | Tyr | Leu 380 | Ile | Pro | Lys | Gly |
| Thr 385 | Thr | Ile | Ile | Thr | Ser 390 | Leu | Thr | Ser | Val | Leu 395 | His | Asn | Asp | Lys | Glu 400 |
| Phe | Pro | Asn | Pro | Glu 405 | Met | Phe | Asp | Pro | Gly 410 | His | Phe | Leu | Asp | Lys 415 | Ser |
| Gly | Asn | Phe | Lys 420 | Lys | Ser | Asp | Tyr | Phe 425 | Met | Pro | Phe | Ser | Ala 430 | Gly | Lys |
| Arg | Met | Cys 435 | Met | Gly | Glu | Gly | Leu 440 | Ala | Arg | Met | Glu | Leu 445 | Phe | Leu | Phe |
| Leu | Thr 450 | Thr | Ile | Leu | Gln | Asn 455 | Phe | Asn | Leu | Lys | Ser 460 | Gln | Val | Asp | Pro |
| Lys 465 | Asp | Ile | Asp | Ile | Thr 470 | Pro | Ile | Ala | Asn | Ala 475 | Phe | Gly | Arg | Val | Pro 480 |
| Pro | Leu | Tyr | Gln | Leu 485 | Cys | Phe | Ile | Pro | Val 490 | | | | | | |

( 2 ) INFORMATION FOR SEQ ID NO:6:

( i ) SEQUENCE CHARACTERISTICS:
( A ) LENGTH: 2009 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

| | | | | | | |
|---|---|---|---|---|---|---|
| GGCACCGGAA | AGAACAAGAA | AAAAGAACAC | CTTATTTTTA | TCTTCTTCAG | TGAGCCAATG | 60 |
| TTCATTCAAA | AGAGAGATTA | AAGTGCTTTT | TGCTGACTAG | TCACAGTCAG | AGTCAGAATC | 120 |
| ACAGGTGGAT | TAGTAGGGAG | TGTTATAAAA | GCCTTGAAGT | GAAAGCCCGC | AGTTGTCTTA | 180 |
| CTAAGAAGAG | AAGCCTTCAA | TGGATCCAGC | TGTGGCTCTG | GTGCTCTGTC | TCTCCTGTTT | 240 |
| GTTTCTCCTT | TCACTCTGGA | GGCAGAGCTC | TGGAAGAGGG | AGGCTCCCGT | CTGGCCCCAC | 300 |
| TCCTCTCCCG | ATTATTGGAA | ATATCCTGCA | GTTAGATGTT | AAGGACATGA | GCAAATCCTT | 360 |
| AACCAATTTC | TCAAAAGTCT | ATGGCCCTGT | GTTCACTGTG | TATTTTGGCC | TGAAGCCCAT | 420 |
| TGTGGTGTTG | CATGGATATG | AAGCAGTGAA | GGAGGCCCTG | ATTGATCATG | GAGAGGAGTT | 480 |
| TTCTGGAAGA | GGAAGTTTTC | CAGTGGCTGA | AAAAGTTAAC | AAAGGACTTG | GAATCCTTTT | 540 |
| CAGCAATGGA | AAGAGATGGA | AGGAGATCCG | GCGTTTCTGC | CTCATGACTC | TGCGGAATTT | 600 |
| TGGGATGGGG | AAGAGGAGCA | TCGAGGACCG | TGTTCAAGAG | GAAGCCCGCT | GCCTTGTGGA | 660 |
| GGAGTTGAGA | AAAACCAATG | CCTCACCCTG | TGATCCCACT | TTCATCCTGG | GCTGTGCTCC | 720 |
| CTGCAATGTG | ATCTGCTCTG | TTATTTTCCA | TGATCGATTT | GATTATAAAG | ATCAGAGGTT | 780 |
| TCTTAACTTG | ATGGAAAAAT | TCAATGAAAA | CCTCAGGATT | CTGAGCTCTC | CATGGATCCA | 840 |
| GGTCTGCAAT | AATTTCCCTG | CTCTCATCGA | TTATCTCCCA | GGAAGTCATA | ATAAAATAGC | 900 |
| TGAAAATTTT | GCTTACATTA | AAGTTATGT | ATTGGAGAGA | ATAAAAGAAC | ATCAAGAATC | 960 |
| CCTGGACATG | AACAGTGCTC | GGGACTTTAT | TGATTGTTTC | CTGATCAAAA | TGGAACAGGA | 1020 |
| AAAGCACAAT | CAACAGTCTG | AATTTACTGT | TGAAAGCTTG | ATAGCCACTG | TAACTGATAT | 1080 |
| GTTTGGGGCT | GGAACAGAGA | CAACGAGCAC | CACTCTGAGA | TATGGACTCC | TGCTCCTGCT | 1140 |
| GAAGTACCCA | GAGGTCACAG | CTAAAGTCCA | GGAAGAGATT | GAATGTGTAG | TTGGCAGAAA | 1200 |
| CCGGAGCCCC | TGTATGCAGG | ACAGGAGTCA | CATGCCCTAC | ACAGATGCTG | TGGTGCACGA | 1260 |
| GATCCAGAGA | TACATTGACC | TCCTCCCCAC | CAACCTGCCC | CATGCAGTGA | CCTGTGATGT | 1320 |
| TAAATTCAAA | AACTACCTCA | TCCCCAAGGG | CACGACCATA | ATAACATCCC | TGACTTCTGT | 1380 |
| GCTGCACAAT | GACAAAGAAT | TCCCCAACCC | AGAGATGTTT | GACCCTGGCC | ACTTTCTGGA | 1440 |
| TAAGAGTGGC | AACTTTAAGA | AAAGTGACTA | CTTCATGCCT | TTCTCAGCAG | GAAAACGGAT | 1500 |
| GTGTATGGGA | GAGGGCCTGG | CCCGCATGGA | GCTGTTTTA | TTCCTGACCA | CCATTTTGCA | 1560 |
| GAACTTTAAC | CTGAAATCTC | AGGTTGACCC | AAAGGATATT | GACATCACCC | CCATTGCCAA | 1620 |
| TGCATTTGGT | CGTGTGCCAC | CCTTGTACCA | GCTCTGCTTC | ATTCCTGTCT | GAAGAAGGGC | 1680 |
| AGATAGTTTG | GCTGCTCCTG | TGCTGTCACC | TGCAATTCTC | CCTTATCAGG | GCCATTAGCC | 1740 |
| TCTCCCTTCT | CTCTGTGAGG | GATATTTTCT | CTGACTTGTC | AATCCACATC | TTCCCATTCC | 1800 |
| CTCAAGATCC | AATGAACATC | CAACCTCCAT | TAAAGAGAGT | TTCTTGGGTC | ACTTCCTAAA | 1860 |
| TATATCTGCT | ATTCTCCATA | CTCTGTATCA | CTTGTATTGA | CCACCACATA | TGCTAATACC | 1920 |
| TATCTACTGC | TGAGTTGTCA | GTATGTTATC | ACTAGAAAAC | AAAGAAAAAT | GATTAATAAA | 1980 |
| TGACAATTCA | GAGCCAAAAA | AAAAAAAAA | | | | 2009 |

( 2 ) INFORMATION FOR SEQ ID NO:7:

( i ) SEQUENCE CHARACTERISTICS:
( A ) LENGTH: 490 amino acids
( B ) TYPE: amino acid
( C ) STRANDEDNESS: single ( D ) TOPOLOGY: linear ( i i ) MOLECULE TYPE: protein ( x i ) SEQUENCE DESCRIPTION: SEQ ID NO:7:

| Met | Glu | Pro | Phe | Val | Val | Leu | Val | Leu | Cys | Leu | Ser | Phe | Met | Leu | Leu |
|---|---|---|---|---|---|---|---|---|---|---|---|---|---|---|---|
| 1 | | | | 5 | | | | | 10 | | | | | 15 | |
| Phe | Ser | Leu | Trp | Arg | Gln | Ser | Cys | Arg | Arg | Arg | Lys | Leu | Pro | Pro | Gly |
| | | | 20 | | | | | 25 | | | | | 30 | | |
| Pro | Thr | Pro | Leu | Pro | Ile | Ile | Gly | Asn | Met | Leu | Gln | Ile | Asp | Val | Lys |
| | | 35 | | | | | 40 | | | | | 45 | | | |
| Asp | Ile | Cys | Lys | Ser | Phe | Thr | Asn | Phe | Ser | Lys | Val | Tyr | Gly | Pro | Val |
| | 50 | | | | | 55 | | | | | 60 | | | | |
| Phe | Thr | Val | Tyr | Phe | Gly | Met | Asn | Pro | Ile | Val | Val | Phe | His | Gly | Tyr |
| 65 | | | | | 70 | | | | | 75 | | | | | 80 |
| Glu | Ala | Val | Lys | Glu | Ala | Leu | Ile | Asp | Asn | Gly | Glu | Glu | Phe | Ser | Gly |
| | | | | 85 | | | | | 90 | | | | | 95 | |
| Arg | Gly | Asn | Ser | Pro | Ile | Ser | Gln | Arg | Ile | Thr | Lys | Gly | Leu | Gly | Ile |
| | | | 100 | | | | | 105 | | | | | 110 | | |
| Ile | Ser | Ser | Asn | Gly | Lys | Arg | Trp | Lys | Glu | Ile | Arg | Arg | Phe | Ser | Leu |
| | | 115 | | | | | 120 | | | | | 125 | | | |
| Thr | Asn | Leu | Arg | Asn | Phe | Gly | Met | Gly | Lys | Arg | Ser | Ile | Glu | Asp | Arg |
| | 130 | | | | | 135 | | | | | 140 | | | | |
| Val | Gln | Glu | Glu | Ala | His | Cys | Leu | Val | Glu | Glu | Leu | Arg | Lys | Thr | Lys |
| 145 | | | | | 150 | | | | | 155 | | | | | 160 |
| Ala | Ser | Pro | Cys | Asp | Pro | Thr | Phe | Ile | Leu | Gly | Cys | Ala | Pro | Cys | Asn |
| | | | | 165 | | | | | 170 | | | | | 175 | |
| Val | Ile | Cys | Ser | Val | Val | Phe | Gln | Lys | Arg | Phe | Asp | Tyr | Lys | Asp | Gln |
| | | | 180 | | | | | 185 | | | | | 190 | | |
| Asn | Phe | Leu | Thr | Leu | Met | Lys | Arg | Phe | Asn | Glu | Asn | Phe | Arg | Ile | Leu |
| | | 195 | | | | | 200 | | | | | 205 | | | |
| Asn | Ser | Pro | Trp | Ile | Gln | Val | Cys | Asn | Asn | Phe | Pro | Leu | Leu | Ile | Asp |
| | 210 | | | | | 215 | | | | | 220 | | | | |
| Cys | Phe | Pro | Gly | Thr | His | Asn | Lys | Val | Leu | Lys | Asn | Val | Ala | Leu | Thr |
| 225 | | | | | 230 | | | | | 235 | | | | | 240 |
| Arg | Ser | Tyr | Ile | Arg | Glu | Lys | Val | Lys | Glu | His | Gln | Ala | Ser | Leu | Asp |
| | | | | 245 | | | | | 250 | | | | | 255 | |
| Val | Asn | Asn | Pro | Arg | Asp | Phe | Met | Asp | Cys | Phe | Leu | Ile | Lys | Met | Glu |
| | | | 260 | | | | | 265 | | | | | 270 | | |
| Gln | Glu | Lys | Asp | Asn | Gln | Lys | Ser | Glu | Phe | Asn | Ile | Glu | Asn | Leu | Val |
| | | 275 | | | | | 280 | | | | | 285 | | | |
| Gly | Thr | Val | Ala | Asp | Leu | Phe | Val | Ala | Gly | Thr | Glu | Thr | Thr | Ser | Thr |
| | 290 | | | | | 295 | | | | | 300 | | | | |
| Thr | Leu | Arg | Tyr | Gly | Leu | Leu | Leu | Leu | Leu | Lys | His | Pro | Glu | Val | Thr |
| 305 | | | | | 310 | | | | | 315 | | | | | 320 |
| Ala | Lys | Val | Gln | Glu | Glu | Ile | Asp | His | Val | Ile | Gly | Arg | His | Arg | Ser |
| | | | | 325 | | | | | 330 | | | | | 335 | |
| Pro | Cys | Met | Gln | Asp | Arg | Ser | His | Met | Pro | Tyr | Thr | Asp | Ala | Val | Val |
| | | | 340 | | | | | 345 | | | | | 350 | | |
| His | Glu | Ile | Gln | Arg | Tyr | Ser | Asp | Leu | Val | Pro | Thr | Gly | Val | Pro | His |
| | | 355 | | | | | 360 | | | | | 365 | | | |
| Ala | Val | Thr | Thr | Asp | Thr | Lys | Phe | Arg | Asn | Tyr | Leu | Ile | Pro | Lys | Gly |
| | 370 | | | | | 375 | | | | | 380 | | | | |
| Thr | Thr | Ile | Met | Ala | Leu | Leu | Thr | Ser | Val | Leu | His | Asp | Asp | Lys | Glu |
| 385 | | | | | 390 | | | | | 395 | | | | | 400 |

```
Phe  Pro  Asn  Pro  Asn  Ile  Phe  Asp  Pro  Gly  His  Phe  Leu  Asp  Lys  Asn
               405                      410                      415

Gly  Asn  Phe  Lys  Lys  Ser  Asp  Tyr  Phe  Met  Pro  Phe  Ser  Ala  Gly  Lys
          420                      425                      430

Arg  Ile  Cys  Ala  Gly  Glu  Gly  Leu  Ala  Arg  Met  Glu  Leu  Phe  Leu  Phe
          435                      440                      445

Leu  Thr  Thr  Ile  Leu  Gln  Asn  Phe  Asn  Leu  Lys  Ser  Val  Asp  Asp  Leu
     450                      455                 460

Lys  Asn  Leu  Asn  Thr  Thr  Ala  Val  Thr  Lys  Gly  Ile  Val  Ser  Leu  Pro
465                      470                 475                           480

Pro  Ser  Tyr  Gln  Ile  Cys  Phe  Ile  Pro  Val
               485                      490
```

( 2 ) INFORMATION FOR SEQ ID NO:8:

( i ) SEQUENCE CHARACTERISTICS:
        ( A ) LENGTH: 1829 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
AATGGAACCT  TTTGTGGTCC  TGGTGCTGTG  TCTCTCTTTT  ATGCTTCTCT  TTTCACTCTG    60
GAGACAGAGC  TGTAGGAGAA  GGAAGCTCCC  TCCTGGCCCC  ACTCCTCTTC  CTATTATTGG   120
AAATATGCTA  CAGATAGATG  TTAAGGACAT  CTGCAAATCT  TTCACCAATT  TCTCAAAAGT   180
CTATGGTCCT  GTGTTCACCG  TGTATTTTGG  CATGAATCCC  ATAGTGGTGT  TCATGGATA    240
TGAGGCAGTG  AAGGAAGCCC  TGATTGATAA  TGGAGAGGAG  TTTTCTGGAA  GAGGCAATTC   300
CCCAATATCT  CAAAGAATTA  CTAAAGGACT  TGGAATCATT  CCAGCAATG   GAAAGAGATG   360
GAAGGAGATC  CGGCGTTTCT  CCCTCACAAA  CTTGCGGAAT  TTGGGATGG   GGAAGAGGAG   420
CATTGAGGAC  CGTGTTCAAG  AGGAAGCTCA  CTGCCTTGTG  GAGGAGTTGA  GAAAAACCAA   480
GGCTTCACCC  TGTGATCCCA  CTTTCATCCT  GGGCTGTGCT  CCCTGCAATG  TGATCTGCTC   540
CGTTGTTTTC  CAGAAACGAT  TTGATTATAA  AGATCAGAAT  TTCTCACCC   TGATGAAAAG   600
ATTCAATGAA  AACTTCAGGA  TTCTGAACTC  CCCATGGATC  CAGGTCTGCA  ATAATTTCCC   660
TCTACTCATT  GATTGTTTCC  CAGGAACTCA  CAACAAAGTG  CTTAAAAATG  TTGCTCTTAC   720
ACGAAGTTAC  ATTAGGGAGA  AAGTAAAAGA  CACCAAGCA   TCACTGGATG  TTAACAATCC   780
TCGGGACTTT  ATGGATTGCT  TCCTGATCAA  AATGGAGCAG  GAAAAGGACA  ACCAAAAGTC   840
AGAATTCAAT  ATTGAAAACT  TGGTTGGCAC  TGTAGCTGAT  CTATTTGTTG  CTGGAACAGA   900
GACAACAAGC  ACCACTCTGA  GATATGGACT  CCTGCTCCTG  CTGAAGCACC  CAGAGGTCAC   960
AGCTAAAGTC  CAGGAAGAGA  TTGATCATGT  AATTGGCAGA  CACAGGAGCC  CCTGCATGCA  1020
GGATAGGAGC  CACATGCCTT  ACACTGATGC  TGTAGTGCAC  GAGATCCAGA  GATACAGTGA  1080
CCTTGTCCCC  ACCGGTGTGC  CCCATGCAGT  GACCACTGAT  ACTAAGTTCA  GAAACTACCT  1140
CATCCCCAAG  GGCACAACCA  TAATGGCATT  ACTGACTTCC  GTGCTACATG  ATGACAAAGA  1200
ATTTCCTAAT  CCAAATATCT  TTGACCCTGG  CCACTTTCTA  GATAAGAATG  GCAACTTTAA  1260
GAAAAGTGAC  TACTTCATGC  CTTTCTCAGC  AGGAAAACGA  ATTTGTGCAG  GAGAAGGACT  1320
TGCCCGCATG  GAGCTATTTT  TATTTCTAAC  CACAATTTTA  CAGAACTTTA  ACCTGAAATC  1380
TGTTGATGAT  TTAAAGAACC  TCAATACTAC  TGCAGTTACC  AAAGGGATTG  TTTCTCTGCC  1440
```

```
ACCCTCATAC CAGATCTGCT TCATCCCTGT CTGAAGAATG CTAGCCCATC TGGCTGCTGA      1500

TCTGCTATCA CCTGCAACTC TTTTTTTATC AAGGACATTC CCACTATTAT GTCTTCTCTG      1560

ACCTCTCATC AAATCTTCCC ATTCACTCAA TATCCCATAA GCATCCAAAC TCCATTAAGG      1620

AGAGTTGTTC AGGTCACTGC ACAAATATAT CTGCAATTAT TCATACTCTG TAACACTTGT      1680

ATTAATTGCT GCATATGCTA ATACTTTTCT AATGCTGACT TTTTAATATG TTATCACTGT      1740

AAAACACAGA AAAGTGATTA ATGAATGATA ATTTAGTCCA TTTCTTTTGT GAATGTGCTA      1800

AATAAAAAGT GTTATTAATT GCTGGTTCA                                        1829
```

( 2 ) INFORMATION FOR SEQ ID NO:9:

( i ) SEQUENCE CHARACTERISTICS:
    ( A ) LENGTH: 490 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:9:

```
Met Asp Ser Leu Val Val Leu Val Leu Cys Leu Ser Cys Leu Leu Leu
  1               5                  10                  15

Leu Ser Leu Trp Arg Gln Ser Ser Arg Gly Lys Leu Pro Pro Gly
             20                  25                  30

Pro Thr Pro Leu Pro Val Ile Gly Asn Ile Leu Gln Ile Gly Ile Lys
         35                  40                  45

Asp Ile Ser Lys Ser Leu Thr Asn Leu Ser Lys Val Tyr Gly Pro Val
     50                  55                  60

Phe Thr Leu Tyr Phe Gly Leu Lys Pro Ile Val Val Leu His Gly Tyr
 65                  70                  75                  80

Glu Ala Val Lys Glu Ala Leu Ile Asp Leu Gly Glu Glu Phe Ser Gly
                 85                  90                  95

Arg Gly Ile Phe Pro Leu Ala Glu Arg Ala Asn Arg Gly Phe Gly Ile
            100                 105                 110

Val Phe Ser Asn Gly Lys Lys Trp Lys Glu Ile Arg Arg Phe Ser Leu
        115                 120                 125

Met Thr Leu Arg Asn Phe Gly Met Gly Lys Arg Ser Ile Glu Asp Arg
130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
    210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270

Lys Glu Lys His Asn Gln Pro Ser Glu Phe Thr Ile Glu Ser Leu Glu
        275                 280                 285
```

|  |  |  |  |  |  |  |  |  |  |  |  |  |  |  |
|---|---|---|---|---|---|---|---|---|---|---|---|---|---|---|
| Asn | Thr 290 | Ala | Val | Asp | Leu | Phe 295 | Gly | Ala | Gly | Thr 300 | Thr | Thr | Ser | Thr |
| Thr 305 | Leu | Arg | Tyr | Ala | Leu 310 | Leu | Leu | Leu | Leu | Lys 315 | His | Pro | Glu | Val Thr 320 |
| Ala | Lys | Val | Gln 325 | Glu | Ile | Glu | Arg | Val 330 | Ile | Gly | Arg | Asn 335 | Arg | Ser |
| Pro | Cys | Met | Gln 340 | Asp | Arg | Ser | His | Met 345 | Pro | Tyr | Thr | Asp | Ala 350 | Val Val |
| His | Glu | Val 355 | Gln | Arg | Tyr | Ile | Asp 360 | Leu | Leu | Pro | Thr | Ser 365 | Leu | Pro His |
| Ala | Val 370 | Thr | Cys | Asp | Ile | Lys 375 | Phe | Arg | Asn | Tyr | Leu 380 | Ile | Pro | Lys Gly |
| Thr 385 | Thr | Ile | Leu | Ile | Ser 390 | Leu | Thr | Ser | Val | Leu 395 | His | Asp | Asn | Lys Glu 400 |
| Phe | Pro | Asn | Pro | Glu 405 | Met | Phe | Asp | Pro | His 410 | His | Phe | Leu | Asp | Glu 415 Gly |
| Gly | Asn | Phe | Lys 420 | Lys | Ser | Lys | Tyr | Phe 425 | Met | Pro | Phe | Ser | Ala 430 | Gly Lys |
| Arg | Ile | Cys 435 | Val | Gly | Glu | Ala | Leu 440 | Ala | Gly | Met | Glu | Leu 445 | Phe | Leu Phe |
| Leu | Thr 450 | Ser | Ile | Leu | Gln | Asn 455 | Phe | Asn | Leu | Lys | Ser 460 | Leu | Val | Asp Pro |
| Lys 465 | Asn | Leu | Asp | Thr | Thr 470 | Pro | Val | Val | Asn | Gly 475 | Phe | Ala | Ser | Val Pro 480 |
| Pro | Phe | Tyr | Gln | Leu 485 | Cys | Phe | Ile | Pro | Val 490 | | | | | |

( 2 ) INFORMATION FOR SEQ ID NO:10:

( i ) SEQUENCE CHARACTERISTICS:
        ( A ) LENGTH: 1852 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
GAAGGCTTCA ATGGATTCTC TTGTGGTCCT TGTGCTCTGT CTCTCATGTT TGCTTCTCCT      60
TTCACTCTGG AGACAGAGCT CTGGGAGAGG AAAACTCCCT CCTGGCCCCA CTCCTCTCCC     120
AGTGATTGGA AATATCCTAC AGATAGGTAT TAAGGACATC AGCAAATCCT TAACCAATCT     180
CTCAAAGGTC TATGGCCCTG TGTTCACTCT GTATTTGGC CTGAAACCCA TAGTGGTGCT      240
GCATGGATAT GAAGCAGTGA AGGAAGCCCT GATTGATCTT GGAGAGGAGT TTTCTGGAAG     300
AGGCATTTTC CCACTGGCTG AAAGAGCTAA CAGAGGATTT GGAATTGTTT TCAGCAATGG     360
AAAGAAATGG AAGGAGATCC GGCGTTTCTC CCTCATGACG CTGCGGAATT TTGGGATGGG     420
GAAGAGGAGC ATTGAGGACC GTGTTCAAGA GGAAGCCCGC TGCCTTGTGG AGGAGTTGAG     480
AAAAACCAAG GCCTCACCCT GTGATCCCAC TTTCATCCTG GGCTGTGCTC CCTGCAATGT     540
GATCTGCTCC ATTATTTTCC ATAAACGTTT TGATTATAAA GATCAGCAAT TTCTTAACTT     600
AATGGAAAAG TTGAATGAAA ACATCAAGAT TTGAGCAGC CCCTGGATCC AGATCTGCAA      660
TAATTTTTCT CCTATCATTG ATTACTTCCC GGGAACTCAC AACAAATTAC TTAAAAACGT     720
TGCTTTTATG AAAAGTTATA TTTTGGAAAA AGTAAAAGAA CACCAAGAAT CAATGGACAT     780
GAACAACCCT CAGGACTTTA TTGATTGCTT CCTGATGAAA ATGGAGAAGG AAAAGCACAA     840
```

```
CCAACCATCT GAATTTACTA TTGAAAGCTT GGAAAACACT GCAGTTGACT TGTTTGGAGC    900
TGGGACAGAG ACGACAAGCA CAACCCTGAG ATATGCTCTC CTTCTCCTGC TGAAGCACCC    960
AGAGGTCACA GCTAAAGTCC AGGAAGAGAT TGAACGTGTG ATTGGCAGAA ACCGGAGCCC   1020
CTGCATGCAA GACAGGAGCC ACATGCCCTA CACAGATGCT GTGGTGCACG AGGTCCAGAG   1080
ATACATTGAC CTTCTCCCCA CCAGCCTGCC CCATGCAGTG ACCTGTGACA TTAAATTCAG   1140
AAACTATCTC ATTCCCAAGG GCACAACCAT ATTAATTTCC CTGACTTCTG TGCTACATGA   1200
CAACAAAGAA TTTCCCAACC CAGAGATGTT TGACCCTCAT CACTTTCTGG ATGAAGGTGG   1260
CAATTTTAAG AAAAGTAAAT ACTTCATGCC TTTCTCAGCA GGAAAACGGA TTTGTGTGGG   1320
AGAAGCCCTG GCCGGCATGG AGCTGTTTTT ATTCCTGACC TCCATTTTAC AGAACTTTAA   1380
CCTGAAATCT CTGGTTGACC CAAAGAACCT TGACACCACT CCAGTTGTCA ATGGATTTGC   1440
CTCTGTGCCG CCCTTCTACC AGCTGTGCTT CATTCCTGTC TGAAGAAGAG CAGATGGCCT   1500
GGCTGCTGCT GTGCAGTCCC TGCAGCTCTC TTTCCTCTGG GGCATTATCC ATCTTTCACT   1560
ATCTGTAATG CCTTTTCTCA CCTGTCATCT CACATTTTCC CTTCCCTGAA GATCTAGTGA   1620
ACATTCGACC TCCATTACGG AGAGTTTCCT ATGTTTCACT GTGCAAATAT ATCTGCTATT   1680
CTCCATACTC TGTAACAGTT GCATTGACTG TCACATAATG CTCATACTTA TCTAATGTTG   1740
AGTTATTAAT ATGTTATTAT TAAATAGAGA AATATGATTT GTGTATTATA ATTCAAAGGC   1800
ATTTCTTTTC TGCATGTTCT AAATAAAAAG CATTATTATT TGCTGAAAAA AA           1852
```

( 2 ) INFORMATION FOR SEQ ID NO:11:

( i ) SEQUENCE CHARACTERISTICS:
( A ) LENGTH: 490 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

```
Met Asp Pro Ala Val Ala Leu Val Leu Cys Leu Ser Cys Leu Phe Leu
 1               5                  10                  15
Leu Ser Leu Trp Arg Gln Ser Ser Gly Arg Gly Arg Leu Pro Ser Gly
                20                  25                  30
Pro Thr Pro Leu Pro Ile Ile Gly Asn Ile Leu Gln Leu Asp Val Lys
            35                  40                  45
Asp Met Ser Lys Ser Leu Thr Asn Phe Ser Lys Val Tyr Gly Pro Val
        50                  55                  60
Phe Thr Val Tyr Phe Gly Leu Lys Pro Ile Val Val Leu His Gly Tyr
 65                  70                  75                  80
Glu Ala Val Lys Glu Ala Leu Ile Asp His Gly Glu Glu Phe Ser Gly
                85                  90                  95
Arg Gly Ser Phe Pro Val Ala Glu Lys Val Asn Lys Gly Leu Gly Ile
               100                 105                 110
Leu Phe Ser Asn Gly Lys Arg Trp Lys Glu Ile Arg Arg Phe Cys Leu
            115                 120                 125
Met Thr Leu Arg Asn Phe Gly Met Gly Lys Arg Ser Ile Glu Asp Arg
        130                 135                 140
Val Gln Glu Glu Ala Arg Cys Leu Val Glu Glu Leu Arg Lys Thr Asn
145                 150                 155                 160
Ala Ser Pro Cys Asp Pro Thr Phe Ile Leu Gly Cys Ala Pro Cys Asn
                165                 170                 175
```

| | | | | | | | | | | | | | |
|---|---|---|---|---|---|---|---|---|---|---|---|---|---|
|Val|Ile|Cys|Ser|Val|Ile|Phe|His|Asp|Arg|Phe|Asp|Tyr|Lys|Asp|Gln|
| | | |180| | | |185| | | |190| | |

Arg Phe Leu Asn Leu Met Glu Lys Phe Asn Glu Asn Leu Arg Ile Leu
            195             200                205

Ser Ser Pro Trp Ile Gln Val Cys Asn Asn Phe Pro Ala Leu Ile Asp
        210             215             220

Tyr Leu Pro Gly Ser His Asn Lys Ile Ala Glu Asn Phe Ala Tyr Ile
225                 230             235                     240

Lys Ser Tyr Val Leu Glu Arg Ile Lys Glu His Gln Glu Ser Leu Asp
                245             250                 255

Met Asn Ser Ala Arg Asp Phe Ile Asp Cys Phe Leu Ile Lys Met Glu
            260             265             270

Gln Glu Lys His Asn Gln Gln Ser Glu Phe Thr Val Glu Ser Leu Ile
            275             280             285

Ala Thr Val Thr Asp Met Phe Gly Ala Gly Thr Glu Thr Thr Ser Thr
    290             295             300

Thr Leu Arg Tyr Gly Leu Leu Leu Leu Leu Lys Tyr Pro Glu Val Thr
305             310             315                     320

Ala Lys Val Gln Glu Glu Ile Glu Cys Val Val Gly Arg Asn Arg Ser
                325             330             335

Pro Cys Met Gln Asp Arg Ser His Met Pro Tyr Thr Asp Ala Val Val
            340             345             350

His Glu Ile Gln Arg Tyr Ile Asp Leu Leu Pro Thr Asn Leu Pro His
            355             360             365

Ala Val Thr Cys Asp Val Lys Phe Lys Asn Tyr Leu Ile Pro Lys Gly
    370             375             380

Met Thr Ile Ile Thr Ser Leu Thr Ser Val Leu His Asn Asp Lys Glu
385             390             395                     400

Phe Pro Asn Pro Glu Met Phe Asp Pro Gly His Phe Leu Asp Lys Ser
                405             410             415

Gly Asn Phe Lys Lys Ser Asp Tyr Phe Met Pro Phe Ser Ala Gly Lys
            420             425             430

Arg Met Cys Met Gly Glu Gly Leu Ala Arg Met Glu Leu Phe Leu Phe
        435             440             445

Leu Thr Thr Ile Leu Gln Asn Phe Asn Leu Lys Ser Gln Val Asp Pro
    450             455             460

Lys Asp Ile Asp Ile Thr Pro Ile Ala Asn Ala Phe Gly Arg Val Pro
465             470             475                     480

Pro Leu Tyr Gln Leu Cys Phe Ile Pro Val
            485             490

(2) INFORMATION FOR SEQ ID NO:12:

(i) SEQUENCE CHARACTERISTICS:
        (A) LENGTH: 2258 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
AGTGAAAGCC CGCAGTTGTC TTACTAAGAA GAGAAGCCTT CAATGGATCC AGCTGTGGCT      60
CTGGTGCTCT GTCTCTCCTG TTTGTTTCTC CTTTCACTCT GGAGGCAGAG CTCTGGAAGA     120
GGGAGGCTCC CGTCTGGCCC CACTCCTCTC CCGATTATTG GAAATATCCT GCAGTTAGAT     180
```

-continued

| | | | | | |
|---|---|---|---|---|---|
|GTTAAGGACA|TGAGCAAATC|CTTAACCAAT|TTCTCAAAAG|TCTATGGCCC|TGTGTTCACT|240|
|GTGTATTTTG|GCCTGAAGCC|CATTGTGGTG|TTGCATGGAT|ATGAAGCAGT|GAAGGAGGCC|300|
|CTGATTGATC|ATGGAGAGGA|GTTTCTGGA|AGAGGAAGTT|TTCCAGTGGC|TGAAAAAGTT|360|
|AACAAAGGAC|TTGGAATCCT|TTTCAGCAAT|GGAAAGAGAT|GGAAGGAGAT|CCGGCGTTTC|420|
|TGCCTCATGA|CTCTGCGGAA|TTTTGGGATG|GGGAAGAGGA|GCATCGAGGA|CCGTGTTCAA|480|
|GAGGAAGCCC|GCTGCCTTGT|GGAGGAGTTG|AGAAAAACCA|ATGCCTCACC|CTGTGATCCC|540|
|ACTTTCATCC|TGGGCTGTGC|TCCCTGCAAT|GTGATCTGCT|CTGTTATTTT|CCATGATCGA|600|
|TTTGATTATA|AAGATCAGAG|GTTTCTTAAC|TTGATGGAAA|AATTCAATGA|AAACCTCAGG|660|
|ATTCTGAGCT|CTCCATGGAT|CCAGGTCTGC|AATAATTTCC|CTGCTCTCAT|CGATTATCTC|720|
|CCAGGAAGTC|ATAATAAAT|AGCTGAAAAT|TTTGCTTACA|TTAAAAGTTA|TGTATTGGAG|780|
|AGAATAAAAG|AACATCAAGA|ATCCCTGGAC|ATGAACAGTG|CTCGGGACTT|TATTGATTGT|840|
|TTCCTGATCA|AAATGGAACA|GGAAAAGCAC|AATCAACAGT|CTGAATTTAC|TGTTGAAAGC|900|
|TTGATAGCCA|CTGTAACTGA|TATGTTTGGG|GCTGGAACAG|AGACAACGAG|CACCACTCTG|960|
|AGATATGGAC|TCCTGCTCCT|GCTGAAGTAC|CCAGAGGTCA|CAGCTAAAGT|CCAGGAAGAG|1020|
|ATTGAATGTG|TAGTTGGCAG|AAACCGGAGC|CCCTGTATGC|AGGACAGGAG|TCACATGCCC|1080|
|TACACAGATG|CTGTGGTGCA|CGAGATCCAG|AGATACATTG|ACCTCCTCCC|CACCAACCTG|1140|
|CCCCATGCAG|TGACCTGTGA|TGTTAAATTC|AAAAACTACC|TCATCCCCAA|GGGCATGACC|1200|
|ATAATAACAT|CCCTGACTTC|TGTGCTGCAC|AATGACAAAG|AATTCCCCAA|CCCAGAGATG|1260|
|TTTGACCCTG|GCCACTTTCT|GGATAAGAGT|GGCAACTTTA|AGAAAAGTGA|CTACTTCATG|1320|
|CCTTTCTCAG|CAGGAAAACG|GATGTGTATG|GGAGAGGGCC|TGGCCCGCAT|GGAGCTGTTT|1380|
|TTATTCCTGA|CCACCATTTT|GCAGAACTTT|AACCTGAAAT|CTCAGGTTGA|CCCAAAGGAT|1440|
|ATTGACATCA|CCCCCATTGC|CAATGCATTT|GGTCGTGTGC|CACCCTTGTA|CCAGCTCTGC|1500|
|TTCATTCCTG|TCTGAAGAAG|GGCAGATAGT|TTGGCTGCTC|CTGTGCTGTC|ACCTGCAATT|1560|
|CTCCCTTATC|AGGGCCATTG|GCCTCTCCCT|TCTCTCTATG|AGGGATATTT|TCTCTGACTT|1620|
|GTCAATCCAC|ATCTTCCCAT|TCCCTCAAGA|TCCAATGAAC|ATCCAACCTC|CATTAAAGAG|1680|
|AGTTCTTGG|GTCACTTCCT|AAATATATCT|GCTATTCTCC|ATACTCTGTA|TCACTTGTAT|1740|
|TGACCACCAC|ATATGCTAAT|ACCTATCTAC|TGCTGAGTTG|TCAGTATGTT|ATCACTATAA|1800|
|AACAAAGAAA|AATGATTAAT|AAATGACAAT|TCAGAGCCAT|TTATTCTCTG|CATGCTCTAG|1860|
|ATAAAAATGA|TTATTATTTA|CTGGGTCAGT|TCTTAGATTT|CTTTCTTTTG|AGTAAAATGA|1920|
|AAGTAAGAAA|TGAAAGAAAA|TAGAATGTGA|AGAGGCTGTG|CTGGCCCTCA|TAGTGTTAAG|1980|
|CACAAAAAGG|GAGAAAGGTA|AGAGGGTAGG|AAAGCTGTTT|TAGCTAAATG|CCACCTAGAG|2040|
|TTATTGGAGG|TCTGAATTTG|GAAAAAAAAA|CTATGTCCAG|GAGCAGCTGT|AACCTGTAGG|2100|
|GAAATAATGG|AACAATCATC|CATAAGAGGG|ATGAACATTA|AGTGTTTGAA|TTCATGCTCT|2160|
|GCTTTTGTGT|TACTGTAAAC|ACAAGATCAA|GATTTGGATA|ATCTTTTTCC|TTTGTGTTTC|2220|
|CAACTTAGAT|CATGTCTAAA|TATATGCTTT|CATATGGC| | |2258|

( 2 ) INFORMATION FOR SEQ ID NO:13:

( i ) SEQUENCE CHARACTERISTICS:
        ( A ) LENGTH: 490 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: YES (xi) SEQUENCE DESCRIPTION: SEQ ID NO:13:

| | | | | | | | | | | | | | | |
|---|---|---|---|---|---|---|---|---|---|---|---|---|---|---|
| Met | Asp | Pro | Xaa | Val | Val | Leu | Val | Leu | Cys | Leu | Ser | Cys | Leu | Leu | Leu |
| 1 | | | | 5 | | | | | 10 | | | | | 15 |
| Leu | Ser | Leu | Trp | Arg | Gln | Ser | Ser | Gly | Arg | Gly | Lys | Leu | Pro | Pro | Gly |
| | | | 20 | | | | | 25 | | | | | 30 | | |
| Pro | Thr | Pro | Leu | Pro | Xaa | Ile | Gly | Asn | Ile | Leu | Gln | Ile | Asp | Xaa | Lys |
| | | 35 | | | | | 40 | | | | | 45 | | | |
| Asp | Ile | Ser | Lys | Ser | Leu | Thr | Asn | Xaa | Ser | Lys | Val | Tyr | Gly | Pro | Val |
| | 50 | | | | | 55 | | | | | 60 | | | | |
| Phe | Thr | Xaa | Tyr | Phe | Gly | Leu | Lys | Pro | Ile | Val | Val | Leu | His | Gly | Tyr |
| 65 | | | | | 70 | | | | | 75 | | | | | 80 |
| Glu | Ala | Val | Lys | Glu | Ala | Leu | Ile | Asp | Leu | Gly | Glu | Glu | Phe | Ser | Gly |
| | | | | 85 | | | | | 90 | | | | | 95 | |
| Arg | Gly | Xaa | Phe | Pro | Leu | Ala | Glu | Arg | Ala | Asn | Xaa | Gly | Xaa | Gly | Ile |
| | | | 100 | | | | | 105 | | | | | 110 | | |
| Val | Phe | Ser | Asn | Gly | Lys | Arg | Trp | Lys | Glu | Ile | Arg | Arg | Phe | Ser | Leu |
| | | | 115 | | | | | 120 | | | | | 125 | | |
| Met | Thr | Leu | Arg | Asn | Phe | Gly | Met | Gly | Lys | Arg | Ser | Ile | Glu | Asp | Arg |
| | 130 | | | | | 135 | | | | | 140 | | | | |
| Val | Gln | Glu | Glu | Ala | Arg | Cys | Leu | Val | Glu | Glu | Leu | Arg | Lys | Thr | Lys |
| 145 | | | | | 150 | | | | | 155 | | | | | 160 |
| Ala | Ser | Pro | Cys | Asp | Pro | Thr | Phe | Ile | Leu | Gly | Cys | Ala | Pro | Cys | Asn |
| | | | | 165 | | | | | 170 | | | | | 175 | |
| Val | Ile | Cys | Ser | Xaa | Ile | Phe | His | Lys | Arg | Phe | Asp | Tyr | Lys | Asp | Gln |
| | | | 180 | | | | | 185 | | | | | 190 | | |
| Gln | Phe | Leu | Asn | Leu | Met | Glu | Lys | Xaa | Asn | Glu | Asn | Ile | Arg | Ile | Leu |
| | | 195 | | | | | 200 | | | | | 205 | | | |
| Ser | Ser | Pro | Trp | Ile | Gln | Xaa | Cys | Asn | Asn | Phe | Pro | Xaa | Xaa | Ile | Asp |
| | 210 | | | | | 215 | | | | | 220 | | | | |
| Tyr | Phe | Pro | Gly | Thr | His | Asn | Lys | Leu | Leu | Lys | Asn | Val | Ala | Phe | Met |
| 225 | | | | | 230 | | | | | 235 | | | | | 240 |
| Lys | Ser | Tyr | Ile | Leu | Glu | Lys | Val | Lys | Glu | His | Gln | Glu | Ser | Xaa | Asp |
| | | | | 245 | | | | | 250 | | | | | 255 | |
| Met | Asn | Asn | Pro | Arg | Asp | Phe | Ile | Asp | Cys | Phe | Leu | Ile | Lys | Met | Glu |
| | | | 260 | | | | | 265 | | | | | 270 | | |
| Xaa | Glu | Lys | His | Asn | Gln | Gln | Ser | Glu | Phe | Thr | Ile | Glu | Ser | Leu | Xaa |
| | | 275 | | | | | 280 | | | | | 285 | | | |
| Xaa | Thr | Xaa | Xaa | Asp | Leu | Phe | Gly | Ala | Gly | Thr | Glu | Thr | Thr | Ser | Thr |
| | 290 | | | | | 295 | | | | | 300 | | | | |
| Thr | Leu | Arg | Tyr | Xaa | Leu | Leu | Leu | Leu | Leu | Lys | His | Pro | Glu | Val | Thr |
| 305 | | | | | 310 | | | | | 315 | | | | | 320 |
| Ala | Lys | Val | Gln | Glu | Glu | Ile | Glu | Arg | Val | Ile | Gly | Arg | Asn | Arg | Ser |
| | | | | 325 | | | | | 330 | | | | | 335 | |
| Pro | Cys | Met | Gln | Asp | Arg | Ser | His | Met | Pro | Tyr | Thr | Asp | Ala | Val | Val |
| | | | 340 | | | | | 345 | | | | | 350 | | |
| His | Glu | Xaa | Gln | Arg | Tyr | Ile | Asp | Leu | Leu | Pro | Thr | Ser | Leu | Pro | His |
| | | 355 | | | | | 360 | | | | | 365 | | | |
| Ala | Val | Thr | Cys | Asp | Val | Lys | Phe | Arg | Asn | Tyr | Leu | Ile | Pro | Lys | Gly |
| | 370 | | | | | 375 | | | | | 380 | | | | |
| Thr | Thr | Ile | Leu | Thr | Ser | Leu | Thr | Ser | Val | Leu | His | Asp | Xaa | Lys | Glu |
| 385 | | | | | 390 | | | | | 395 | | | | | 400 |

```
        Phe   Pro   Asn   Pro   Glu   Met   Phe   Asp   Pro   Gly   His   Phe   Leu   Asp   Xaa   Gly
                          405                           410                           415

Gly   Asn   Phe   Lys   Lys   Ser   Asp   Tyr   Phe   Met   Pro   Phe   Ser   Ala   Gly   Lys
                          420                           425                           430

Arg   Ile   Cys   Val   Gly   Glu   Gly   Leu   Ala   Arg   Met   Glu   Leu   Phe   Leu   Phe
                          435                           440                           445

Leu   Thr   Thr   Ile   Leu   Gln   Asn   Phe   Asn   Leu   Lys   Ser   Leu   Val   Asp   Pro
                          450                           455                           460

Lys   Xaa   Leu   Asp   Thr   Thr   Pro   Val   Val   Asn   Gly   Phe   Ala   Ser   Val   Pro
        465                           470                           475                           480

Pro   Phe   Tyr   Gln   Leu   Cys   Phe   Ile   Pro   Val
                          485                           490
```

( 2 ) INFORMATION FOR SEQ ID NO:14:

( i ) SEQUENCE CHARACTERISTICS:
     ( A ) LENGTH: 1892 base pairs
     ( B ) TYPE: nucleic acid
     ( C ) STRANDEDNESS: single
     ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:14:

```
AGTGAAAGCC  CGCAGTTGTC  TTACTAAGAA  GAGAAGNCTT  CAATGGATCC  TNTTGTGGTC   60
CTNGTGCTCT  GTCTCTCATG  TTTGCTTCTC  CTTTCACTCT  GGAGACAGAG  CTCTGGGAGA  120
GGNAANCTCC  CTCCTGGCCC  CACTCCTCTC  CCANTNATTG  GAAATATCCT  ACAGATAGAT  180
NTTAAGGACA  TCAGCAAATC  CTTAACCAAT  NTCTCAAAAG  TCTATGGCCC  TGTGTTCACT  240
NTGTATTTTG  GCCTGAAACC  CATAGTGGTG  NTGCATGGAT  ATGAAGCAGT  GAAGGAAGCC  300
CTGATTGATC  NTGGAGAGGA  GTTTCTGGA   AGAGGCANTT  TCCCACTGGC  TGAAAGAGNT  360
AACANAGGAN  TTGGAATCGT  TTTCAGCAAT  GGAAAGAGAT  GGAAGGAGAT  CCGGCGTTTC  420
TCCCTCATGA  CGCTGCGGAA  TTTTGGGATG  GGAAGAGGA   GCATTGAGGA  CCGTGTTCAA  480
GAGGAAGCCC  GCTGCCTTGT  GGAGGAGTTG  AGAAAAACCA  AGGCCTCACC  CTGTGATCCC  540
ACTTTCATCC  TGGGCTGTGC  TCCCTGCAAT  GTGATCTGCT  CCNTTATTTT  CCATAAACGN  600
TTTGATTATA  AAGATCAGNA  ATTTCTTAAC  TTGATGGAAA  AATTNAATGA  AAACATCAGG  660
ATTCTGAGCN  CCCCNTGGAT  CCAGNTCTGC  AATAATTTNC  CTCCTNTCAT  TGATTATTTC  720
CCNGGAACTC  ANAACAAATT  ACTTAAAAAN  GTTGCTTTTA  TGAAAAGTTA  TATTTTGGAG  780
AAAGTAAAAG  AACACCAAGA  ATCANTGGAC  ATGAACAANC  CTCGGGACTT  TATTGATTGC  840
TTCCTGATCA  AAATGGAGNA  GGAAAAGCAC  AACCAACAGT  CTGAATTTAC  TATTGAAAGC  900
TTGGTANNCA  CTGNAGCTGA  NTTGTTTGGA  GCTGGNACAG  AGACAACAAG  CACNACNCTG  960
AGATATGNNC  TCCTNCTCCT  GCTGAAGCAC  CCAGAGGTCA  CAGCTAAAGT  CCAGGAAGAG 1020
ATTGAACGTG  TAATTGGCAG  AAACCGGAGC  CCCTGCATGC  AGGACAGGAG  CCACATGCCC 1080
TACACAGATG  CTGTGGTGCA  CGAGNTCCAG  AGATACATTG  ACCTNCTCCC  CACCAGCCTG 1140
CCCCATGCAG  TGACCTGTGA  NNTTAAATTC  AGAAACTACC  TCATNCCCAA  GGGCACAACC 1200
ATANTAACNT  CCCTGACTTC  TGTGCTACAT  GANNACAAAG  AATTTCCCAA  CCCAGAGATG 1260
TTTGACCCTN  GNCACTTTCT  GGATNANNGT  GGCAANTTTA  AGAAAAGTNA  CTACTTCATG 1320
CCTTTCTCAG  CAGGAAAACG  GATTTGTGTG  GGAGANGGCC  TGGCCCGCAT  GGAGCTGTTT 1380
TTATTCCTGA  CCNCCATTTT  ACAGAACTTT  AACCTGAAAT  CTCTGGTTGA  CCCAAANGAC 1440
```

```
CTTGACACCA CTCCAGTTGN CAATGGATTT GCTTCTGTGC CNCCCTTCTA CCAGCTNTGC    1500

TTCATTCCTG TCTGAAGAAG GGCAGATGGT CTGGCTGCTN CTGTGCTGTC NCNNNNNNTN    1560

NNTTTNNTCT GGGGCAATTT CCNTCTTNCA TNNNTNTTNN TGCNNTTTNT CATCTGNCAT    1620

CTCACANTNC NNCTTCCCTT ANCATCNAGN NACCATTNAN NNNCAATNTC CAAGAGNGTG    1680

NNTTTNTTNN CTNTCCACCT ANATCTATCN NTNNNNCTNC TNTNTNTNNA TNACTTTGAT    1740

TGTCCNCTAN TGATGNTAAT TNTTAATAT TGNNTTATTG NNANNNTNTT ATNANTNANA    1800

AANAAATGAT AATTNTNTNN AAATNNNAAG TCANTGCNNT TNANNATNTN CNNAATAAAA    1860

AGCATTATTA TTTGCTGAAA AAAAGTCAGT TC                                 1892
```

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
GCAAGCTTAA AAAATGGATC CAGCTGTGGC TCT                                  33
```

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GCAAGCTTGC CAAACTATCT GCCCTTCT                                        28
```

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
ACTTTTCAAT GTAAGCAAAT                                                 20
```

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
TTAGTAATTC TTTGAGATAT                                                 20
```

( 2 ) INFORMATION FOR SEQ ID NO:19:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:19:

CTGTTAGCTC TTTCAGCCAG 20

( 2 ) INFORMATION FOR SEQ ID NO:20:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:20:

GGAGCACAGC CCAGGATGAA 20

( 2 ) INFORMATION FOR SEQ ID NO:21:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:21:

GCAAGCTTAA AAAATGGATC CAGCTGTGGC TCT 33

( 2 ) INFORMATION FOR SEQ ID NO:22:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:22:

GCAAGCTTGC CAAACTATCT GCCCTTCT 28

( 2 ) INFORMATION FOR SEQ ID NO:23:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:23:

TGGCCCTGAT AAGGGAGAAT 20

( 2 ) INFORMATION FOR SEQ ID NO:24:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:24:

ATCCAGAGAT ACATTGACCT C          21

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:25:

CCATGAAGTG ACCTGTGATG          20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:26:

AAAGATGGAT AATGCCCCAG          20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:27:

GAAGGAGATC CGGCGTTTCT          20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:28:

GGCGTTTCTC CCTCATGACG          20

( 2 ) INFORMATION FOR SEQ ID NO:29:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:29:

TTGTCATTGT GCAG                                                                                14

( 2 ) INFORMATION FOR SEQ ID NO:30:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:30:

CACATGCCCT ACACA                                                                               15

( 2 ) INFORMATION FOR SEQ ID NO:31:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:31:

TGACGCTGCG GAATT                                                                               15

( 2 ) INFORMATION FOR SEQ ID NO:32:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:32:

GGACTTTATT GATTG                                                                               15

( 2 ) INFORMATION FOR SEQ ID NO:33:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:33:

ATGATTCTCT TGTGGTCCT                                                                           19

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:34:

AAAGATGGAT AATGCCCCCA G                                                                        21

( 2 ) INFORMATION FOR SEQ ID NO:35:

-continued ( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:35:

GCAAGCTTAA AAAAATGGAA CCTTTTGTGG TCCT    34

( 2 ) INFORMATION FOR SEQ ID NO:36:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:36:

GCAAGCTTGC CAGATGGGCT AGCATTCT    28

( 2 ) INFORMATION FOR SEQ ID NO:37:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:37:

GCAAGCTTAA AAAAATGGAT TCTCTTGTGG TCCT    34

( 2 ) INFORMATION FOR SEQ ID NO:38:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:38:

GCAAGCTTGC CAGGCCATCT GCTCTTCT    28

( 2 ) INFORMATION FOR SEQ ID NO:39:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:39:

GCAAGCTTAA AAAAATGGAT TCTCTTGTGG TCCT    34

( 2 ) INFORMATION FOR SEQ ID NO:40:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:40:

GCAAGCTTGC CAGACCATCT GTGCTTCT                28

( 2 ) INFORMATION FOR SEQ ID NO:41:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (oligo)

( x i ) SEQUENCE DESCRIPTION: SEQ ID NO:41:

AGCTTAAAAA AATG                14

( 2 ) INFORMATION FOR SEQ ID NO:42:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (oligo)

( x i ) SEQUENCE DESCRIPTION: SEQ ID NO:42:

GATCCATTTT TTTA                14

( 2 ) INFORMATION FOR SEQ ID NO:43:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:43:

Cys Ile Asp Tyr Leu Pro Gly Ser His Asn Lys Ile Ala Glu Asn Phe
1               5                   10                  15

Ala ( 2 ) INFORMATION FOR SEQ ID NO:44:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:44:

Cys Leu Ala Phe Met Glu Ser Asp Ile Leu Glu Lys Val Lys
1               5                   10